United States Patent [19]
Gaster et al.

[11] Patent Number: 5,972,951
[45] Date of Patent: Oct. 26, 1999

[54] TETRACYCLIC SPIRO COMPOUNDS, PROCESS FOR THEIR PREPARATION AND THEIR USE AS 5HT$_{1D}$ RECEPTOR ANTAGONISTS

[75] Inventors: Laramie Mary Gaster; Francis David King, both of Bishop's Stortford; Paul Adrian Wyman, Epping, all of United Kingdom

[73] Assignee: SmithKline Beecham plc, Brentford, United Kingdom

[21] Appl. No.: 08/849,932

[22] PCT Filed: Dec. 6, 1995

[86] PCT No.: PCT/EP95/04889

§ 371 Date: Oct. 2, 1997

§ 102(e) Date: Oct. 2, 1997

[87] PCT Pub. No.: WO96/19477

PCT Pub. Date: Jun. 27, 1996

[30] Foreign Application Priority Data

Dec. 22, 1994 [GB] United Kingdom ............... 9426029
Jun. 24, 1995 [GB] United Kingdom ............... 9512920

[51] Int. Cl.$^6$ ................. A61K 31/435; C07D 471/20
[52] U.S. Cl. ................. 514/278; 514/215; 514/409; 540/543; 546/17; 548/409
[58] Field of Search ............... 546/17; 540/543; 548/409; 514/215, 278, 409

[56] References Cited

U.S. PATENT DOCUMENTS 5,358,948 10/1994 Bradshaw et al. ............... 514/252

OTHER PUBLICATIONS

Journal of Medicinal Chemistry, (1980) vol. 23, No. 6, Washington U.S., pp. 679–682, P.A. Crooks et al., "Synthesis and analgesic properties of some conformationally restriction analogues of profadol" p. 680.

Journal of Medicinal Chemistry, (Jul. 1994) vol. 37, No. 15, 22 Washington U.S., pp. 2253–2257, J.W. Clitherow et al. Evolution of a novel series of (N, N–dimethylamino)propyl and piperazinylbenzanilides as the first selective 5–HT1D–antagonists' see table 2.

*Primary Examiner*—Bernard Dentz
*Attorney, Agent, or Firm*—Wayne J. Dustman; William T. King; Charles M. Kinzig

[57] ABSTRACT

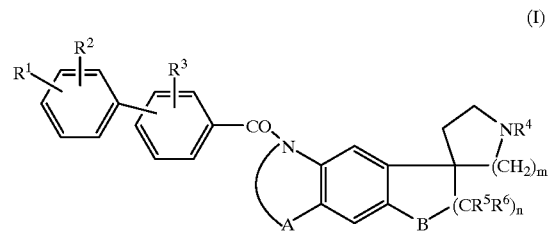

Novel piperidine derivatives of formula (I), processes for their preparation, pharmaceutical compositions containing them and their use as medicaments for the treatment of CNS disorders are disclosed.

12 Claims, No Drawings

TETRACYCLIC SPIRO COMPOUNDS, PROCESS FOR THEIR PREPARATION AND THEIR USE AS 5HT$_{1D}$ RECEPTOR ANTAGONISTS

This application is a 371 of PCT/EP95/04889 filed Dec. 6, 1996.

The present invention relates to novel piperidine derivatives, processes for their preparation, and pharmaceutical compositions containing them.

EPA 0 533 266/7/8 disclose a series of benzanilide derivatives which are said to possess 5HT$_{1D}$ receptor antagonist activity. These compounds are said to be of use in the treatment of various CNS disorders.

A structurally distinct class of compounds have now been discovered and have been found to exhibit 5HT$_{1D}$ antagonist activity. In a first aspect, the present invention therefore provides a compound of formula (I) or a salt or N-oxide thereof:

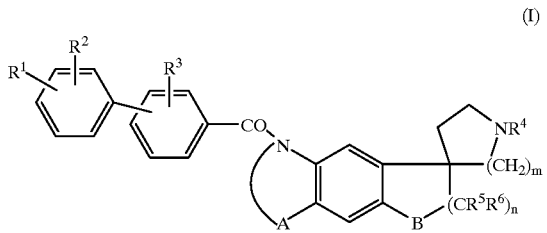

in which

R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_p$CO$_2$R$^{11}$, (CH$_2$)$_p$NR$^{10}$R$^{11}$, (CH$_2$)$_p$CONR$^{10}$R$^{11}$, (CH$_2$)$_{Tp}$NR$^{10}$COR$^{11}$, (CH$_2$)$_{Tp}$CO$_2$C$_{1-6}$alkyl, CO$_2$(CH$_2$)$_p$OR$^{10}$, CONHNR$^{10}$R$^{11}$, NR$^{10}$R$^{11}$, NR$^{10}$CO$_2$R$^{11}$, NR$^{10}$CO(CH$_2$)$_p$NR$^{10}$R$^{11}$, NR$^{10}$CONR$^{10}$R$^{11}$, CR$^{10}$=NOR$^{11}$, CNR$^{10}$=NOR$^{11}$, where R$^9$, R$^{10}$ and R$^{11}$ are independently hydrogen or C$_{1-6}$alkyl and p is 1 to 4; or R$^1$ is an optionally substituted 5 to 7-membered heterocyclic ring containing 1 to 4 heteroatoms selected from oxygen, nitrogen or sulphur;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl;

R$^4$ is hydrogen or C$_{1-6}$alkyl;

R$^5$ and R$^6$ are independently hydrogen or C$_{1-6}$alkyl;

A is (CR$^{13}$R$^{14}$)$_q$ where q is 2, 3 or 4 and R$^{13}$ and R$^{14}$ are independently hydrogen or C$_{1-6}$alkyl or A is (CR$^{13}$R$^{14}$)$_r$-D where r is 0, 1, 2 or 3 and D is oxygen, sulphur or CR$^{13}$=CR$^{14}$.

B is oxygen, CR$^{15}$R$^{16}$ or NR$^{17}$ where R$^{15}$, R$^{16}$ and R$^{17}$ are independently hydrogen or C$_{1-6}$alkyl or B is S(O)$_b$ where b is 0, 1 or 2;

m is 1, 2 or 3; and n is 1, 2 or 3.

C$_{1-6}$alkyl groups, whether alone or as part of another group, may be straight chain or branched.

Suitably R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_p$CO$_2$R$^{11}$, (CH$_2$)$_p$NR$^{10}$R$^{11}$, (CH$_2$)$_p$CONR$^{10}$R$^{11}$, (CH$_2$)$_p$NR$^{10}$COR$^{11}$, (CH$_2$)$_p$CO$_2$C$_{1-6}$alkyl, CO$_2$(CH$_2$)$_p$OR$^{10}$, CONHNR$^{10}$R$^{11}$, NR$^{10}$R$^{11}$, NR$^{10}$CO$_2$R$^{11}$, NR$^{10}$CO(CH$_2$)$_p$NR$^{10}$R$^{11}$, NR$^{10}$CONR$^{10}$R$^{11}$, CR$^{10}$=NOR$^{11}$, CNR$^{10}$=NOR$^{11}$, where R$^9$, R$^{10}$ and R$^{11}$ are independently hydrogen or C$_{1-6}$alkyl and p is 1 to 4. preferred groups include cyano, COC$_{1-6}$alkyl, CR$^{10}$=NOR$^{11}$, (CH$_2$)$_p$NR$^{10}$COR$^{11}$, CO$_2$R$^{10}$, NR$^{10}$SO$_2$R$^{11}$, SO$_2$NR$^{10}$R$^{11}$, CONR$^{10}$R$^{11}$, CONHNR$^{10}$R$^{11}$, NR$^{10}$CO$_2$R$^{11}$, NR$^{10}$CONR$^{10}$R$^{11}$, CONHNR$^{10}$R$^{11}$ or SO$_2$R$^9$. Preferably alkyl groups, including R$^{10}$ and R$^{11}$, are methyl and ethyl.

When R$^1$ is a 5 to 7-membered heterocyclic ring containing 1 to 3 heteroatoms selected from oxygen, nitrogen or sulphur suitable heterocyclic rings include thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl and pyrazinyl. The heterocyclic rings can be linked to the remainder of the molecule via a carbon atom or, when present, a nitrogen atom. Suitable substituents for these rings include R$^2$ and R$^3$ groups as defined above. Preferably R$^1$ is optionally substituted triazolyl, thiazolyl, isoxazolyl, pyrazinyl or oxadiazolyl. Most preferably R$^1$ is optionally substituted oxadiazolyl. Preferred substituents for such oxadiazolyl groups include C$_{1-6}$alkyl such as methyl or ethyl, and NR$^{10}$R$^{11}$ as defined above, preferably where R$^{10}$ and R$^{11}$ are C$_{1-6}$alkyl. Most preferably R$^1$ is a 5-methyl-1,2,4-oxadiazol-3-yl group or a 5-methyl-1,3,4-oxadiazol-2-yl group.

Suitably R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl. Preferably R$^2$ is hydrogen or C$_{1-6}$alkyl, in particular methyl. Preferably R$^3$ is hydrogen.

Suitably R$^4$ is hydrogen or C$_{1-6}$alkyl. Preferably R$^4$ is hydrogen, methyl or ethyl, most preferably R$^4$ is methyl. Preferably m is 2 forming a spiro-piperidine ring, Suitably R$^5$ and R$^6$ are independently hydrogen or C$_{1-6}$alkyl. Preferably R$^5$ and R$^6$ are both hydrogen.

Suitably A is (CR$^{13}$R$^{14}$)$_q$ where q is 2, 3 or 4 and R$^{13}$ and R$^{14}$ are independently hydrogen or C$_{1-6}$alkyl or A is (CR$^{13}$R$^{14}$)$_r$-D where r is 0, 1, 2 or 3 and D is oxygen, sulphur or CR$^{13}$=CR$^{14}$. Preferably A is (CH$_2$)$_2$ or (CH$_2$)$_3$.

Suitably B is oxygen, CR$^{15}$R$^{16}$ or NR$^{17}$ where R$^{15}$, R$^{16}$ and R$^{17}$ are independently hydrogen or C$_{1-6}$alkyl or B is S(O)$_b$ where b is 0, 1 or 2. Preferably B is oxygen or sulphur, most preferably B is oxygen.

Suitably n is 1, 2 or 3, preferably n is 1.

Particularly preferred compounds of the invention include:

1'-Methyl-5-(2'-methyl-4'-(5-methyl-1,2,4-oxadiazol-3-yl)biphenyl-4-carbonyl)-2,3,6,7-tetrahydrospiro[furo[2,3-f]indole-3,4'-piperidine], 2,3,5,6,7,8-Hexahydro-1'-methyl-5-(2'-methyl-4'-(5-methyl-1,2,4-oxadiazol-3-yl)biphenyl-4-carbonyl)spiro[furo[2,3-g]quinoline-3,4'-piperidine], 5-(2'-Methyl-4'-(5-methyl-1,2,4-oxadiazol-3-yl)biphenyl-4-carbonyl)-2,3,6,7-tetrahydrospiro[furo[2,3-f]indole-3,4'-piperidine], 1'-Ethyl-5-(2'-methyl-4'-(5-methyl-1,2,4-oxadiazol-3-yl)biphenyl-4-carbonyl)-2,3,6,7-tetrahydrospiro[furo[2,3-f]indole-3,4'-piperidine], 1'-Methyl-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine], 5-(4'-(5-Dimethylamino-1,2,4-oxadiazol-3-yl)-2'-methylbiphenyl-4-carbonyl)-1'-methyl-2,3,6,7-tetrahydrospiro[furo[2,3-f]indole-3,4'-piperidine], 1'-Methyl-5-[4'-(5-methyl-1,2,4-oxadiazol-3-yl)biphenyl-4-carbonyl]-2,3,6,7-tetrahydrospiro[furo[2,3-f]indole-3,4'-piperidine], 2,3-Dihydro-1'-methyl-5-(2'-methyl-4'-(5-methyl-1,2,4-oxadiazol-3-yl)biphenyl-4-carbonyl)spiro[furo[2,3-f]indole-3,4'-piperidine], 5-[4'-Cyano-2'-methylbiphenyl-4-carbonyl]-1'-methyl-2,3,6,7-tetrahydrospiro[furo[2,3-f]indole-3,4'-piperidine], 5-(4'-Acetyl-2'-methylbiphenyl-4-carbonyl)-1'-methyl-2,3,6,7-tetrahydrospiro[furo[2,3-f]indole-3,4'-piperidine], 5-(4'-(1-(Methoxyamino)ethyl)-2'-methylbiphenyl-4-carbonyl)-1'-methyl-2,3,6,7-tetrahydrospiro[furo[2,3-f]indole-3,4'-piperidine], 5-(4'-Acetamidomethyl-2'-methylbiphenyl-4-carbonyl)-1'-methyl-2,3,6,7-tetrahydrospiro[furo[2,3-f]indole-3,4'-piperidine], 3,5,6,7,8,9-Hexahydro-1'-methyl-5-(2'-methyl-4'-(5-methyl-1,2,4-oxadiazol-3-yl)biphenyl-4-carbonyl)spiro[2H-furo[2,3-h]benzazepine-3,4'-piperidine], 1'-Methyl-5-(2'-methyl-4'-(3-methyl-1,2,4-oxadiazol-5-yl)biphenyl-4-carbonyl)-2,3,6,7-tetrahydrospiro[furo[2,3-f]indole-3,4'-piperidine], 1'-Methyl-5-(2'-methyl-4'-(1,3,4-oxadiazol-2-yl)biphenyl-4-carbonyl)-2,3,6,7-tetrahydrospiro[furo[2,3-f]indole-3,4'-piperidine, 5-[4'-(5-Ethyl-1,3,4-oxadiazol-2-yl)-2'-methylbiphenyl-4-carbonyl]-1'-methyl-2,3,6,7-tetrahydrospiro[furo[2,3-f]indole-3,4'-piperidine], 5-[2'-Methyl-4'-(5-methyl-1,3,4-oxadiazol-2yl)biphenyl-4-carbonyl]-2,3,6,7-tetrahydrospiro[furo[2,3-f]indole-3,4'-piperidine], 2,3-Dihydro-1'-methyl-5-(2'-methyl-4'-(5-methyl-1,3,4-oxadiazol-2-yl)biphenyl-4-carbonyl)spiro[furo[2,3-f]indole-3,4'-piperidine], 5-(2,2'-Dimethyl-4'-(5-methyl-1,3,4-oxadiazol-2-yl)biphenyl-4-carbonyl)-1'-methyl-2,3,6,7-tetrahydrospiro[furo[2,3-f]indole-3,4'-piperidine], 5-(2,3'-Dimethyl-4'-(5-methyl-1,3,4-oxadiazol-2-yl)biphenyl-4-carbonyl)-1'-methyl-2,3,6,7-tetrahydrospiro[furo[2,3-f]indole-3,4'-piperidine], 1'-Methyl-5-(2'-methyl-4'-(4-methylthiazol-2-yl)biphenyl-4-carbonyl)-2,3,6,7-tetrahydrospiro[furo[2,3-f]indole-3,4'-piperidine], 5-(4'-Methoxycarbonyl-2'-methylbiphenyl-4-carbonyl)-1'-methyl-2,3,6,7-tetrahydrosiro[furo[2,3-f]indole-3,4'-piperidine], 5-(5'-Methoxycarbonyl-2'-methylbiphenyl-4-carbonyl)-1'-methyl-2,3,6,7-tetrahydrospiro[furo[2,3-f]indole-3,4'-piperidine], 5-[4'-(Methanesulphonamino)-2'-methylbiphenyl-4-carbonyl]-1'-methyl-2,3,6,7-tetrahydrospiro[furo[2,3-f]indole-3,4'-piperidine], 5-(4'-Hydrazinocarbonyl-2'-methylbiphenyl-4-carbonyl)-1'-methyl-2,3,6,7-tetrahydrospiro[furo[2,3-f]indole-3,4'-piperidine], 1'-Ethyl-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine], 1'-Methyl-5-(2'-methyl-5'-(5-methyl-1,3,4-oxadiazol-2-yl)biphenyl-4-carbonyl)-2,3,6,7-tetrahydrospiro[furo[2,3-f]indole-3,4'-piperidine], 5-(4'-Carboxamido-2'-methylbiphenyl-4-carbonyl)-1'-methyl-2,3,6,7-tetrahydrospiro[furo[2,3-f]indole-3,4'-piperidine], 5-(4'-Acetamido-2'-methylbiphenyl-4-carbonyl)-1'-methyl-2,3,6,7-tetrahydrospiro[furo[2,3-f]indole-3,4'-piperidine], 2,3,5,6,7,8-Hexahydro-1'-methyl-5-(2'-methyl-4'-(5-methyl-1,3,4-oxadiazol-2-yl)biphenyl-4-carbonyl)spiro[furo[2,3-g]quinoline-3,4'-piperidine], 2,3,5,6,7,8-Hexahydro-5-(4'-methanesulphonamino-2'-methylbiphenyl-4-carbonyl)-1'-methylspiro[furo[2,3-g]quinoline-3,4'-piperidine], 1'-Methyl-5-[2'-methyl-4'-(5-methyl-1,2,4-oxadiazol-3-yl)biphenyl-4-carbonyl]-2,3,6,7-tetrahydrospiro[thiopheno[2,3-f]indole-3,4'-piperidine], 1,2,3,5,6,7-Hexahydro-1'-methyl-1-(2'-methyl-4'-(5-methyl-1,3,4-oxadiazol-2-yl)biphenyl-4-carbonyl)spiro[indeno[5,6-b]pyrrole-7,4'-piperidine], 5-[4'-(N-methanesulphonyl-N-methylamino)-2'-methylbiphenyl-4-carbonyl]-1'-methyl-2,3,6,7-tetrahydrospiro[furo[2,3-f]indole-3,4'-piperidine], 5-[4'-(Dimethylaminosulphonyl)biphenyl-4-carbonyl]-1'-methyl-2,3,6,7-tetrahydrospiro[furo[2,3-f]indole-3,4'-piperidine], 5-[4'-(Methanesulphonyl)biphenyl-4-carbonyl]-1'-methyl-2,3,6,7-tetrahydrospiro[furo[2,3-f]indole-3,4'-piperidine], 5-[4'-(N,N-Dimethylcarbamoylamino)-2'-methylbiphenyl-4-carbonyl]-1'-methyl-2,3,6,7-tetrahydrospiro[furo[2,3-f]indole-3,4'-piperidine], 5-[4'-(Ethoxycarbonylamino)-2'-methylbiphenyl-4-carbonyl]-1'-methyl-2,3,6,7-tetrahydrospiro[furo[2,3-f]indole-3,4'-piperidine], 5-[4'-(4,5-Dimethyl-1,2,4-triazol-3-yl)-2'-methylbiphenyl-4-carbonyl]-1'-methyl-2,3,6,7-tetrahydrospiro[furo[2,3-f]indole-3,4'-piperidine], 1'-Methyl-6-[2'-methyl-4'-(5-methyl-1,3,4-oxadiazol-2-yl)biphenyl-4-carbonyl]-2,3,7,8-tetrahydrospiro[4H-pyrano[2,3-f]indole-4,4'-piperidine], 1'-Methyl-5-(2'-methyl-4'-(5-methyl-1,3,4-thiadiazol-2-yl)biphenyl-4-carbonyl)-2,3,6,7-tetrahydrospiro[furo[2,3-f]indole-3,4'-piperidine], 5-(2'-Methyl-4'-(5-methyl-1,3,4-oxadiazol-2-yl)biphenyl-4-carbonyl)-1'-n-propyl-2,3,6,7-tetrahydrospiro[furo[2,3-f]indole-3,4'-piperidine], 1'-Methyl-5-(2'-methyl-4'-(5-methyloxazol-2-yl)biphenyl-4-carbonyl)-2,3,6,7-tetrahydrospiro[furo[2,3-f]indole-3,4'-piperidine], 1'-Methyl-5-(2'-methyl-4'-(3-methylisoxazol-5-yl)biphenyl-4-carbonyl)-2,3,6,7-tetrahydrospiro[furo[2,3-f]indole-3,4'-piperidine], 1'-Methyl-5-(2'-methyl-4'-(5-methylisoxazol-3-yl)biphenyl-4-carbonyl)-2,3,6,7-tetrahydrospiro[furo[2,3-f]indole-3,4'-piperidine], 2,3,5,6,7,8-Hexahydro-1'-methyl-5-(4'-(5-dimethylamino-1,2,4-oxadiazol-3-yl)-2'-methylbiphenyl-4-carbonyl)spiro[furo[2,3-g]quinoline-3,4'-piperidine], 2,3,5,6,7,8-Hexahydro-1'-methyl-5-(4'-(5-ethyl-1,3,4-oxadiazol-2-yl)-2'-methylbiphenyl-4-carbonyl)spiro[furo[2,3-g]quinoline-3,4'-piperidine], 2,3,5,6,7,8-Hexahydro-1'-methyl-5-(4'-methoxycarbonyl-2'-methylbiphenyl-4-carbonyl)spiro[furo[2,3-g]quinoline-3,4'-piperidine], 2,3,5,6,7,8-Hexahydro-1'-methyl-5-(4'-hydrazinocarbonyl-2'-methylbiphenyl-4-carbonyl)spiro[furo[2,3-g]quinoline-3,4'-piperidine], 2,3,5,6,7,8-Hexahydro-1'-methyl-5-(2'-methyl-4'-(1,3,4-oxadiazol-2-yl)biphenyl-4-carbonyl)spiro[furo[2,3-g]quinoline-3,4'-piperidine], 1'-Methyl-5-(2'-methyl-4'-pyrazinylbiphenyl-4-carbonyl)-2,3,6,7-tetrahydrospiro[furo[2,3-f]indole-3,4'-piperidine], 1'-Methyl-5-[2'-methyl-4'-(5-methyl-1,2,4-oxadiazolyl-3-yl)biphenyl-4-carbonyl]-1-oxo-2,3,6,7-tetrahydrospiro[thiopheno[2,3-f]indole-3,4'-piperidine], 1'-Ethyl-5-[2'-methyl-4'-(5-methyl-1,3,4-oxadiazol-2-yl)biphenyl-4-carbonyl]-2,3,6,7-tetrahydrospiro[furo[2,3-f]indole-3,4'-piperidine], 1'-Methyl-5-[2'-methyl-4'-(1-methylimidazol-2yl)biphenyl-4-carbonyl]-2,3,6,7-tetrahydrospiro[furo[2,3-f]indole-3,4'-piperidine], 1'-Methyl-5-[2'-methyl-4'-(1-methylimidazol-5-yl)biphenyl-4-carbonyl]-2,3,6,7-tetrahydrospiro[furo[2,3-f]indole-3,4'-piperidine], 5-[4'-(5-Hydroxymethyl-1,2,4-oxadiazol-3-yl)-2'-methylbiphenyl-4-carbonyl]-1'-methyl-2,3,6,7-tetrahydrospiro[furo[2,3-f]indole-3,4'-piperidine], 1'-Methyl-5-(2'-methyl-4'-(5-methyl-1,2,4-oxadiazol-3-yl)biphenyl-4-carbonyl)-1'-oxo-2,3,6,7-tetrahydrospiro[furo[2,3-f]indole-3,4'-piperidine], 1'-Methyl-5-[2'-methyl-4'-(1,2,4-triazin-3-yl)biphenyl-4-carbonyl]-2,3,6,7-tetrahydrospiro[furo-[2,3-f]indole-3,4'-piperidine], 2,3,6,7,8,9-Hexahydro-1'-methyl-6-(2'-methyl-4'-(5-methyl-1,3,4-oxadiazol-2-yl)biphenyl-4-carbonyl)spiro[4H-pyrano[2,3-g]quinoline-4,4' piperdine], 1'-Ethyl-5-(2'-methyl-4'-(5-methyl-1,3,4-oxadiazol-2-yl)biphenyl-4-carbonyl)-1'-oxo-2,3,6,7-tetrahydrospiro[furo[2,3-f]indole-3,4'-piperidine], 1'-Ethyl-5-[4'-(5-methyl-1,3,4-oxadiazol-2-yl)biphenyl-4-carbonyl]-2,3,6,7-tetrahydrospiro[furo[2,3-f]indole-3,4'-piperidine], 1'-Ethyl-5-(4'-hydrazinocarbonyl-2'-methylbiphenyl-4-carbonyl)-2,3,6,7-tetrahydrospiro[furo[2,3-f]indole-3,4'-piperidine], 5-[4'-(Acetylhydrazinocarbonyl)-2'-methylbiphenyl-4-carbonyl]-1'-ethyl-2,3,6,7-tetrahydrospiro[furo[2,3-f]indole-3,4'-piperidine], 5-[4'-(5-Methoxymethyl-1,2,4-oxadiazol-3-yl)-2'-methylbiphenyl-4-carbonyl]-1'-methyl-2,3,6,7-tetrahydrospiro[furo[2,3-f]indole-3,4'-piperidine], 5-[4'-(4,5-Dihydrooxazol-2-yl)-2'-methylbiphenyl-4-carbonyl]-1'-methyl-2,3,6,7-tetrahydrospiro[furo[2,3-f]indole-3,4'-piperidine], 5-[4'-(2-(N,N-Dimethylamino)acetamido)-2'-methylbiphenyl-4-carbonyl]-1'-methyl-2,3,6,7-tetrahydrospiro[furo[2,3-f]indole-3,4'-piperidine]

5-[4'-(Ethoxycarbonylamino)-2'-methylbiphenyl-4-carbonyl]-1'-ethyl-2,3,6,7-tetrahydrospiro[furo[2,3-f]indole-3,4'-piperidine], 5-[4'-(Acetylhydrazinocarbonyl)-2'-methylbiphenyl-4-carbonyl]-1'-methyl-2,3,6,7-tetrahydrospiro[furo[2,3-f]indole-3,4'-piperidine], 5-(4'-(5-methylfuran-2-yl)-2'-methylbiphenyl-4-carbonyl)-1'-methyl-2,3,6,7-tetrahydrospiro[furo[2,3-f]indole-3,4'-piperidine], or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also form an aspect of the invention.

In a further aspect the present invention provides a process for the preparation of a compound of formula (I) which comprises:

(a) reaction of a compound of formula (II):

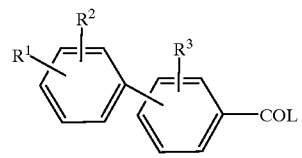

(II)

in which $R^1$, $R^2$ and $R^3$ are as defined in formula (I) and L is a leaving group with a compound of formula (III):

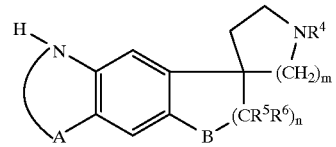

(III)

wherein $R^4$, $R^5$, $R^6$ A, B, m and n are as defined in formula (I) and optionally thereafter in any order:

converting a compound of formula (I) into another compound of formula (I)

forming a pharmaceutically acceptable salt.

Suitable activated carboxylic acid derivatives of formula (II) include acyl halides and acid anhydrides. Activated compounds (II) can also be prepared by reaction of the corresponding carboxylic acid with a coupling reagent such as carbonyldimidazole, dicyclohexylcarbodiimide or diphenylphosphorylazide. Preferably the group L is halo, particularly chloro.

A compound of formulae (II) and (III) are typically reacted together in an inert organic solvent such as DMF, THF or dichloromethane at ambient or elevated temperature in the presence of a base such as an alkali metal hydroxide, triethylamine or pyridine.

Intermediate compounds of formulae (II) can be prepared using standard procedures such as those outlined in EPA 533266/7/8. Certain intermediate compounds of formula (III) are novel and form a further aspect of the invention.

Alternatively L is an ester forming group such that the resulting esters of formula (II) can be reacted with compounds of formula (III) in the presence of an organoaluminium reagent such as trimethylaluminium. Such a reaction is typically carried out in the presence of an inert solvant such as toluene.

It will be appreciated to those skilled in that art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

$5HT_{1D}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include motor disorders such as Parkinson's disease, dementia in Parkinson's disease, neuroleptic-induced Parkinsonism and tardive dyskinesias, as well as other psychiatric disorders.

$5HT_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction and hypothermia.

Therefore, the present invention provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, convention flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

Description 1

4-(Hydroxymethyl)-1-methyl-1,2,3,6-tetrahydropyridine

To a solution of ethyl 1-methyl-1,2,3,6-tetrahydro-4-pyridinecarboxylate (10.0 ml, 0.061 mole) in THF (200 ml) was added, maintaining temperature below 25° C., lithium aluminium hydride (2.76 g, 0.073 mole). After stirring for a further 15 min, water (2.75 ml), 10% NaOH (4 ml) and water (4 ml) were successively added, and the mixture was filtered. The filtrate was dried ($Na_2SO_4$) and evaporated in vacuo to give the title compound as an amber oil (6.30 g, 81%), which solidified on standing.

$^1$H NMR (200 MHz, $CDCl_3$) δ(ppm): 5.63 (m, 1H), 4.01 (s, 2H), 2.94 (m, 2H), 2.55 (t, 2H), 2.35 (s, 3H), 2.20 (m, 2H)

Description 2

4-(2-Iodophenoxymethyl)-1-methyl-1,2,3,6-tetrahydropyridine 4-(Hydroxymethyl)-1-methyl-1,2,3,6-tetrahydropyridine (D1, 5.63 g, 0.044 mol), 2-iodophenol (7.80 g, 0.035 mol) and triphenylphosphine (11.61 g, 0.044 mol) were stirred in dry THF (200 ml) under Ar as diethyl azodicarboxylate (7.0 ml, 0.044 mol) was added portionwise. The solution was stirred for 1 h, concentrated, diluted with ethyl acetate, and extracted with dil. HCl. The extract was basified (sat. $K_2CO_3$ solution) and extracted with ethyl acetate. This organic extract was dried ($Na_2SO_4$) and evaporated to give a brown oil. Purification by chromatography on silica gel, eluting with 0–10% methanol/chloroform (gradient) gave the title compound (7.65 g, 65%) as an amber oil.

$^1$H NMR (200 MHz, $CDCl_3$) δ(ppm): 7.76 (dd, 1H), 7.27 (m, 1H), 6.81 (dd, 1H), 6.68 (td, 1H), 5.84 (m, 1H), 4.47 (s, 2H), 2.99 (m, 2H), 2.58 (t, 2H), 2.4–2.25 (m, 5H).

Description 3

2,3-Dihydro-1'-methylspiro[benzofuran-3,4'-piperidine]

4-(2-Iodophenoxymethyl)-1-methyl-1,2,3,6-tetrahydropyridine (D2, 8.72 g, 0.026 mol) and AIBN (0.20 g, 0.0012 mol) were stirred at reflux under Ar in benzene (500 ml) as tributyltin hydride (14.3 ml, 0.053 mol) was added dropwise in benzene (100 ml) over 1 h. The mixture was stirred at reflux for a further 4.5 h, cooled and evaporated. The residue was dissolved in ethyl acetate, and extracted with dil. HCl. The extract was basified (sat. $K_2CO_3$ solution) and extracted with ethyl acetate. This organic extract was dried ($Na_2SO_4$) and evaporated to give a brown solid, which was chromatographed on silica gel, eluting with 0–8% methanol/chloroform (gradient) to give the title compound (3.86 g, 69%) as a light yellow solid.

$^1$H NMR (250 MHz, CDCl$_3$) δ(ppm): 7.15 (m, 2H), 6.88 (t, 1H), 6.79 (d, 1H), 4.35 (s, 2H), 2.87 (m, 2H), 2.33 (s, 3H), 2.02 (m, 4H), 1.78 (m, 2H)

Description 4

2,3-Dihydro-1'-methyl-5-nitrospiro[benzofuran-3,4'-piperidine]

2,3-Dihydro-1'-methylspiro[benzofuran-3,4'-piperidine] (D3, 2.72 g, 0.013 mol) was dissolved in acetic anhydride (40 ml) and stirred, standing in a cold water bath, as copper nitrate trihydrate (4.30 g, 0.018 mol) was added portionwise over 1 h. The mixture was stirred for 16 h, poured into $Na_2CO_3$ solution, treated with excess ammonia solution, and extracted with ethyl acetate. The extract was dried ($Na_2SO_4$) and evaporated to give a brown oil, which was purified by chromatography on silica gel, eluting with 0.5% methanol/dichloromethane (gradient), to give the title compound (1.63 g, 79%) as a yellow-brown solid.

$^1$H NMR (200 MNz, CDCl$_3$) δ(ppm): 8.11 (dd, 1H), 8.03 (d, 1H), 6.83 (d, 1H), 4.53 (s, 2H), 2.91 (m, 2H), 2.34 (s, 3H), 2.02 (m, 4H), 1.81 (m, 2H).

Description 5

5-Amino-2,3-dihydro-1'-methylspiro[benzofuran-3,4'-piperidine]

2,3-Dihydro-1'-methyl-5-nitrospiro[benzofuran-3,4'-piperidine] (D4, 0.98 g, 4.0 mmol) was hydrogenated over 10% palladium on charcoal (0.18 g) in ethanol (50 ml) for 6 h. Catalyst was filtered off onto kieselguhr, and the filtrated was evaporated and chromatographed on silica gel, eluting with 0–25% methanol/chloroform (gradient), to give the title compound (0.52 g, 60%) as a cream solid.

$^1$H NMR (250 MHz, d$^6$DMSO) δ(ppm): 6.42 (m, 2H), 6.33 (dd, 1H), 4.22 (s, 2H), 2.84 (d, 2H), 2.29 (s, 3H), 2.12 (t, 2H), 1.82 (td, 2H), 1.61 (d, 2H)

Description 6

6-(Cyanomethyl)-2,3-dihydro-1'-methyl-5-nitrospiro[benzofuran-3,4'-piperidine]

2,3-Dihydro-1'-methyl-5-nitrospiro[benzofuran-3,4'-piperidine] (D4, 0.70 g, 2.8 mmol) and 4-chlorophenoxyacetonitrile (0.90 g, 5.4 mmol) were dissolved in dry DMF (15 ml) and added to potassium t-butoxide (1.60 g, 14.3 mmol). The mixture was stirred under Ar for 6 h, diluted with water (150 ml), acidified (5M HCl) and washed with ethyl acetate. It was then basified (saturated $K_2CO_3$ solution) and extracted with ethyl acetate. This extract was dried ($Na_2SO_4$) and evaporated to give the title compound (0.35 g, 43%) still containing some spirocyclic starting material (ca 30%, NMR).

$^1$H NMR (200 MHz, CDCl$_3$) δ(ppm): 8.05 (s, 1H), 7.07 (s, 1H), 4.56 (s, 2H), 4.19 (s, 2H), 2.9 (m, 2H), 2.34 (s, 3H), 2.1–1.7 (m, 6H).

Description 7

2,3-Dihydro-1'-methylspiro[furo[2,3-f]indole-3,4'-piperidine]

6-(Cyanomethyl)-2,3-dihydro-1'-methyl-5-nitrospiro[benzofuran-3,4'-piperidine] (D6, 0.35 g, 1.2 mmol) was hydrogenated at 50 psiH$_2$ over 10% palladium on charcoal (0.30 g) in a mixture of ethanol (18 ml), water (2 ml) and acetic acid (0.15 ml) for 24 h. Catalyst was filtered off onto kieselguhr, and the filtrate was evaporated to dryness. Chromatography on silica gel, eluting with 0–12% methanol/chloroform (gradient) gave the title compound (0.020 g, 10%) as a pale orange solid.

$^1$H NMR (250 MHz, CDCl$_3$) δ(ppm): 8.70 (b, 1H), 7.18 (m, 2H), 6.99 (s, 1H), 6.43 (m, 1H), 4.40 (s, 2H), 3.05 (m, 2H), 2.46 (s, 3H), 2.3–1.7 (m, 6H).

Description 8

1'-Methyl-2,3,6,7-tetrahydrospiro[furo[2,3-f]indole-3,4'-piperidine]

2,3-Dihydro-1'-methylspiro[furo[2,3-f]indole-3,4'-piperidine] (D7, 0.056 g, 0.23 mmol) was stirred in acetic acid (5 ml) as sodium cyanoborohydride (0.044 g, 0.70 mmol) was added portionwise over 10 min. The solution was stirred for 2 h, diluted with water (20 ml), basified with saturated $K_2CO_3$ solution, and extracted with ethyl acetate. The extract was dried ($Na_2SO_4$) and evaporated to give the title compound (0.030 g, 53%) as a white solid.

$^1$H NMR (200 MHz, CDCl$_3$) δ(ppm): 6.61 (s, 1H), 6.46 (s, 1H), 4.31 (s, 2H), 3.53 (t, 2H), 2.96 (t, 2H), 2.9 (m, 3H), 2.33 (s, 3H), 1.99 (m, 4H), 1.74 (m, 2H).

Description 8 alternative preparation

1'-Methyl-2,3,6,7-tetrahydrospiro[furo[2,3-f]indole-3,4'-piperidine]

(a) A stirred suspension of powdered 1-acetyl-6-bromo-2,3-dihydro-1H-indol-5-ol (Tetrahedron, 1973, 29(8), 1115) (19 g, 0.074 mole) in dry THF (1700 ml) at room temp. under argon was treated with triphenylphosphine (19.6 g, 0.075 mole) and 1-methyl-1,2,3,6-tetrahydropyridine-4-methanol (J. Med. Chem., 1988, 31, 545) (9.5 g, 0.075 mole), followed by the dropwise addition over 15 mins. of a solution of diethyl azodicarboxylate (11.8 ml, 0.075 mole) in THF (40 ml). A mild exotherm occured and the insoluble material dissolved. The solution was warmed at 32° C. for 1 hour, then concentrated in vacuo to approx. 500 ml volume. The solid which had formed was filtered off and dried according 16.1 g of beige solid. The filtrate was concentrated in vacuo and the residue treated with ethyl acetate (700 ml) and 1M HCl acid (500 ml), shaken well and the acid layer separated. This was washed with ethyl acetate, then basified with 40% NaOH and extracted with ethyl acetate, followed by chloroform. The combined extracts were dried ($Na_2SO_4$) and concentrated in vacuo to leave a yellow solid, which was recrystallised from ethyl acetate (3.8 g) giving a total yield of 19.9 g (74%) of 1-acetyl-6-bromo-2,3-dihydro-5-(1-methyl-1,2,3,6-tetrahydropyridin-4-ylmethoxy)-1H-indole.

$^1$H NMR (250 MHz, CDCl$_3$) δ(ppm): 8.42 (s, 1H), 6.72 (s, 1H), 5.80 (br s, 1H), 4.41 (s, 2H), 4.04 (t, 2H), 3.12 (t, 2H), 2.97 (br s, 2H), 2.58 (t, 2H), 2.38 (s, 3H), 2.28 (br s, 2H), 2.18 (s, 3H).

b) A stirred suspension of the product from (a) (20.8 g, 0.057 mole) in benzene (1500 ml) was treated with AIBN (400 mg) and heated to 75° C. under argon, then treated dropwise over 0.5 h with a solution of tributyltin hydride (23 ml, 0.085 mole) in benzene (200 ml). The mixture was heated under reflux for 6 hours, then concentrated in vacuo. The residue was treated with 2M HCl acid (900 ml) and ethyl acetate (600 ml), then shaken well and the acid layer separated, washed with ethyl acetate and then basified with 40% NaOH solution, keeping the temp. below 20° C. A white precipitate was formed which was filtered off, washed with water and dried to afford 14.8 g (91%) of 5-acetyl-1'-methyl-2,3,6,7-tetrahydrospiro[furo[2,3-f]indole-3,4'-piperidine].

$^1$H NMR (250 MHz, CDCl$_3$) δ(ppm): 8.11 (s, 1H), 6.60 (s, 1H), 4.36 (s, 2H), 4.03 (t, 2H), 3.10 (t, 2H), 2.92–2.78 (m, 2H), 2.30 (s, 3H), 2.18 (s, 3H), 2.15–1.90 (m, 4H), 1.80–1.63 (m, 2H).

c) A stirred solution of the product from (b) (14.5 g, 0.051 mole) in a mixture of 5M HCl (250 ml) and ethanol (100 ml) was heated under reflux under argon for 2 hours followed by 16 hours at room temp. The ethanol was removed by concentration in vacuo and the remaining solution cooled in an ice bath and basified to pH 12 by addition of 40% NaOH solution. The white precipitate which formed was filtered off, washed with water and dried to afford 6.0 g of the title compound. The filtrate was extracted with ethyl acetate, followed by chloroform. The combined extract was dried (Na$_2$SO$_4$) and concentrated in vacuo leaving a beige solid (6.2 g) and affording a total of 12.2 g (99%) of title compound (D8).

Description 9
Spiro[2,3-dihydro-1'-methylfuro[2,3-g]quinoline-3,4'-piperidine]

Spiro[5-amino-2,3-dihydro-1'-methyl-1-benzofuran-3,4'-piperidine] (D5, 0.316 g, 1.45 mmol), glycerol (0.20 g, 2.2 mmol) and iodine (0.008 g, 0.03 mmol) were stirred as conc. sulphuric acid (0.23 ml) was added. The dark mixture was then stirred at 180° C. for 1 h. cooled, and partitioned between ethyl acetate and 10% sodium hydroxide solution. After separation, the organic portion was dried (Na$_2$SO$_4$) and evaporated to give the title compound (0.182 g, 49%) as a brown gum.

$^1$H NMR (250 MHz, CDCl$_3$) δ(ppm): 8.62 (dd, 1H), 7.90 (d, 1H), 7.77 (s, 1H), 7.21 (dd, 1H), 6.95 (s, 1H), 4.39 (s, 2H), 2.72 (m, 2H), 2.28 (s, 3H), 2.04 (m, 4H), 1.78 (m, 2H).

Description 10
Spiro[2,3,5,6,7,8-hexahydro-1'-methylfuro[2,3-g]quinoline-3,4'-piperdine]

Spiro[2,3-dihydro-1'-methylfuro[2,3-g]quinoline-3,4'-piperidine] (D9, 0.182 g, 0.72 mmol) and platinum dioxide (0.077 g, 0.34 mmol) were hydrogenated at 50 psiH$_2$ in ethanol (25 ml) for 72 h. Catalyst was filtered off onto kieselguhr, and the filtrate was evaporated to give the title compound (0.151 g, 81%) as a brown gum.

$^1$H NMR (200 MHz, CDCl$_3$) δ(ppm): 6.44 (s, 1H), 6.32 (s, 1H), 4.26 (s, 2H), 3.7–3.1 (b, 1H), 3,24 (t, 2H), 2.82 (m, 2H), 2.73 (t, 2H), 2.31 (s, 3H), 1.94 (m, 6H), 1.73 (m, 2H)

Description 11
2'-Methyl-4'-(5-methyl-1,3,4-oxadiazol-2-yl)biphenyl-4-carboxylic acid A stirred solution of 2-(4-bromo-3-methylphenyl)-5-methyl-1,3,4-oxadiazole (EP 0533268 A1) (0.21 g, 0.0008 mole) in a mixture of DME (10 ml) and water (30 ml) under argon was treated with 4-boronobenzoic acid (0.14 g, 0.0008 mole), sodium carbonate (0.39 g, 0.0037 mole) and tetrakis (triphenylphosphine)palladium (0) (16 mg), then heated under reflux for 4 hours. The mixture was acidified with 1M hydrochloric acid and extracted with ethyl acetate. The extract was dried (Na$_2$SO$_4$) and concentrated in vacuo to leave the title compound as a white solid (0.19 g, 78%).

$^1$H NMR (250 MHz, CDCl$_3$+d$^6$DMSO) δ(ppm): 8.02 (d, 2H), 7.86 (s, 1H), 7.80 (br d, 1H), 7.32 (d, 2H), 7.27 (d, 1H), 2.54 (s, 3H), 2.26 (s, 3H)

Description 12
4-Bromo-3-methylbenzamide oxime

Methanol (20 ml) at 5° C. was treated portionwise over 5 min. with stirring with potassium t-butoxide (1.68 g, 0.015 mole), then after a further 5 mins the solution was treated with hydroxylamine hydrochloride (1.11 g, 0.016 mole). The resulting mixture was allowed to warm to room temperature, stirred for 1 h, then treated with a solution of 4-bromo-3-methylbenzonitrile (2.0 g, 0.010 mole) in methanol (10 ml) and heated under reflux for 3 h. The mixture was allowed to cool, then filtered through kieselguhr and the filtrate concentrated in vacuo to afford the title compound as a white solid (1.56 g, 100%).

$^1$H NMR (250 MHz, d$^6$DMSO) δ(ppm): 7.67 (d, 1H), 7.56 (d, 1H), 7.42 (dd, 1H), 5.85 (br s, 2H), 2.35 (s, 3H).

Description 13
2-(4-Bromo-3-methylphenyl)-5-(dimethylamino)-1,2,4-oxadiazole 4-Bromo-3-methylbenzamide oxime (D12, 1.5 g, 0.0065 mole) was added portionwise over 10 min with stirring to trichloroacetic anhydride (18 ml) at 10° C. under argon. The reaction mixture was allowed to warm up to room temperature and stir for 4 h, then added slowly to a well stirred mixture of excess aqueous sodium bicarbonate solution and ethyl acetate at ice bath temperature. When effervescence had ceased, the ethyl acetate layer was separated, dried (Na$_2$SO$_4$) and concentrated in vacuo to leave the 5-trichloromethyloxadiazole as a pale yellow solid. This was treated with a 33% solution of dimethylamine in IMS (25 ml) and heated under reflux for 18 h, then concentrated in vacuo. The residue was treated with 10% Na$_2$CO$_3$ solution (20 ml) and extracted with ethyl acetate (2×30 ml). The combined extract was dried (Na$_2$SO$_4$), concentrated in vacuo and the residue chromatographed on silica gel eluting with 1:1 ether/60–80 petrol to afford the title compound as a white solid (1.14 g, 62%).

$^1$H NMR (250 MHz, CDCl$_3$) δ(ppm): 7.88 (d, 1H), 7.69 (dd, 1H), 7.58 (d, 1H), 3.20 (s, 6H), 2.44 (s, 3H).

Description 14
2'-Methyl-4'-(5-dimethylamino-1,2,4-oxadiazol-3-yl)biphenyl-4-carboxylic acid The title compound was prepared from 2-(4-bromo-3-methylphenyl)-5-(dimethylamino)-1,2,4-oxadiazole (D13) using a similar procedure to Description 11 (64%) as a white solid.

$^1$H NMR (250 MHz, d$^6$DMSO) δ(ppm): 13.1 (br s, 1H), 8.03 (d, 2H), 7.85 (s, 1H), 7.80 (d, 1H), 7.52 (d, 2H), 7.37 (d, 1H), 3.15 (s, 6H), 2.30 (s, 3H).

Description 15
4'-(5-Methyl-1,2,4-oxadiazol-3-yl)biphenyl-4-carboxylic acid

The title compound was prepared from 1-bromo-4-(5-methyl-1,2,4-oxadiazol-3-yl)benzene [EP 0533268A1] (0.58 g) and 4-boronobenzoic acid (0.4 g) as described in Description 11 as a white solid (0.64 g, 97%).

$^1$H NMR (250 MHz, d$^6$DMSO) δ(ppm): 12.8–13.3 (br s, 1H), 7.8–8.2 (m, 8H), 2.7 (s, 3H).

Description 16
4'-Cyano-2'-methylbiphenyl-4-carboxylic acid 4-bromo-3-methylbenzonitrile (5 g, 0.026 mol) was suspended in 1,2-dimethoxyethane (100 ml) and treated with 4-boronobenzoic acid (2.4 g, 0.026 mol) followed by a solution of sodium carbonate (11.65 g, 0.11 mmol) in water (100 ml). The mixture was flushed with argon and tetrakis (triphenylphosphine)palladium (0) (0.55 g) was added. The reaction mixture was then heated to reflux with stirring. After 24 h, the 1,2-dimethoxyethane was removed by evaporation under reduced pressure and the aqueous residue was washed with ethyl acetate. The aqueous layer was then acidified to pH 1 and the resultant solid was filtered off and was dried in vacuo to give the title compound as a white solid (4.16 g, 69%).

$^1$H NMR (250 MHz, d$^6$DMSO) δ(ppm): 8.02 (d, 2H), 7.82 (s, 1H), 7.40 (dd, 1H), 7.52–7.40 (m, 4H), 2.28 (s, 3H)

Description 17
N-Methoxy-N-methyl-4-bromo-3-methylbenzamide

A stirred suspension of 4-bromo-3-methylbenzoic acid (5.0 g, 0.023 mole) in thionyl chloride (20 ml) was heated under reflux for 2 hours, then concentrated in vacuo. The residual acid chloride was dissolved in dichloromethane (100 ml) and added dropwise over 10 minutes to a stirred solution of N,O-dimethylhydroxylamine hydrochloride (2.4 g, 0.025 mole) and pyridine (5.6 ml, 0.069 mole) in dichloromethane (150 ml) and acetonitrile (20 ml) at −20° C. The reaction mixture was allowed to warm to room temperature over 3 hours then treated with 10% Na$_2$CO$_3$ solution and extracted with dichloromethane. The extract was dried (Na$_2$SO$_4$) and concentrated in vacuo to afford the title compound as a pale yellow oil (5.9 g, 100%).

$^1$H NMR (200 MHz, CDCl$_3$) δ(ppm): 7.60–7.50 (m, 2H), 7.37 (dd, 1H), 3.54 (s, 3H), 3.35 (s, 3H), 2.42 (s, 3H)

Description 18
4-Bromo-3-methylacetophenone

A solution of N-methoxy-N-methyl-4-bromo-3-methylbenzamide (D17) (1.50 g, 0.0057 mole) in dry ether (30 ml) was added dropwise over 10 minutes to a stirred solution of methylmagnesium iodide (0.0075 mole) in dry ether (15 ml) under argon. The mixture was then heated under reflux for 1 hour, allowed to cool and poured into well stirred 1M HCl (50 ml). The mixture was extracted with ethyl acetate and the extract washed with 10% Na$_2$CO$_3$ solution, dried (Na$_2$SO$_4$) and concentrated in vacuo to afford the title compound as a pale yellow oil (1.14 g, 94%).

$^1$H NMR (250 MHz, CDCl$_3$) δ(ppm): 7.81 (s, 1H), 7.62 (s, 2H), 2.57 (s, 3H), 2.45 (s, 3H)

Description 19
4'-Acetyl-2'-methylbiphenyl-4-carboxylic acid

The title compound was prepared from 4-bromo-3-methylacetophenone (D18) using a procedure similar to Description 11 (80%).

$^1$H NMR (250 MHa, CDCl$_3$) δ(ppm): 8.13 (d, 2H), 7.88 (d, 1H), 7.84 (d, 1H), 7.40 (d, 2H), 7.34 (d, 1H), 2.65 (s, 3H), 2.34 (s, 3H).

Description 20
4'-Acetamidomethyl-2'-methylbiphenyl-4-carboxylic acid

4-Bromo-3-methylbenzylamine (EP 532266) (7.36 g, 0.037 mol) was dissolved in 1,2-dimethoxyethane (DME) (180 ml), with stirring, and was treated with 4-boronobenzoic acid (6.14 g, 0.037 mol), followed by a solution of sodium carbonate (17.65 g, 0.167 mol) in water (180 ml). The reaction mixture was then flushed with argon and tetrakis (triphenylphosphine)palladium (O) (1.00 g) was added. The reaction mixture was then heated to reflux under argon. After 16 h, the reaction mixture was allowed to cool and the DME was removed by evaporation under reduced pressure. The aqueous residue was then diluted with water (~200 ml) and washed with EtOAc (2×150 ml). The aqueous layer was then treated with acetic anhydride (6.98 ml, 0.074 mol) and stirred for 1 h at room temperature. The resulting pale brown solution was filtered through kieselguhr to give a pale yellow solution, which was acidified to pH 5 using conc. HCl to give an off white precipitate. This was filtered off, washed with water and dried in vacuo to give the title compound as on off white solid (5.85 g, 56%).

$^1$H NMR (200 MHz, d$^6$DMSO) δ(ppm): 8.45 (t, 1H), 7.95 (d, 2H), 7.32 (d, 2H), 7.15 (m, 3H), 4.28 (d, 2H), 2.20 (s, 3H), 1.90 (s, 3H)

Description 21
Methyl 4'-acetamidomethyl-2'-methylbiphenyl-4-carboxylate

Thionyl chloride (0.119 ml, 1.63 mmol) was added dropwise to MeOH (5 ml) at 0° C., followed by a solution of 4-acetamidomethyl-2'-methylbiphenyl-4-carboxylic acid (D20) (0.345 g, 1.22 mmol) in MeOH (10 ml). The mixture was heated under reflux for 1.5 hr and the solvent removed in vacuo. The residue was dissolved in CH$_2$Cl$_2$ (30 ml) and washed with aq. Na$_2$CO$_3$ followed by water. The organic extract was dried (Na$_2$SO$_4$) and concentrated in vacuo to give a colourless oil, which was purified by column chromatography on silica gel eluting with EtOAc to give a colourless oil that crystallised on standing (0.242 g, 68%).

$^1$H NMR (200 MHz, CDCl$_3$) δ(ppm): 8.1 (d, 2H), 7.38 (d, 2H), 7.23–7.14 (m, 3H), 5.90–5.80 (bs, 1H), 4.45 (d, 2H), 3.90 (s, 3H), 2.28 (s, 3H), 2.05 (s, 3H).

Description 22
7-Methoxy-2,3,4,5-tetrahydro-1H-benzazepine

6-Methoxytetralone (6.86 g, 39 mmol), hydroxylamine hydrochloride (8.15 g, 117 mmol) and sodium acetate trihydrate (25 g, 184 mmol) were stirred at reflux in a mixture of ethanol (200 ml) and water (50 ml) for 45 min, concentrated in vacuo, and diluted with water (200 ml). The white solid (6-methoxytetralone oxide, 7.44 g) was collected and dried. A portion of this (6.31 g, 33 mmol) was stirred in dry THF (150 ml) under argon as lithium aluminium hydride (1.80 g, 47 mmol) was added portionwise. This mixture was stirred at reflux for 3 h, cooled, and treated successively with water (1.5 ml), 10% NaOH (1.5 ml) and water (4.5 ml). The solids were filtered off, and the filtrate was evaporated to give an amber oil. This was chromatographed on silica, eluting with ethyl acetate, giving the title compound (2.96 g, 50%).

$^1$H NMR (250 MHz, CDCl$_3$) δ(ppm): 6.78 (m, 2H), 6.60 (dd, 1H), 3.75 (s, 3H), 3.3 (v broad, 1H), 2.98 (t, 2H), 2.74 (t, 2H), 1.80 (m, 2H), 1.63 (m, 2H).

Description 23
7-Acetoxy-1-acetyl-2,3,4,5-tetrahydro-1H-benzazepine

7-Methoxy-2,3,4,5-tetrahydro-1H-benzazepine (D22, 2.96 g, 17 mmol) was stirred at reflux in 48% HBr for 16 h, cooled and evaporated to dryness, giving a brown solid. This material was stirred in dichloromethane (200 ml) as triethylamine (9.4 ml, 68 mmol) and acetyl chloride (3.6 ml, 51 mmol) were added. The solution was stirred for 1 h, washed with dilute HCl, dried (Na$_2$SO$_4$) and evaporated to give an oil. This was chromatographed on silica, eluting with 0–50% ethyl acetate/dichloromethane, giving the title compound (3.88 g, 94%) as an amber syrup which crystallised on standing.

$^1$H NMR (250 MHz, CDCl$_3$) δ(ppm): 7.14 (d, 1H), 7.0 (m, 2H), 4.69 (dt, 1H), 2.85–2.55 (m, 3H), 2.31 (s, 3H), 2.10–1.75 (m, 3H), 1.88 (s, 3H), 1.44 (m, 1H)

Description 24
1-Acetyl-7-hydroxy-2,3,4,5-tetrahydro-1H-benzazepine

7-Acetoxy-1-acetyl-2,3,4,5-tetrahydro-1H-benzazepine (D23, 3.88 g, 16 mmol) was stirred in ethanol (40 ml) as NaOH (1.26 g, 32 mmol) was added in water (5 ml). After stirring for 30 min, the mixture was diluted with water (500 ml), and acidified with 5M HCl. The tan precipitate was filtered off and dried, yielding 2.02 g (63%) of the title compound. A further 0.80 g (25%) of this material was isolated by dichloromethane extraction of the filtrate.

$^1$H NMR (250 MHz, CDCl$_3$) δ(ppm): 6.98 (d, 1H), 6.83 (bs, 1H), 6.75 (m, 2H), 4.67 (dt, 1H), 2.8–2.5 (m, 3H), 2.05–1.7 (m, 3H), 1.89 (s, 3H), 1.42 (m, 1H)

Description 25
1-Acetyl-8-bromo-7-hydroxy-2,3,4,5-tetrahydro-1H-benzazepine 1-Acetyl-7-hydroxy-2,3,4,5-tetrahydro-1H-benzazepine (D24, 2.81 g, 14 mmol) was stirred in glacial AcOH (50 ml) as N-bromosuccinimide (2.69 g, 15 mmol) was added portionwise over 20 min. The mixture was stirred for 30 min, diluted with ethyl acetate (500 ml), washed with water, K$_2$CO$_3$ solution and brine, dried (Na$_2$SO$_4$) and evaporated to give a tan solid, shown by NMR and TLC to be a mixture of dibromo and mono-bromo isomers. Chromatography on silica, eluting with 0–25% ethyl acetate/dichloromethane, yielded pure title compound (1.22 g, 31%) as a cream solid.

$^1$H NMR (250 MHz, d$^6$DMSO) δ(ppm): 7.43 (s, 1H), 6.84 (s, 1H), 4.43 (dt, 1H), 2.6–2.4 (m, 3H), 1.90 (m, 1H), 1.73 (s, 3H), 1.68 (m, 2H), 1.28 (m, 1H)

Description 26
1-Acetyl-8bromo-7-(1-methyl-1,2,3,6-tetrahydro-4-pyridyl)methoxy-2,3,4,5-tetrahydro-1H-benzazepine The title compound was prepared from 1-acetyl-8-bromo-7-hydroxy-2,3,4,5-tetrahydro-1H-benzazepine (D25) and 4-(hydroxymethyl)-1-methyl-1,2,3,6-tetrahydropyridine (D1) following the procedure of Description 2.

$^1$H NMR (250 MHz, CDCl$_3$) δ(ppm): 7.32 (s, 1H), 6.76 (s, 1H), 5.85 (m, 1H), 4.65 (dt, 1H), 4.51 (s, 2H), 3.02 (m, 2H), 2.8–2.5 (m, 3H), 2.40 (s, 3H), 2.33 (m, 2H), 1.89 (s, 3H), 2.05–1.7 (m, 3H), 1.38 (m, 1H)

Description 27
5-Acetyl-3,4,5,6,7,8,9-hexahydro-1'-methylspiro[2H-furo[2,3-h]benzazepine-3,4'-piperidine]

The title compound was prepared from 1-acetyl-8-bromo-7-(1-methyl-1,2,3,6-tetrahydro-4-pyridyl)methoxy-2,3,4,5-tetrahydro-1H-benzazepine (D26) following the procedure of Description 3.

$^1$H NMR (200 MHz, CDCl$_3$) δ(ppm): 6.84 (s, 1H), 6.64 (s, 1H), 4.65 (dt, 1H), 4.39 (ABq, 2H), 2.84 (m, 2H), 2.64 (m, 3H), 2.33 (s, 3H), 1.83 (s, 3H), 2.1–1.7 (m, 9H), 1.40 (m, 1H)

Description 28
3,5,6,7,8,9-Hexahydro-1'-methylspiro[2H-furo[2,3-h]benzazapine-3,4'-piperidine]

5-Acetyl-3,5,6,7,8,9-hexahydro-1'-methylspiro [2H-furo[2,3-h]benzazepine-3,4'-piperidine] (D27, 0.25 g, 0.82 mmol) was stirred at reflux under Ar in c. HCl (15 ml) for 4 days. It was then evaporated to dryness, dissolved in dichloromethane, washed with K$_2$CO$_3$ solution, dried (Na$_2$SO$_4$) and evaporated to give the title compound (0.203 g) as a brown gum, still containing ca. 15% of amide (NMR). Chromatography on silica, eluting with 0–15% methanol in dichloromethane, give purer material (0.107 g, 49%)

$^1$H NMR (250 MHz, CDCl$_3$) δ(ppm): 6.58 (s, 1H), 6.51 (s, 1H), 4.30 (s, 2H), 3.5 (b, 1H), 2.99 (t, 2H), 2.82 (m, 2H), 2.70 (m, 2H), 2.31 (s, 3H), 1.98 (m, 4H), 1.74 (m, 4H), 1.59 (m, 2H).

Description 29
2'-Methyl-4'-(3-methyl-1,2,4-oxadiazol-5-yl)biphenyl-4-carboxylic acid A stirred solution of 5-(4-bromo-3-methylphenyl)-3-methyl-1,2,4-oxadiazole (EP 0533268 A1) (0.65 g, 0.0026 mole) in a mixture of DME (30 ml) and water (30 ml) under argon was treated with 4-boronobenzoic acid (0.43 g, 0.0026 mole), sodium carbonate (1.16 g, 0.011 mole) and tetrakis (triphenylphosphine)palladium(0) (40 mg), then heated under reflux for 4 hours. The mixture was acidified with 1M hydrochloric acid and extracted with ethyl acetate. The extract was dried (Na$_2$SO$_4$) and concentrated in vacuo to leave the title compound as a white solid (0.61 g, 80%).

$^1$H NMR (250 MHz, d$^6$DMSO) δ(ppm): 8.12–7.95 (m, 4H), 7.60–7.45 (m, 3H), 2.44 (s, 3H), 2.35 (s, 3H).

Description 30
4-Bromo-3-methylbenzoic hydrazide

The title compound was prepared from methyl 4-bromo-3-methylbenzoate using a similar procedure to Description 35, as a white solid (69%).

$^1$H NMR (200 MHz, CDCl$_3$+d$^6$DMSO) δ(ppm): 9.05 (br s, 1H), 7.75 (d, 1H), 7.58 (d, 1H), 7.50 (dd, 1H), 4.10 (br s, 2H), 2.42 (s, 3H)

Description 31
2-(4-Bromo-3-methylphenyl)-5-ethyl-1,3,4-oxadiazole

The title compound was afforded as a beige crystalline solid (1.65 g) as per method of Description 35, using 4-bromo-3-methylbenzoic hydrazide (D31) (1.30 g) and triethyl orthopropionate (13.0 ml).

$^1$H NMR (200 MHz, CDCl$_3$) δ(ppm): 7.91 (s, 1H), 7.68 (m, 2H), 2.96 (q, 2H), 2.49 (s, 3H), 1.45 (t, 3H).

Description 32
4'-(5-ethyl-1,3,4-oxadiazol-2-yl)-2'-methylbiphenyl-4-carboxylic acid The title compound was afforded as a white solid (82%) as per method of Description 11 from 2-(4-bromo-3-methylphenyl)-5-ethyl-1,3,4-oxadiazole (D31).

$^1$H NMR (400 MHz, d$^6$DMSO) δ(ppm): 12.98 (s, 1H), 8.00 (d, 2H), 7.89 (s, 1H), 7.82 (d, 1H), 7.48 (d, 2H), 7.38 (d, 1H), 2.90 (q, 2H), 2.28 (s, 3H), 1.29 (t, 3H).

Description 33
4-Borono-3-methylbenzoic acid

A stirred solution of 4-bromo-3-methylbenzoic acid (5.0 g, 0.02 mole) in dry THF (250 ml) at −78° C. under argon was treated with 1.6M n-butyllithium in hexane (36.3 ml, 0.05 mole). The mixture changed from a clear solution to an orange suspension. This was stirred at −78° C. for 0.25 h, then treated with triisopropyl borate (13.4 ml, 0.05 mole) and stirred at −78° C. for a further 1 h. The mixture was allowed to warm to room temp. and stir for 19 h, then treated with water (25 ml) and concentrated in vacuo. The residue was chromatographed on silica gel eluting with 10% methanol/dichloromethane to afford the title compound as a white solid (2.63 g, 67%).

$^1$H NMR (200 MHz, d$^6$DMSO) δ(ppm): 7.72–7.63 (m, 2H), 7.50 (d, 1H), 2.43 (s, 3H).

Description 34
2,2'-Dimethyl-4'-(5-methyl-1,3,4-oxadiazol-2-yl)biphenyl-4-carboxylic acid The title compound was prepared from 2-(4-bromo-3-methylphenyl)-5-methyl-1,3,4-oxadiazole (EP 0533268 A1) and 4-borono-3-methylbenzoic acid (D33) using a similar procedure to Description 11 as a white solid (31%).

$^1$H NMR (250 MHz, CDCl$_3$) δ(ppm): 8.10–7.97 (m, 3H), 7.92 (dd, 1H), 7.24 (d, 2H), 2.66 (s, 3H), 2.13 (s, 6H).

Description 35
2-(4-Bromo-2-methylphenyl)-5-methyl-1,3,4-oxadiazole

A stirred solution of methyl 4-bromo-2-methylbenzoate (0.9 g, 3.9 mmole) in methanol (10 ml) was treated with hydrazine hydrate (1.0 ml, 21 mmole) and heated under reflux for 66 h. The solution was concentrated in vacuo to leave the hydrazide as a white solid. This was treated with triethyl orthoacetate (10 ml) and heated under reflux under argon for 4 h, then concentrated in vacuo. The residue was chromatographed on silica gel eluting with 1:1 ether/60–80 petrol to afford the title compound as a white solid (0.77 g, 78%).

$^1$H NMR (250 MHz, CDCl$_3$) δ(ppm): 7.76 (d, 1H), 7.51 (s, 1H), 7.45 (dd, 1H), 2.68 (s, 3H), 2.62 (s, 3H).

Description 36
2,3'-Dimethyl-4'-(5-methyl-1,3,4-oxadiazol-2-yl)biphenyl-4-carboxylic acid The title compound was prepared from 2-(4-bromo-2-methylphenyl)-5-methyl-1,3,4-oxadiazole (D35) and 4-borono-3-methylbenzoic acid (D33) using a similar procedure to Description 11 as a white solid (24%).

$^1$H NMR (250 MHz, CDCl$_3$+d$^6$DMSO) δ(ppm): 7.95–7.80 (m, 3H), 7.30–7.20 (m, 3H), 2.68 (s, 3H), 2.59 (s, 3H), 2.26 (s, 3H).

Description 37
4-Bromo-3-methyl benzamide

4-Bromo-3-methylbenzoic acid (19 g, 0.088 mole) was dissolved in dichloromethane (200 ml) and treated with oxalyl chloride (12 ml, 0.013 mole), followed by DMF (3 drops). The reaction mixture was stirred for 18 h at room temperature, after which the solvent was removed in vacuo. The acid chloride was added dropwise to 0.88 ammonia solution (250 ml) with stirring. The resulting solid was filtered off, washed with ether and dried to afford the title compound (18.03 g, 96%).

$^1$H NMR (200 MHz, d$^6$DMSO) δ(ppm): 8.02 (s, 1H), 7.88 (s, 1H), 7.69–7.61 (m, 2H), 7.44 (s, 1H), 2.40 (s, 3H)

Description 38
4-Bromo-3-methylthiobenzamide

4-Bromo-3-methylbenzamide (D37, 1.0 g, 0.0047 mole) was dissolved in THF (50 ml), treated with Lawessons reagent (0.95 g, 0.0024 mole) and stirred under argon for 4 h. The solvent was removed in vacuo and the residue purified by flash chromatography on silica gel eluting with 10% EtOH/CHCl$_3$ to afford the title compound as a yellow solid (0.87 g, 80%).

$^1$H NMR (200 MHz, CDCl$_3$) δ(ppm): 7.78 (s, 1H), 7.72 (br s, 1H), 7.63–7.45 (m, 2H), 7.19 (br s, 1H), 2.45 (s, 3H).

Description 39
2-(4-Bromo-3-methylphenyl)-4-methylthioazole

4-Bromo-3-methylthiobenzamide (D38, 0.87 g, 0.0038 mole) was dissolved in ethanol (60 ml) and treated with chloroacetone (0.39 ml, 0.0049 mole). The reaction mixtures was heated under reflux for 5 h, then more chloroacetone (0.39 ml, 0.0049 mole) was added and the mixture heated under reflux for a further 3 h. After cooling to room temperature, the solvent was removed in vacuo to leave the title compound as a pale oil (1.00 g, 98%).

$^1$H NMR (200 MHz, CDCl$_3$) δ(ppm): 8.20 (d, 1H), 7.95 (dd, 1H), 7.69 (d, 1H), 7.22 (s, 1H), 2.76 (s, 3H), 2.50 (s, 3H).

Description 40
2'-Methyl-4'-(4-methylthiazol-2-yl)biphenyl-4-carboxylic acid The title compound was prepared from 2-(4-bromo-3-methylphenyl)-4-methylthiazole (D39, 1.00 g, 0.0037 mole) using the method of Description 11 (0.77 g, 67%).

$^1$H NMR (200 MHz, d$^6$DMSO) δ(ppm): 8.03 (d, 2H), 7.89 (s, 1H), 7.82 (dd, 1H), 7.52 (d, 2H), 7.40–7.22 (m, 2H), 2.46 (s, 3H), 2.32 (s, 3H).

Description 41
4'-Methoxycarbonyl-2'-methylbiphenyl-4-carboxylic acid

A stirred solution of methyl 4-bromo-3-methylbenzoate (EP 0533268 A1) (1.0 g, 0.0044 mole) in dry DMF (10 ml) under argon was treated with 4-boronobenzoic acid (0.73 g, 0.0044 mole) and tetrakis (triphenylphosphine) palladium (0) (80 mg), followed by triethylamine (1.8 ml, 0.016 mole), the mixture was heated at 100° C. for 18 hours, then concentrated in vacuo. The residue was treated with ethyl acetate and extracted with 10% NaHCO$_3$ solution. The basic extract was acidified with dil. HCl and extracted with ethyl acetate. The extract was dried (Na$_2$SO$_4$) and concentrated in vacuo to afford the title compound as a white solid (0.46 g, 39%).

$^1$H NMR (250 MHz, d$^6$DMSO) δ(ppm): 13.1 (brs, 1H), 8.04 (d, 2H), 7.92 (s, 1H), 7.87 (d, 1H), 7.51 (d, 2H), 7.38 (d, 1H), 3.87 (s, 3H), 2.30 (s, 3H).

Description 42
5'-Methoxycarbonyl-2'-methylbiphenyl-4-carboxylic acid

A stirred solution of methyl 3-bromo-4-methylbenzoate (2.6 g, 0.011 mole) in dry DMF (20 ml) under argon was treated with 4-boronobenzoic acid (1.85 g, 0.011 mole) and tetrakis (triphenylphosphine) palladium(0) (400 mg), followed by triethylamine (4.68 ml, 0.046 mole). The mixture was heated at 100° C. for 18 hours, then concentrated in vacuo. The residue was treated with ethyl acetate and extracted with 10% NaHCO$_3$ solution. The basic extract was acidified with dil. HCl and extracted with ethyl acetate. The extract was dried (Na$_2$SO$_4$) and concentrated in vacuo to afford the title compound as a light orange solid (2.12 g, 85%).

$^1$H NMR (250 MHz, d$^6$DMSO) δ(ppm): 13.1 (br s, 1H), 8.09–8.00 (m, 2H), 7.92–7.75 (m, 2H), 7.68–7.43 (m, 3H), 3.88 (s, 3H), 2.30 (s, 3H)

Description 43
N-[4-Bromo-3-methylphenyl]-methanesulphonamide

To a stirred solution of 4-bromo-3-methylaniline (3.32 g, 17.8 mmol) in dry dichloromethane (150 ml) was added triethylamine (4.96 ml, 35.6 mmol), followed by methanesulphonyl chloride (1.52 ml, 19.6 mmol). The complete reaction mixture was stirred at room temperature under Ar for 18 hours. The mixture was then washed with water, saturated potassium carbonate solution, and finally brine. The organic layer was dried (Na$_2$SO$_4$) and concentrate din vacuo to afford a creamy orange solid. This was dissolved in dichloromethane and shaken with 10% sodium hydroxide solution. The aqueous layer was separated and acidified to pH 6 using concentrated hydrochloric acid. This solution was then extracted using chloroform. The combined organic layers were dried (Na$_2$SO$_4$) and concentrated in vacuo to afford the title compound as a white solid (1.35 g, 30%).

$^1$H NMR (250 MHz, CDCl$_3$) δ(ppm): 7.60–6.50 (vb, 1H), 7.61 (d, 1H), 7.50 (d, 1H), 6.95 (dd, 1H), 3.12 (s, 3H), 2.40 (s, 3H)

Description 44

4'-(Methanesulphonamine)-2'-methylbiphenyl-4-carboxylic acid

The title compound (44%) was afforded as a white solid as per method of Description 11 from N-[4-bromo-3-methylphenyl]-methanesulphonamide (D43).

$^1$H NMR (200 MHz, d$^6$DMSO) δ(ppm): 13.0 (b, 1H), 9.80 (s, 1H), 7.98 (d, 2H), 7.43 (d, 2H), 7.15 (m, 3H), 3.00 (s, 3H), 2.20 (s, 3H)

Description 45

2'-Methyl-5'-(5-methyl-1,3,4-oxadiazol-2-yl)biphenyl-4-carboxylic acid

The title compound was prepared from methyl 3-bromo-4-methylbenzoate following similar procedures to those in Descriptions 35 and 11 as a beige solid.

$^1$H NMR (200 MHz, d$^6$DMSO) δ(ppm): 11.70 (s, 1H), 8.10–7.50 (m, 7H), 2.30 (s, 3H), 1.90 (s, 3H).

Description 46

N-[4-Bromo-3-methylphenyl]-acetamide

A stirred solution of 4-bromo-3-methylaniline (3.0 g, 0.016 mole) and triethylamine (4.5 ml, 0.032 mole) in dichloromethane (30 ml) at 0° C. was treated with acetyl chloride (1.2 ml, 0.017 mole) and allowed to warm to room temperature over 1 h. The mixture was washed with water, then 5M HCl acid and dried (Na$_2$SO$_4$), then concentrated in vacuo to afford the title compound as a pale yellow solid (3.07 g, 83%).

$^1$H NMR (200 MHz, CDCl$_3$) δ(ppm): 7.50–7.35 (m, 2H), 7.19 (dd, 1H), 2.36 (s, 3H), 2.16 (s, 3H).

Description 47

4'-Acetamido-2'-methylbiphenyl-4-carboxylic acid

The title compound was prepared from N-[4-bromo-3-methylphenyl]-acetamide (D46) using a similar procedure to Description 11 as a white solid (66%).

$^1$H NMR (200 MHz, d$^6$DMSO) δ(ppm): 12.8 (br s, 1H), 9.98 (s, 1H), 7.98 (d, 2H), 7.55–7.40 (m, 4H), 7.16 (d, 1H), 2.20 s, 3H), 2.05 (s, 3H)

Description 48

Bis-(2,3-dihydro-6-iodo-1H-indol-5-yl) disulphide

A stirred suspension of 2,3-dihydro-6-iodo-1H-indole (0.600 g, 2.45 mmol) (Heterocycles 1987 26(11)2817) in methanol (10 ml) under argon, was treated with potassium thiocyanate (0.467 g, 4.90 mmol) with stirring at 0° C. A solution of bromine (0.138 ml, 2.69 mmol) in methanol (5 ml) was then added slowly. After 16 hours the reaction mixture was evaporated under reduced pressure. The residue was partitioned between dichloromethane and potassium carbonate solution and the aqueous layer was extracted with dichloromethane. The combined organic layers were then dried (Na$_2$SO$_4$) and evaporated under reduced pressure to give a brown solid which was suspended in a mixture of 880 ammonia solution (18 ml) and dioxan (12 ml) and was heated to gentle reflux in air. After 24 h, the reaction mixture was allowed to cool and was partitioned between dichloromethane and water. The aqueous layer was then extracted with dichloromethane (1X) and the combined organic layers were dried (Na$_2$SO$_4$) and evaporated under reduced pressure to give the title compound as an orange oil which was dried in vacuo (0.410 g, 61%).

$^1$H NMR (200 MHz, CDCl$_3$) δ: 7.42 (s, 1H), 7.30 (s, 1H), 7.07 (s, 1H), 7.05 (s, 1H), 3.62 (t, 2H), 3.55 (t, 2H), 3.05 (t, 2H), 2.95 (t, 2H).

Description 49

1-Acetyl-2,3-dihydro-6-iodo-1H-indol-5-thiol

Bis-(2,3-dihydro-6-iodo-1H-indol-5-yl) disulphide (D48) (0.408 g, 0.739 mmol) was suspended in dichloromethane (30 ml) and was treated with triethylamine (0.226 ml, 1.62 mmol) at 0° C., followed by acetic anhydride (0.153 ml, 1.62 mmol) with stirring under argon. After 24 h the reaction mixture was washed with water (2X). The organic layer was then dried (Na$_2$SO$_4$) and was evaporated under reduced pressure to give an organ oil that was dried in vacuo (0.40 g). The oil was then redissolved in a mixture of dioxan (20 ml) and water (4 ml) and triphenylphosphine (0.250 g, 0.953 mmol) was added, followed by conc. HCl (1 drop). The mixture was flushed with argon, and then heated to reflux with stirring. After 2.5 hours, the reaction mixture was allowed to cool and was partitioned between 2% sodium hydroxide (20 ml) and dichloromethane (30 ml). The organic layer was then washed with 2% sodium hydroxide (10 ml) and the combined aqueous layers were acidified to pH 5 using conc. HCl. The resultant suspension was then extracted with dichloromethane (3×15 ml). The combined extracts were then dried (Na$_2$SO$_4$) and evaporated under reduced pressure to give the title compound as a yellow solid which was dried in vacuo (0.354 g, 75%).

$^1$H NMR (200 MHz, CDCl$_3$) δ: 8.63 (s, 1H), 7.20 (s, 1H), 4.05 (t, 2H), 3.12 (t, 2H), 2.20 (s, 3H).

Description 50

1-Acetyl-2,3-dihydro-6-iodo-5-(pyridin-4-ylmethylthio)-1H-indole

1-Acetyl-2,3-dihydro-6-iodo-1H-indol-5-thiol (D49) (0.346 g, 1.08 mmol) in dry DMF (5 ml) was treated with potassium carbonate (0.374 g, 3.71 mmol) followed by picolyl chloride hydrochloride (0.186 g, 1.13 mmol). After 65 h stirring at room temp. the reaction mixture was evaporated under reduced pressure and was partitioned between dichloromethane and water. The aqueous layer was then extracted with dichloromethane and the combined organic layers were then dried (Na$_2$SO$_4$) and evaporated under reduced pressure to give the title compound as a pale brown solid which was dried in vacuo (0.392 g, 89%).

$^1$H NMR (200 MHz, CDCl$_3$) δ: 8.72 (s, 1H), 8.48 (d, 2H), 7.12 (d, 2H), 6.97 (s, 1H), 4.05 (t, 2H), 3.95 (s, 2H), 3.03 (t, 2H), 2.21 (s, 3H).

Description 51

1-Acetyl-2,3-dihydro-6-iodo-5-[(1-methyl-1,2,3,6-tetrahydropyridin-4-yl)methylthio]-1H-indole 1-Acetyl-2,3-dihydro-6-iodo-5-(pyridin-4-ylmethylthio)-1H-indole (D50) (0.390 g, 0.951 mmol) was dissolved in dry DMF (5 ml) and was treated with methyl iodide (0.089 ml, 1.430 mmol) with stirring. After 24 hours the reaction mixture was evaporated under reduced pressure and was triturated with ethyl acetate (~20 ml). The resultant brown solid was then filtered off, washed with diethyl ether and dried in vacuo (0.513 g). The solid was then redissolved in a mixture of ethanol (20 ml) and water (10 ml) and was cooled to 0° C. Sodium borohydride (0.069 g, 1.824 mmol) was then added. After 0.5 h a further amount of sodium borohydride (0.035 g, 0.912 mmol) was added. The reaction mixture was then allowed to warm to room temperature.

After 1.5 hours the reaction mixture was treated with sodium bicarbonate solution (~15 ml) and was partitioned between dichloromethane and water. The aqueous layer was then extracted with dichloromethane (1X) and the combined organic layers were dried (Na$_2$SO$_4$) and evaporated under reduced pressure to give a yellow solid which was purified by silica-gel chromatography (5% MeOH/CH$_2$Cl$_2$ as eluant) to give the title compound as an off white solid (0.208 g, 53%).

$^1$H NMR (200 MHz, CDCl$_3$) δ: 8.70 (s, 1H), 7.12 (s, 1H), 5.48 (s, 1H), 4.08 (t, 2H), 3.45 (s, 2H), 3.12 (t, 2H), 2.89 (s, 2H), 2.55 (t, 2H), 2.30 (s, 5H), 2.20 (s, 3H)

Description 52
5-Acetyl-1'-methyl-2,3,6,7-tetrahydrospiro[thiopheno[2,3-f]indole-3,4'-piperidine]

A solution of tributyltin hydride (0.251 ml, 0.934 mmol) in benzene (10 ml) was added dropwise over 30 minutes to a stirred solution of 1-acetyl-2,3-dihydro-6-iodo-5-[(1-methyl-1,2,3,6-tetrahydropyridin-4-yl)methylthio]-1H-indole (D51) (0.200 g, 0.467 mmol) and AIBN (5 mg) in benzene (20 ml) under argon at reflux. Reflux was continued for a further 0.75 h. The reaction mixture was then allowed to cool. Ethyl acetate (10 ml) was then added and the mixture washed with 2.5M HCl (3×10 ml). The combined aqueous washings were then basified with solid potassium carbonate and the resultant suspension was extracted with dichloromethane (3×15 ml). The combined organic extracts were then dried (Na$_2$SO$_4$) and evaporated under reduced pressure to give a pale yellow solid which was dried in vacuo (0.127 g). The solid was purified by prep. TLC (15% MeOH/CH$_2$Cl$_2$ as eluant) to give the title compound as a cream solid (0.047 g, 33%).

$^1$H NMR (250 MHz, CDCl$_3$) δ: 8.12 (s, 1H), 6.98 (s, 1H), 4.05 (t, 2H), 3.30 (s, 2H), 3.12 (t, 2H), 2.89 (m, 2H), 2.38 (s, 3H), 2.30 (m, 2H), 2.20 (s, 3H), 2.05 (m, 2H), 1.85 (m, 2H).

Description 53
1'-Methyl-2,3,6,7-tetrahydrospiro[thiopheno[2,3-f]indole-3,4'-piperidine]

5-Acetyl-1'-methyl-2,3,6,7-tetrahydrospiro[thiopheno[2,3-f]indole-3,4'-piperidine] (D52) (0.047 g, 0.156 mmol) was dissolved in a mixture of ethanol (2 ml) and 5M HCl (4 ml) and was heated to reflux with stirring under argon. After 3 h, the reaction mixture was allowed to cool, was diluted with water (10 ml) and was basified using solid potassium carbonate. The resulting suspension (pH 9 ) was then extracted with dichloromethane (3×10 ml) and the combined extracts were dried (Na$_2$SO$_4$) and evaporated under reduced pressure to give the title compound as an off white solid, which was dried in vacuo (0.029 g, 71%).

$^1$H NMR (250 MHz, CDCl$_3$) δ: 7.29 (s, 1H), 6.50 (s, 1H), 3.53 (t, 2H), 3.28 (s, 2H), 2.95 (t, 2H), 2.82 (m, 2H), 2.31 (s, 3H), 2.10 (m, 2H), 1.87 (m, 4H).

Description 54
Methyl 4'-[(N-methanesulphonyl-N-methyl)amino]-2'-methylbiphenyl-4-carboxylate 4'-(Methanesulphonamino)-2'-methylbiphenyl-4-carboxylic acid (D44, 0.29 g, 0.94 mmol), anhydrous K$_2$CO$_3$ (0.40 g, 2.9 mmol) and iodomethane (0.18 ml, 2.9 mmol) were stirred in dry DMF (5 ml) for 16 h. The mixture was diluted with ethyl acetate, washed with water and brine, dried (Na$_2$SO$_4$) and evaporated to give the title compound (0.32 g, quantitative) as a brown oil, containing residual solvent (NMR).

$^1$H NMR (250 MHz, CDCl$_3$) δ(ppm): 8.10 (d, 2H), 7.38 (d, 2H), 7.27 (m, 3H), 3.96 (s, 3H), 3.37 (s, 3H), 2.91 (s, 3H), 2.28 (s, 3H).

Description 55
4-Bromo-N,N-dimethylbenzenesulphonamide

4-Bromobenzenesulphonyl chloride (4.48 g, 18 mmol) was stirred in dichloromethane, and dimethylamine (40% aqueous solution, 10 ml) was added portionwise. The mixture was stirred for 2 h, washed with dilute hydrochloric acid, dried (Na$_2$SO$_4$) and evaporated to give the title compound (4.38 g, 94%) as a white solid.

$^1$H NMR (250 MHz, CDCl$_3$) δ(ppm): 7.67 (Abq. 4H), 2.72 (s, 6H).

Description 56
4'-(Dimethylaminosulphonyl)biphenyl-4-carboxylic acid

This was prepared from 4-bromo-N,N-dimethylbenzenesulphonamide (D55) following the procedure of Description 11. This gave the title compound as a white solid (85%).

$^1$H NMR (200 MHz, d$^6$DMSO) δ(ppm): 8.08 (d, 2H), 8.02 (d, 2H), 7.90 (d, 2H), 7.86 (d, 2H), 2.66 (s, 6H).

Description 57
4'-(Methanesulphonyl)biphenyl-4-carboxylic acid

This was prepared from 4-bromophenyl methyl sulphone, following the procedure of Description 11. This gave the title compound (72%) as a white solid.

$^1$H NMR (250 MHz, d$^6$DMSO) δ(ppm): 8.05 (m, 6H), 7.88 (d, 2H), 3.28 (s, 3H).

Description 58
N'-(4-Bromo-3-methylphenyl)-N,N-dimethylurea

4-Bromo-3-methylaniline (5.00 g, 27 mmol), triethylamine (3.9 ml, 28 mmol), 4-(dimethylamino)pyridine (0.5 g, 4 mmol) and dimethylcarbamyl chloride (2.6 ml, 28 mmol) were mixed in dichloromethane (100 ml), and left to stand for 2 weeks. The solution was then washed with dilute hydrochloric acid, dried (Na$_2$SO$_4$) and evaporated to give a solid. This was triturated with ether, and the solid was filtered off and dried, affording the title compound (2.51 g, 36%) as an off-white solid.

$^1$H NMR (250 MHz, CDCl$_3$) δ(ppm): 7.40 (d, 1H), 7.35 (d, 1H), 7.07 (dd, 1H), 6.78 (bs, 1H), 3.02 (s, 6H), 2.36 (s, 3H).

Description 59
4'-(N,N-Dimethylcarbamoylamino)-2'-methylbiphenyl-4-carboxylic acid This was prepared from N'-(4-bromo-3-methylphenyl)-N,N-dimethylurea (D58), following the procedure of Description 11. This gave the title compound as a salmon-coloured solid (90%).

$^1$H NMR (250 MHz, d$^6$DMSO) δ(ppm): 8.34 (s, 1H), 7.98 (d, 2H), 7.45 (m, 4H), 7.10 (d, 1H), 2.93 (s, 6H), 2.22 (s, 3H).

Description 60
Ethyl N-(4-bromo-3-methylphenyl)carbamate

4-Bromo-3-methylaniline (5.00 g, 27 mmol) and triethylamine (4.5 ml, 32 mmol) were stirred in dichloromethane (200 ml) as ethyl chloroformate (3.1 ml, 32 mmol) was added dropwise. The mixture was stirred for 2 h, when water was added. After stirring for a further 15 min, the white precipitate was filtered off, and the filtrate was separated. The organic portion was dried (Na$_2$SO$_4$) and evaporated to give the title compound (2.57 g, 37%) as an orange-brown oil.

$^1$H NMR (250 MHz, CDCl$_3$) δ(ppm): 7.42 (d, 1H), 7.30 (d, 1H), 7.09 (dd, 1H), 6.60 (b s, 1H), 4.23 (q, 2H), 2.36 (s, 3H), 1.32 (t, 3H).

Description 61
4'-(Ethoxycarbonylamino)-2'-methylbiphenyl-4-carboxylic acid

This was prepared from ethyl N-(4-bromo-3-methylphenyl)carbamate (D60), following the procedure of Description 11. This gave the title compound, after recrystallization from ethyl acetate/petroleum ether (bp. 60–80° C.), as a white powder (63%).

$^1$H NMR (200 MHz, d$^6$DMSO) δ(ppm): 9.70 (s, 1H), 7.98 (d, 2H), 7.4 (m, 4H), 7.16 (d, 1H), 4.14 (q, 2H), 2.22 (s, 3H), 1.26 (t, 3H)

Description 62
3-(4-Bromo-3-methylphenyl)-5-methyl-1,2,4-triazole

4-Bromo-3-methylbenzoic hydrazide (D30, 3.06 g, 13 mmol), ethyl acetimidate hydrochloride (2.48 g, 20 mmol) and triethylamine (5.6 ml, 40 mmol) were stirred at reflux under Ar for 24 h, and then evaporated to dryness. The residue was chromatographed on silica gel, eluting with dichloromethane/ethanol/ammonia (300:8:1). This gave the title compound (1.95 g, 58%) as a white solid.

$^1$H NMR (200 MHz, CDCl$_3$/d$^6$DMSO) δ(ppm): 7.63 (s, 1H), 7.41 (d, 1H), 7.22 (d, 1H), 2.15 (s, 3H), 2.10 (s, 3H).

Description 63
3-(4-Bromo-3-methylphenyl)-4,5-dimethyl-1,2,4-triazole 3-(4-Bromo-3-methylphenyl)-5-methyl-1,2,4-triazole (D62, 0.60 g, 2.4 mmol) was stirred under Ar in dry DMF (6 ml) as sodium hydride (80% dispersion, 0.21 g, 7.2 mmol) was added. After stirring for 30 min, iodomethane (0.3 ml, 4.8 mmol) was added. This mixture was stirred for 1 h, and treated with water (30 ml), giving a beige precipitate. This was filtered off and dried, giving the title compound (0.49 g, 77%) as a beige solid. $^1$H NMR (250 MHz, d$^6$DMSO) δ(ppm): 7.92 (s, 1H), 7.65 (m, 2H), 3.80 (s, 3H), 2.44 (s, 3H), 2.39 (s, 3H).

Description 64
4'-(4,5-Dimethyl-1,2,4-triazol-3-yl)-2'-methylbiphenyl-4-carboxylic acid This was prepared from 3-(4-bromo-3-methylphenyl)-4,5-dimethyl-1,2,4-triazole (D63), following the procedure of Description 11. This gave the title compound (53%) as a white solid.

$^1$H NMR (200 MHz, d$^6$DMSO) δ(ppm): 13.0 (v b, 1H), 8.02 (d, 2H), 7.93 (s, 1H), 7.87 (d, 1H), 7.53 (d, 2H), 7.30 (d, 1H), 3.84 (s, 3H), 2.46 (s, 3H), 2.30 (s, 3H).

Description 65
2-(4-Pyridyl)ethanol

This was prepared from ethyl 4-pyridylacetate, following the procedure of Description 1. This gave the title compound (95%) as a yellow oil.

$^1$H NMR (200 MHz, CDCl$_3$) δ(ppm): 8.43 (d, 2H), 7.17 (d, 2H), 3.90 (t, 2H), 3.0 (b, 1H), 2.86 (t, 2H).

Description 66
1-Acetyl-6-bromo-2,3-dihydro-5-[2-(4-pyridyl)ethoxy]-1H-indole This was prepared from 1-acetyl-6-bromo-2,3-dihydro-1H-indol-5-ol (*Tetrahedron* 1973, 29(8), 1115) and 2-(4-pyridyl)ethanol (D65), following the procedure of Description 8a. This gave the title compound (84%), as a yellow solid.

$^1$H NMR (200 MHz, CDCl$_3$) δ(ppm): 8.54 (d, 2H), 8.45 (s, 1H), 7.25 (d, 2H), 6.70 (s, 1H), 4.19 (t, 2H), 4.05 (t, 2H), 3.12 (m, 4H), 2.19 (s, 3H).

Description 67
1-Acetyl-6-bromo-2,3-dihydro-5-[2-(4-pyridyl)ethoxy]-1H-indole methiodide 1-Acetyl-6-bromo-2,3-dihydro-5-[2-(4-pyridyl)ethoxy]-1H-indole (D66) (3.15 g, 8.7 mmol) and iodomethane (1.1 ml, 17.7 mmol) were mixed in dry DMF (30 ml) and left to stand for 16 h. The suspension was then diluted with ethyl acetate (300 ml), and the solid was collected and dried, affording the title compound (2.78 g, 63%) as a yellow powder.

$^1$H NMR (200 MHz, d$^6$DMSO) δ(ppm): 8.93 (d, 2H), 8.19 (s, 1H), 8.14 (d, 2H), 7.13 (s, 1H), 4.38 (t, 2H), 4.31 (s, 3H), 4.10 (t, 2H), 3.37 (t, 2H), 3.12 (t, 2H), 2.15 (s, 3H).

Description 68
1-Acetyl-6-bromo-2,3-dihydro-5-[2-(1-methyl-1,2,3,6-tetrahydro-4-pyridyl)ethoxy]-1H-indole 1-Acetyl-6-bromo-2,3-dihydro-5-[2-(4-pyridyl)ethoxy]-1H-indole methiodide (D67) (2.78 g, 5.5 mmol) was dissolved in ethanol (40 ml) and water (40 ml), cooled in ice, and treated with stirring with sodium borohydride (0.31 g, 8.2 mmol) portionwise over 1 h. The mixture was then basified with sodium hydroxide solution, diluted with water (100 ml), and extracted with chloroform. The extract was dried (Na$_2$SO$_4$) and evaporated to yield the title compound (1.95 g, 96%) as a brown solid.

$^1$H NMR (200 MHz, CDCl$_3$) δ(ppm): 8.43 (s, 1H), 6.72 (s, 1H), 5.53 (m, 1H), 4.05 (m, 4H), 3.14 (t, 2H), 2.92 (m, 2H), 2.55 (m, 4H), 2.35 (s, 3H), 2.25 (m, 2H), 2.20 (s, 3H).

Description 69
6-Acetyl-1'-methyl-2,3,7,8-tetrahydrospiro[4H-pyrano[2,3-f]indole-4,4'-piperidine]

This was prepared from 1-acetyl-6-bromo-2,3-dihydro-5-[2-(1-methyl-1,2,3,6-tetrahydro-4-pyridyl)ethoxy]-1H-indole (D68), following the procedure of Description 8b. This gave, after extensive purification, the title compound as a brown oil.

$^1$H NMR (200 MHz, CDCl$_3$) δ(ppm): 7.96 (s, 1H), 6.86 (s, 1H), 4.40 (dt, 1H), 4.07 (t, 2H), 3.6 (m, 3H), 3.17 (t, 2H), 3.0 (m, 1H), 2.80 (s, 3H), 2.7 (m, 2H), 2.23 (s, 3H), 1.95 (m, 5H).

Description 70
1'-Methyl-2,3,7,8-tetrahydrospiro[4H-pyrano[2,3-f]indole-4,4'-piperidine]

This was prepared from 6-acetyl-1'-methyl-2,3,7,8-tetrahydrospiro[4H-pyrano[2,3-f]indole-4,4'-piperidine] (D69), following the procedure of Description 8c. This gave the title compound (70%) as a brown oil.

$^1$H NMR (250 MHz, CDCl$_3$) δ(ppm): 6.79 (s, 1H), 6.48 (s, 1H), 4.30 (dt, 1H), 3.55 (m, 3H), 3.11 (m, 1H), 2.99 (t, 2H), 2.89 (m, 1H), 2.37 (s, 3H), 2.2 (m, 2H), 1.7–2.0 (m, 4H), 1.57 (m, 1H), 1.34 (m, 1H), 0.85 (m, 1H).

Description 71
N'-Acetyl 4-bromo-3-methylbenzoic hydrazide

4-Bromo-3-methylbenzoic hydrazide (D30, 7.5 g) was suspended in acetic anhydride (7 ml) giving rise to an exothermic reaction. The reaction mixture was cooled to room temperature and the product collected. The solid was washed with ethanol and diethyl ether to afford the title compound as a white powder (5.5 g).

$^1$H NMR (250 MHz, d$^6$DMSO) δ(ppm): 7.89 (d, 1H), 7.79 (d, 1H), 7.68 (dd, 1H), 3.36 (s, 3H), 2.45 (s, 3H).

Description 72
2-(4-Bromo-3-methylphenyl)-5-methyl-1,3,4-thiadiazole

N'-acetyl-4-bromo-3-methylbenzoic hydrazide (D71, 3 g) was converted to the crude title compound (1.6 g) according to the literature method (P. B. Rasmussen et al. *Bull. Soc. Chim. Fr.*, 1985, 62–65).

Description 73
2'-Methyl-4'-(5-methyl-1,3,4-thiadiazol-2-yl)biphenyl-4-carboxylic acid The title compound was prepared from 2-(4-bromo-3-methylphenyl)-5-methyl-1,3,4-thiadiazole (D72) using the general procedure of Description 11. This was used in the next step without purification.

Description 74
N-[2-(1,3-Dioxolan-2-yl)propyl]-4-bromo-3-methylbenzamide

A stirred suspension of 4-bromo-3-methylbenzoic acid (2.15 g, 10 mmol) in thionyl chloride (15 ml) was heated under reflux for 1 hour, then concentrated in vacuo to leave the acid chloride as a red oil. This was dissolved in dichloromethane (20 ml) and added dropwise to a stirred solution of 2-(1,3-dioxalan-2-yl)propylamine (*J. Org. Chem.*, 1972, 37, 221) (2.34 g, 20 mmole) and triethylamine (2.8 ml, 20 mmole) in a mixture of dichloromethane (150 ml) and dry THF (50 ml) at 0° C. under argon. The mixture was allowed to warm to room temp. and stir for 18 hours, then concentrated in vacuo. The residue was dissolved in dichloromethane, washed with 1M HCl, then dilute $K_2CO_3$ solution and water, then dried ($Na_2SO_4$) and concentrated in vacuo to afford the title compound as a yellow solid (2.8 g, 8.9%).

$^1$H NMR (250 MHz, $CDCl_3$) δ(ppm): 7.67 (d, 1H), 7.60 (d, 1H), 7.42 (dd, 1H), 6.32 (br t, 1H), 4.06–3.96 (m, 4H), 3.61 (d, 2H), 2.45 (s, 3H), 1.39 (s, 3H).

Description 75
2-(4-Bromo-3-methylphenyl)-5-methyloxazole

N-[2-(1,3-Dioxolan-2-yl)propyl]-4-bromo-3-methylbenzamide (D74, 2.8 g, 8.9 mmole) was added portionwise over 5 minutes to well stirred polyphosphoric acid (50 g) at 120° C. under argon, then heated at 160° C. for 35 minutes. The reaction mixture was allowed to cool, then treated with water (200 ml) and stirred well to dissolve the glassy mass. The mixture was extracted with ethyl acetate and the extract washed with 10% $Na_2CO_3$ solution and water, then dried ($Na_2SO_4$) and concentrated in vacuo. The residue was chromatographed on silica gel eluting with 1:1 ether/60–80 petrol to afford the title compound as a pale yellow solid (2.0 g, 89%).

$^1$H NMR (250 $CDCl_3$) δ(ppm): 7.87 (s, 1H), 7.66 (dd, 1H), 7.58 (d, 1H), 6.82 (s, 1H), 2.45 (s, 3H), 2.38 (s, 3H).

Description 76
2'-Methyl-4'-(5-methyloxazol-2-yl)biphenyl-4-carboxylic acid

The title compound was prepared from 2-(4-bromo-3-methylphenyl)-5-methyloxazole (D75) using a similar procedure to Description 11 as a white solid (86%).

$^1$H NMR (250 MHz, $d^6DMSO$) δ(ppm): 8.02 (d, 2H), 7.88 (s, 1H), 7.83 (d, 1H), 7.51 (d, 2H), 7.38 (d, 1H), 7.02 (s, 1H), 2.40 (s, 3H), 2.31 (s, 3H).

Description 77
(4-Bromo-3-methylphenyl)butane-1,3-dione

A solution of 4-bromo-3-methylacetophenone (D18) (2 g, 0.0093 mol) in dry toluene (28 ml) was treated under argon with sodium hydride (80% dispersion in mineral oil) (0.28 g, 0.0093 mol) and ethyl acetate (1.37 mls, 0.014 mol), followed by one drop of ethanol. The mixture was heated to reflux with stirring for 1 hour then cooled. Brine was added and the mixture was extracted into ethyl acetate, the organic phase was dried ($Na_2SO_4$) and concentrated in vacuo, and the residual crude mixture was purified by chromatography on silica gel, eluting with dichloromethane and methanol, to afford the title compound as a yellow solid (623 mg, 26%).

$^1$H NMR (enol form) (200 MHz, $CDCl_3$) δ(ppm): 16.1 (s, 1H), 7.75 (s, 1H), 7.6 (d, 1H), 7.52 (d, 1H), 6.15 (s, 1H), 2.45 (s, 3H), 2.2 (s, 3H).

Description 78
5-(4-Bromo-3-methylphenyl)-3-methylisoxazole

A solution of 1-(4-bromo-3-methylphenyl)butane-1,3-dione (D77) (615 mg; 0.0024 ml) in ethanol (15 ml) was treated with hydroxylamine hydrochloride (170 mg; 0.0024 mol) and potassium carbonate (336 mg; 0.0024 mol), and the mixture heated at reflux for 2.5 hours, then overnight at room temperature. The solvent was evaporated under reduced pressure and the residue partitioned between water and ethyl acetate. The organic phase was dried ($Na_2SO_4$) and concentrated in vacuo to leave the crude isoxazole, which was purified by chromatography on silica gel, eluting with pentane, 60–80 petroleum-ether and ethyl acetate, to afford the title compound as a yellow crystalline material (477 mg, 78%).

$^1$H NMR (250 MHz, $CDCl_3$) δ(ppm): 7.65–7.56 (m, 2H), 7.4 (d, 1H), 6.35 (s, 1H), 2.45 (s, 3H), 2.35 (s, 3H).

Description 79
2'-Methyl-4'-(3-methylisoxazol-5-yl)biphenyl-4-carboxylic acid The title compound was prepared from 5-(4-bromo-3-methylphenyl)-3-methylisoxazole (D78) using a similar procedure to Description 11 (48%) as a yellow solid.

$^1$H NMR (200 MHz, $CDCl_3$) δ(ppm): 8.04–7.9 (m, 2H), 7.78 (s, 1H), 7.7 (d, 1H), 7.4–7.2 (m, 3H), 6.9 (s, 1H), 2.4–2.2 (m, 6H).

Description 80
4-Bromo-3-methylbenzaldehyde

A solution of N-methoxy-N-methyl-4-bromo-3-methylbenzamide (D17) (12 g; 0.046 mol) in dry tetrahydrofuran (120 ml) under argon, at −78° C. was treated dropwise over 15 minutes with diisobutylaluminium hydride (1.5 m in toluene) (46 ml; 0.069 mol). After a further 15 minutes the reaction mixture was added to 5N HCl (100 ml) and extracted into diethyl ether. The organic phase was dried ($Na_2SO_4$) and evaporated under reduced pressure to give the title compound as a red oil (8.98 g, 97%).

$^1$H NMR (200 MHz, $CDCl_3$) δ(ppm): 9.95 (s, 1H), 7.76–7.65 (m, 2H), 7.55 (d, 1H), 2.48 (s, 3H)

Description 81
4-Bromo-3-methylbenzaldehyde oxime

A solution of 4-bromo-3-methylbenzaldehyde (D80) (1 g; 0.005 mol) in methanol (20 ml) was treated with hydroxylamine hydrochloride (700 mg, 0.01 mol) and the mixture stood at room temperature over a weekend. The solvent was evaporated under reduced pressure and the residual solid was partitioned between saturated $K_2CO_3$ solution and ethyl acetate. The organic phase was dried ($Na_2SO_4$), concentrated in vacuo and the residue purified by chromatography on silica gel eluting with 60–80 petroleum-ether and ethyl acetate, to afford the title compound as a pale pink powder (693 mg, 20%).

$^1$H NMR (200 MHz, CDCl$_3$) δ(ppm): 9.15 (br s, 1H), 7.8 (s, 1H), 7.67 (d, 1H), 7.59 (d, 1H), 7.32 (s, 1H), 2.43 (s, 3H).

Description 82
3-(4-Bromo-3-methylphenyl)-5-methylisoxazole

A solution of 4-bromo-3-methylbenzaldehyde oxime (D81) (2.68 g, 0.0125 mol) in dry dimethylformamide (30 ml) was treated over 15 minutes with N-bromosuccinimide (636 mg, 0.00357 mol), and reaction mixture stirred for 2.5 hours, then cooled to −15° C. 2-Chloropropene (3.45 ml, 0.0405 mol) was added in a single portion, followed by dropwise addition of triethylamine (1.35 ml, 0.0097 mol) in dry dimethylformamide (10 ml) over 0.5 hours maintaining the temp. at −10° C. The mixture was stirred at 0° C. for 1 hour, then stirred at room temperature overnight. The solvent was evaporated under reduced pressure and the residue partitioned between K$_2$CO$_3$ solution and chloroform. The organic phase was dried (Na$_2$SO$_4$) and evaporated under reduced pressure and the residue purified by chromatography on silica gel eluting with 60–80 petroleum-ether and ethyl acetate, to afford the title compound (246 mg, 8%).

$^1$H NMR (200 MHz, CDCl$_3$) δ(ppm): 7.68 (s, 1H), 7.6 (d, 1H), 7.43 (d, 1H), 6.26 (s, 1H), 2.48 (s, 3H), 2.45 (s, 3H).

Description 83
2'-Methyl-4'-(5-methylisoxazol-3-yl)biphenyl-4-carboxylic acid The title compound was prepared from 3-(4-bromo-3-methylphenyl)-5-methylisoxazole (D82) using a similar procedure to Description 11 (57%).

$^1$H NMR (250 MHz, d$^6$DMSO) δ(ppm): 13.05 (br s, 1H), 8.04 (d, 2H), 7.82 (s, 1H), 7.75 (d, 1H), 7.52 (d, 2H), 7.36 (d, 1H), 6.81 (s, 1H), 2.49 (s, 3H), 2.3 (s, 3H).

Description 84
(4-Bromo-3-methylphenyl)pyrazine

A stirred solution of diisopropylamine (2.44 ml, 0.018 mol) in dry THF (40 ml) under argon was treated with n-butyllithium (1.6M) (10.1 ml, 0.016 mol) at −60° C. After 15 minutes the resultant mixture was treated with methyl phenyl sulphoxide (1.68 g, 0.014 mol) in dry THF (15 ml). After a further 15 minutes a solution of N-methyl-N-methoxy-4-bromo-3-methyl-benzamide (D17) (3.00 g, 0.012 mol) in dry THF (30 ml) was added dropwise and the reaction mixture was allowed to warm to room temperature over 2 h and was left stirring at room temp. for 18 h, before 10% sodium carbonate solution (50 ml) was added. The reaction mixture was then concentrated in vacuo and the residue was partitioned between water and dichloromethane. The aqueous layer was then extracted with dichloromethane (1X) and the combined organic layers were dried (Na$_2$SO$_4$) and evaporated under reduced pressure to give an orange oil which was dried in vacuo (3.60 g). The oil was then redissolved in dichloromethane (70 ml) and was cooled to 0° C. under argon. Trifluoroacetic acid (0.960 ml, 0.013 mol) was then added, followed by trifluoroacetic anhydride (3.53 ml, 0.025 mol). After 30 minutes, the reaction mixture was evaporated under reduced pressure to give an orange oil. A solution of sodium hydrogen carbonate (3.70 g, 0.044 mol) in water (75 ml) was then added, followed by ethanol (250 ml). Ethylene diamine (0.840 ml, 0.013 mol) was then added to the resultant stirred suspension. After 18 h, the reaction mixture was concentrated in vacuo and the residue was partitioned between dichloromethane and water. The aqueous layer was then extracted with dichloromethane, and the combined organic layers were dried (Na$_2$SO$_4$) and evaporated under reduced pressure to give a dark red oil, which was dried in vacuo (3.65 g). The oil was then redissolved in ethanol (80 ml) and was treated with potassium hydroxide (0.703 g, 0.013 mol). The resultant solution was then heated to reflux. After 24 h, the reaction mixture was allowed to cool and was evaporated under reduced pressure to give a dark oil, which was partitioned between dichloromethane and water. The organic layer was then dried (Na$_2$SO$_4$) and evaporated under reduced pressure to give a dark brown oil, which was purified by silica-gel chromatography (20% Et$_2$O/pentane as eluant) to give the title compound as a pale yellow solid (0.583 g, 21%).

$^1$H NMR (200 MHz, CDCl$_3$) δ(ppm): 9.00 (s, 1H), 8.62 (d, 1H), 8.51 (d, 1H), 7.90 (s, 1H), 7.70 (s, 2H), 2.50 (s, 3H).

Description 85
2'-Methyl-4'-pyrazinylbiphenyl-4-carboxylic acid (4-Bromo-3-methylphenyl)pyrazine (D84, 0.300 g, 1.21 mmol) was converted to give the title compound (0.279 g, 88%) as a white solid, according to the method described in Description 11.

$^1$H NMR (250 MHz, CD$_3$SOCD$_3$) δ(ppm): 9.30 (d, 1H), 8.72 (d, 1H), 8.62 (d, 1H), 8.12 (s, 1H), 8.05 (m, 3H), 7.52 (d, 2H), 7.41 (d, 1H), 2.31 (s, 3H)

Description 86
Methyl 2'-methyl-4'-pyrazinylbiphenyl-4-carboxylate

Thionyl chloride (0.076 ml, 1.043 mmol) was added to methanol (7 ml) at 0° C. After 15 minutes, 2'-methyl-4'-pyrazinylbiphenyl-4-carboxylic acid (D85, 0.216 g, 0.745 mmol) was added and the mixture was heated to reflux. After 5 h, the reaction mixture was allowed to cool and was left at room temperature overnight. The reaction mixture was then evaporated under reduced pressure and the residue was partitioned between dichloromethane (25 ml) and 10% sodium carbonate solution (20 ml). The aqueous layer was then extracted with dichloromethane (1×10 ml), and the combined organic layers were then dried (Na$_2$SO$_4$) and evaporated under reduced pressure to give the title compound as a yellow/brown solid (0.146 g, 65%).

$^1$H NMR (250 MHz, CDCl$_3$) δ(ppm): 9.10 (s, 1H), 8.68 (t, 1H), 8.52 (d, 1H), 8.13 (d, 2H), 8.00 (s, 1H), 7.90 dd, 1H), 7.45 (d, 2H), 7.40 (d, 1H), 3.98 (s, 3H), 2.38 (s, 3H).

Description 87
Methyl 4-bromo-3-methylbenzimidate hydrochloride

4-Bromo-3-methylbenzonitrile (15.0 g, 76.5 mmol) was dissolved in dry methanol (3.1 ml, 76.5 mmol) and dry diethyl ether (108 ml), cooled to 0–5°, then saturated with HCl (g). Stirred for 18 hours at room temperature and the solid collected by filtration, then dried in vacuo to yield the title compound as white needle-like crystals (19.3 g, 95%).

$^1$H NMR (250 MHz, CDCl$_3$) δ(ppm): 12.7 (s, 1H), 12.0 (s, 1H), 8.35 (d, 1H), 8.05–8.00 (m, 1H), 7.70 (d, 1H), 4.55 (s, 3H), 2.50 (s, 3H).

Description 88
2-(4-Bromo-3-methylphenyl)imidazole

Methyl 4-bromo-3-methylbenzimidate hydrochloride (D87, 5.0 g; 21.9 mmol) was dissolved in methanol (30 ml) and stirred during the addition of a solution of 2-aminoacetaldehyde dimethyl acetal (2.4 ml; 21.9 mmol) in methanol (10 ml) over 30 minutes. Stirring was continued for 36 hours and evaporated in vacuo to yield an orange gum (7 g crude). This crude hydrochloride was treated with conc. H$_2$SO$_4$ (12 ml) at 5°, the heated at 50° for 10 minutes. The solution was cooled in ice, diluted with H$_2$O and basified with 10% NaOH. The aqueous solution was extracted with chloroform (4 times) and the organics combined, dried over Na$_2$SO$_4$, filtered and evaporated in vacuo. The residue was purified by flash silica gel chromatography eluting with 1% MeOH/CHCl₃ to yield the title compound as a white solid (1.55 g; 44%).

¹H NMR (250 MHz, CDCl₃) δ(ppm): 7.70 (d, 1H), 7.55–7.45 (m, 2H), 7.15 (s, 2H), 2.35 (s, 3H).

Description 89
2-(4-Bromo-3-methylphenyl)-1-methylimidazole 2-(4-Bromo-3-methylphenyl)imidazole (D88, 900 mg; 3.8 mmol) was dissolved in dry THF (30 ml) under argon and treated with sodium hydride (114 mg of an 80% dispersion in mineral oil; 3.8 mmol). After stirring for 30 minutes, iodomethane (237 μl; 3.8 mmol) was added and stirring continued for 18 hours. Evaporated in vacuo, the residue partitioned between water and CHCl₃, the organic phase then dried over Na₂SO₄, filtered and evaporated in vacuo. The residue was purified by flash silica gel chromatography using CHCl₃ as eluant to yield the title compound as a clear, colourless gum (600 mg; 63%).

¹H NMR (200 MHz, CDCl₃) δ(ppm): 7.60–7.50 (m, 2H), 7.30–7.20 (m, 1H), 7.10 (s, 1H), 6.95 (s, 1H), 3.75 (s, 3H), 2.45 (s, 3H).

Description 90
2'-Methyl-4'-(1-methylimidazol-2-yl)biphenyl-4-carboxylic acid 2-(4-Bromo-3-methylphenyl)-1-methylimidazole (D89, 600 mg, 2.39 mmol) was dissolved in dimethoxyethane (15 ml) and H₂O (15 ml) and treated with 4-boronobenzoic acid (397 mg, 2.39 mmol), sodium carbonate (1.01 g, 9.56 mmol), tetrakis (triphenylphosphine)palladium (O) (60 mg) and heated at reflux for 36 hours. The dimethoxyethane was removed in vacuo, the aqueous residue treated with 10% Na₂CO₃ (approx. 10 ml) and washed with ethyl acetate. The aqueous phase was acidified with 5N HCl and the solid that formed collected by filtration and dried in vacuo to yield the title compound as an off-white solid (620 mg, 89%).

¹H NMR (250 MHz, d⁶DMSO) δ(ppm): 8.10–8.00 (m, 3H), 7.95–7.75 (m, 3H), 7.65–7.50 (m, 3H), 4.00 (s, 3H), 2.35 (s, 3H)

Description 91
(4-Bromo-3-methylbenzylidene)methylamine

4-Bromo-3-methylbenzaldehyde (D80, 3.7 g, 18.6 mmol) was treated with methylamine in ethanol (33%, 100 ml) followed by 4 Å molecular sieves and solid potassium carbonate (approx 4 g) and the mixture stirred for 72 hours. Solvent was removed in vacuo, the residue suspended in chloroform, and the solid removed by filtration. The filtrate was evaporated in vacuo to yield the title compound as a red liquid (3.15 g, 80%).

¹H NMR (250 MHz, CDCl₃) δ(ppm): 8.20 (s, 1H), 7.65–7.55 (m, 2H), 7.40–7.30 (m, 1H), 3.50 (s, 3H), 2.45 (s, 3H).

Description 92
5-(4-Bromo-3-methylphenyl)-1-methylimidazole (4-Bromo-3-methylbenzylidene)methylamine (D91, 2.15 g, 10.1 mmol) was dissolved in dry DME (30 ml) and methanol (70 ml) containing tosylmethylisocyanide (3.0 g; 15.4 mmol) and this solution was treated with potassium carbonate (2.8 g, 20.3 mmol). The whole was heated at reflux for 48 hours, cooled and evaporated in vacuo. The residue was partitioned between brine and chloroform (3 times), and the organics combined and dried over Na₂SO₄. The organics were filtered and evaporated in vacuo then the residue purified by flash silica gel chromatography (with chloroform as eluant) to yield the title compound as an orange gum (1.52 g, 60%).

¹H NMR (250 MHz, CDCl₃) δ(ppm): 7.60 (d, 1H), 7.50 (s, 1H), 7.25 (s, 1H), 7.10–7.00 (m, 2H), 3.65 (s, 3H), 2.45 (s, 3H).

Description 93
2'-Methyl-4'-(1-methylimidazol-5-yl)biphenyl-4-carboxylic acid 5-(4-Bromo-3-methylphenyl)-1-methylimidazole (D92, 1.52 g, 6.1 mmol) was dissolved in DME (50 ml) and water (50 ml), then treated with 4-boronobenzoic acid (1.0 g, 6.1 mmol), sodium carbonate (2.57 g, 24.2 mmol) and tetrakis (triphenylphosphine)palladium (O) (100 mg). The mixture was heated at reflux (48 hours), cooled and the DME removed in vacuo. The aqueous residue was treated with 10% Na₂CO₃ (approx 30 ml), then washed with ethyl acetate. The aqueous phase was acidified with 5N HCl and the solid that precipitated was collected by filtration. This solid was dried in vacuo to yield the title compound as a white solid (600 mg, 34%).

¹H NMR (250 MHz, d⁶DMSO) δ(ppm): 9.20 (s, 1H), 8.05 (d, 2H), 7.85 (s, 1H), 7.60–7.40 (m, 5H), 3.90 (s, 3H), 2.30 (s, 3H).

Description 94
Methyl-4'-(5-hydroxymethyl-1,2,4-oxadiazol-3-yl) biphenyl-4-carboxylate 3-(4-Bromo-3-methylphenyl)-1,2,4-oxadiazol-5-ylmethanol (EP 0533268 A1) (1.0 g, 3.7 mmol) was reacted with 4-boronobenzoic acid using similar conditions to Description 11 to afford 4'-(5-hydroxymethyl-1,2,4-oxadiazol-3-yl)biphenyl-4-carboxylic acid. This was dissolved in methanol (70 ml), treated with conc. sulphuric acid (2 ml) and heated under reflux for 4 hours. The solution was concentrated in vacuo and the residue basified with 10% Na₂CO₃ solution and extracted with ethyl acetate. The extract was dried (Na₂SO₄) and concentrated in vacuo to afford the title compound (0.76 g, 68%).

¹H NMR (250 MHz, CHCl₃) δ(ppm): 8.12 (d, 2H), 8.04 (s, 1H), 7.96 (d, 1H), 7.42 (d, 2H), 7.35 (d, 1H), 5.00 (s, 2H), 3.96 (s, 3H), 3.0 (brs, 1H), 2.33 (s, 3H).

Description 95
Methyl 4'-[5-(t-butyldimethylsilyloxy)-1,2,4-oxadiazol-3-yl]-2'-methylbiphenyl-4-carboxylate A stirred solution of methyl 4'-(5-hydroxymethyl-1,2,4-oxadiazol-3-yl)biphenyl-4-carboxylate (D94, 0.51 g, 1.8 mmole) in dichloromethane (30 ml) was treated with triethylamine (0.50 ml, 3.6 mmole), followed by a solution of t-butyldimethylsilyl chloride (0.29 g, 1.8 mmole) in dichloromethane (5 ml), and 4-dimethylaminopyridine (29 mg). The solution was left at room temp. for 14 h, then additional t-butyldimethylsilyl chloride (0.11 g, 0.7 mmole) and triethylamine (0.20 ml) were added and reaction left at room temp. for 4 days. The solution was washed rapidly with 0.5M HCl acid, then 10% Na₂CO₃ solution, dried (Na₂SO₄) and concentrated in vacuo. The residue was chromatographed on silica gel eluting with 10% ether/60–80 petrol to afford the title compound as a white solid (0.61 g, 78%).

Description 96
4-Bromo-3-methylphenylamidrazone

Methyl 4-bromo-3-methylbenzimidate hydrochloride (D87, 24.6 g, 0.093 mole) was partitioned between ether (150 ml) and aqueous sodium hydroxide (5%, 160 ml). The organic layer was washed with water, dried (Na₂SO₄) and concentrated in vacuo. To the residue was added hydrazine hydrate (4.51 ml, 0.093 mole) in either (15 ml) and ethanol (75 ml). The solvent was concentrate din vacuo to afford the title compound as a solid (6 g, 28%).

¹H NMR (250 MHz, d⁶DMSO+D₂O) δ(ppm): 8.05 (d, 1H), 7.75 (dd, 1H), 7.60 (d, 1H), 2.40 (s, 3H).

Description 97
3-(4-Bromo-3-methylphenyl)-1,2,4-triazine

Aqueous glyoxal (14 ml) was heated to 80° C. and added to a suspension of 4-bromo-3-methylphenylamidrazone (D96, 10 g, 0.044 mole) in water (50 ml). The mixture was heated at 70° C. for 15 min, cooled and filtered. The solid was suspended in methanol and stirred at ambient temperature for 72 hours. The mixture was filtered through kieselguhr and the filtrate concentrated in vacuo. The residue was chromatographed on silica gel eluting with 10% ethanol/chloroform to give the title compound as a yellow solid (2.36 g, 22%).

¹H NMR (250 MHz, CDCl₃) δ(ppm): 9.20 (d, 1H), 8.70 (d, 1H), 8.45 (d, 1H), 8.20 (d, 1H), 7.70 (d, 1H), 2.50 (s, 3H).

Description 98
2'-Methyl-4'-(1,2,4-triazin-3-yl)biphenyl-4-carboxylic acid 3-(4-Bromo-3-methylphenyl)-1,2,4-triazine (D97, 1 g, 0.004 mole) was converted to the title compound (260 mg, 22%) by the method of Example 11.

¹H NMR (250 MHz, d⁶DMSO) δ(ppm): 13.1 (br s, 1H), 9.40 (d, 1H), 8.95 (d, 1H), 8.45 (s, 1H), 8.35 (dd, 1H), 8.05 (d, 2H), 7.55 (d, 2H), 7.50 (d, 1H), 2.40 (s, 3H).

Description 99
4-(2-(2-Iodophenoxy)ethyl)pyridine

A stirred solution of 2-iodophenol (8.8 g, 0.040 mole), triphenylphosphine (10.5 g, 0.040 mole) and 2-(4-pyridyl)ethanol (D65, 5.5 g, 0.045 mole) in THF (200 ml) at 0° C. under argon was treated with a solution of diethyl azodicarboxylate (6.3 ml, 0.040 mole) in THF (30 ml). The solution was allowed to warm to room temp. and stirred for 4 h, then concentrated in vacuo and the residue treated with 10% Na₂CO₃ solution (80 ml) and extracted with ethyl acetate (2×80 ml). The combined organic was extracted with 1M HCl acid (150 ml), then the acid extract basified by addition of potassium carbonate and extracted with ethyl acetate (2×100 ml). The combined extract was dried (Na₂SO₄) and concentrated in vacuo to leave a brown oil, which was chromatographed on silica gel eluting with 0 to 15% ethyl acetate/ether to afford the title compound as a colourless oil (9.3 g, 72%).

¹H NMR (250 MHz, CDCl₃) δ(ppm): 8.58–8.51 (m, 2H), 7.76 (dd, 1H), 7.40–7.22 (m, 3H), 6.82–6.68 (m, 2H), 4.23 (t, 2H), 3.15 (t, 2H).

Description 100
4-(2-(2-Iodophenoxy)ethyl)-1-methyl-1,2,3,6-tetrahydropyridine

A solution of 4-(2-(2-iodophenoxy)ethyl)pyridine (D99, 8.28 g, 0.025 mole) in acetone (220 ml) was treated with iodomethane (3.7 ml, 0.059 mole) and kept at room temperature for 24 h, then concentrated in vacuo to leave the quaternary salt as a yellow oil. This was dissolved in a mixture of ethanol (50 ml) and water (50 ml), cooled to 0° C. under argon and treated portionwise over 1 h with sodium borohydride (1.33 g, 0.035 mole). The reaction mixture was kept at 0° C. for a further 1 h, then treated with 10% NaOH solution (50 ml), diluted with water (120 ml) and extracted with ethyl acetate (2×200 ml). The combined extract was dried (Na₂SO₄), concentrated in vacuo to leave an orange oil, which was chromatographed on silica gel eluting with 0–10% methanol/chloroform to afford the title compound as a yellow oil (6.19 g, 72%).

¹H NMR (250 MHz, CDCl₃) δ(ppm): 7.76 (dd, 1H), 7.28 (dt, 1H), 6.79 (dd, 1H), 6.70 (dt, 1H), 5.57 (m, 1H), 4.09 (t, 2H), 3.00–2.90 (m, 2H), 2.65–2.48 (m, 4H), 2.36 (s, 3H), 2.32–2.20 (m, 2H).

Description 101
2,3-Dihydro-1'-methylspiro[4H-benzopyran-4,4'-piperidine]

A stirred solution of 4-(2-(2-iodophenoxy)ethyl)-1-methyl-1,2,3,6-tetrahydropyridine (D100, 6.3 g, 0.018 mole) and AIBN (50 mg) in benzene (700 ml) was heated to reflux under argon, then treated dropwise over 1 h with a solution of tributyltin hydride (9.7 ml, 0.036 mole) in benzene (100 ml). The reaction mixture was heated under reflux for a further 3 h after completing the addition, then more tributyltin hydride (3.8 ml, 0.014 mole) and AIBN (30 mg) were added and heating under reflux was continued for 4 h. The reaction mixture was allowed to cool, then concentrated in vacuo and the residue treated with 2M HCl acid (150 ml), washed with ethyl acetate (100 ml), basified with potassium carbonate and extracted with ethyl acetate (2×100 ml). The combined extract was dried (Na₂SO₄) and concentrated in vacuo to leave a yellow oil, which was chromatographed on silica gel eluting with 0 to 2% methanol/chloroform to afford the title compound (2.3 g of approx. 86% purity, 51%).

¹H NMR (250 MHz, CDCl₃) δ(ppm): 7.38 (dd, 1H), 7.08 (dt, 1H), 6.90 (dt, 1H), 6.79 (dd, 1H), 4.18–4.10 (m, 2H), 2.83–2.70 (m, 2H), 2.45–2.25 (m, 4H), 2.35 (s, 3H), 2.05–1.95 (m, 2H), 1.70–1.55 (m, 2H).

Description 102
2,3-Dihydro-1'-ethoxycarbonylspiro[4H-benzopyran-4,4'-piperidine]

A stirred solution of 2,3-dihydro-1'-methylspiro[4H-benzopyran-4,4'-piperidine] (D101, 1.0 g, 0.0046 mole) and diisopropylethylamine (1.2 ml, 0.0070 mole) in dichloroethane (20 ml) was treated with 1-chloroethyl chloroformate (0.64 ml, 0.0060 mole) and kept at room temp. for 1 h followed by 20 mins at reflux. The solution was then concentrated in vacuo and the residue treated with methanol (20 ml) and heated under reflux for 2 h. The reaction mixture was concentrated in vacuo to leave a beige solid, which was dissolved in dichloromethane (50 ml) and THF (10 ml) and treated with triethylamine (0.84 ml, 0.0060 mole) followed by ethyl chloroformate (0.44 ml, 0.0046 mole). The solution was stirred at room temperature for 2 h, then treated with 10% Na₂CO₃ solution (20 ml) and extracted with dichloromethane (2×40 ml). The combined extract was dried (Na₂SO₄) and concentrated in vacuo. The residue was chromatographed on silica gel eluting with 1:1 ether/60–80 petrol to afford the title compound as a yellow oil (1.3 g, 100%).

¹H NMR (250 MHz, CDCl₃) δ(ppm): 7.25 (dd, 1H), 7.10 (dt, 1H), 6.90 (dt, 1H), 6.80 (dd, 1H), 4.25–4.00 (m, 6H), 2.98 (br t, 2H), 2.10–1.92 (m, 4H), 1.70–1.53 (m, 2H), 1.28 (t, 3H).

Description 103
2,3-Dihydro-1'-ethoxycarbonyl-6-and 8-nitrospiro[4H-benzopyran-4,4'piperidine]

A stirred solution of 2,3-dihydro-1'-ethoxycarbonylspiro [4H-benzopyran-4,4'-piperidine] (D102, 1.3 g, 0.0046 mole) in acetic anhydride (30 ml) at 0° C. under argon was treated portionwise over 15 minutes with copper (II) nitrate hemipentahydrate (1.16 g, 0.0050 mole). The reaction mixture was kept at 0° C. for a total of 1.5 h, then allowed to warm to room temperature over 0.5 h. The mixture was poured into water/ice (300 ml) and basified by careful addition of potassium carbonate, then extracted with ethyl acetate (2×100 ml). The combined extract was dried (Na₂SO₄) and concentrated in vacuo to afford an orange oil (1.5 g, 100%), which was approximately a 1:1 mixture of 6- and 8-nitro isomers. This was used without purification.

¹H NMR (250 MHz, CDCl₃) δ(ppm): 8.24 (d, 1H 6-isomer), 8.00 (dd, 1H 6-isomer), 7.64 (dd, 1H 8-isomer), 7.52 (dd, 1H 8-isomer), 6.98 (t, 1H 8-isomer), 6.90 (d, 1H 6-isomer), 4.35–4.05 (m, 6H), 3.00 (br t, 2H), 2.25–1.95 (m, 4H), 1.75–1.60 (m, 2H), 1.35–1.22 (m, 3H).

Description 104
6-Amino-2,3-dihydro-1'-ethoxycarbonylspiro[4H-benzopyran-4,4'-piperidine]

A solution of 2,3-dihydro-1'-ethoxycarbonyl-6- and 8-nitrospiro[4H-benzopyran-4,4'-piperidine] (D103, 1.5 g, 0.0046 mole) in ethanol (100 ml) was hydrogenated over 10% Pd-C (300 mg) at atmospheric temperature and pressure until uptake of hydrogen ceased. The catalyst was removed by filtration through kieselguhr and the filtrate concentrated in vacuo. The mixture of 6- and 8-amino isomers was separated by chromatography on silica gel eluting with ether to afford the 6-amino compound as the lower rf component (420 mg, 32%).

¹H NMR (250 MHz, CDCl₃) δ(ppm): 6.66 (d, 1H), 6.60 (d, 1H), 6.50 (dd, 1H), 4.25–4.00 (m, 4H), 4.17 (q, 2H), 3.45 (br s, 2H), 2.98 (br t, 2H), 2.08–1.88 (m, 4H), 1.70–1.55 (m, 2H), 1.30 (t, 3H).

Description 105
6-Amino-2,3-dihydro-1'-methylspiro[4H-benzopyran-4,4'-piperidine]

A stirred suspension of lithium aluminium hydride (76 mg, 0.0020 mole) in THF (15 ml) at 0° C. under argon was treated with a solution of 6-amino-2,3-dihydro-1'-ethoxycarbonylspiro[4H-benzopyran-4,4'-piperidine] (D104, 300 mg, 0.0010 mole) in THF (5 ml). The reaction mixture was allowed to warm to room temp. and stir for 1.5 h, then treated with more lithium aluminium hydride (38 mg, 0.0010 mole) suspended in THF (5 ml). The mixture was heated under reflux for 0.75 h, then cooled in an ice bath and treated with water (0.10 ml), 10% NaOH solution (0.10 ml) and water (0.30 ml). The resulting mixture was filtered through kieselguhr and the filtrate concentrated in vacuo to afford the title compound as a yellow oil (200 mg, 84%).

¹H NMR (200 MHz, CDCl₃) δ(ppm): 6.73 (d, 1H), 6.65 (d, 1H), 6.48 (dd, 1H), 4.10–4.00 (m, 2H), 3.3 (br s, 2H), 2.85–2.70 (m, 2H), 2.35 (s, 3H), 2.30–1.90 (m, 6H), 1.75–1.53 (m, 2H).

Description 106
2,3-Dihydro-1'-methylspiro[4H-pyrano[2,3-g]quinoline-4,4'piperidine]

A stirred suspension of 6-amino-2,3-dihydro-1'-methylspiro[4H-benzopyran-4,4'piperidine] (D105, 330 mg, 0.0014 mole) in glycol (1 ml) at room temperature was treated with a catalytic amount of iodine (7 mg) and concentrated sulphuric acid (0.5 ml). An exothermic reaction took place, which was well controlled and required no cooling. The reaction mixture was then heated to 175° C. for 2 hrs and allowed to cool to 100° C. before water (20 ml) was added. The mixture was basified with 5M sodium hydroxide and then extracted with ethyl acetate (3×100 ml). The combined extracts were dried (Na₂SO₄) and concentrated in vacuo. The residue was purified by chromatography on silica gel eluting with 25–30% methanol/dichloromethane to afford the title compound as a white solid (150 mg, 39%).

¹H NMR (200 MHz, CDCl₃) δ(ppm): 8.73 (dd, 1H), 8.16 (s, 1H), 7.98 (d, 1H), 7.28 dd, 1H), 7.16 (s, 1H), 4.26 (dd, 2H), 2.83 (br dd, 2H), 2.38 (s, 3H), 2.35–2.15 (m, 6H), 1.79 (br d, 2H).

Description 107
2,3,6,7,8,9-Hexahydro-1'-methylspiro[4H pyrano[2,3-g]quinoline-4,4' piperidine]

A solution of 2,3-dihydro-1'-methylspiro[4H-pyrano[2,3-g]quinoline-4,4' piperidine] (D106, 150 mg, 0.0006 mole) in ethanol (50 ml) and glacial acetic acid (2 ml) was hydrogenated over PtO₂ (35 mg) at 50 psi for 2 days. The catalyst was removed by filtration through kieselguhr and the filtrate concentrated in vacuo. The residue was purified by chromatography on silica gel eluting with 30% MeOH/dichloromethane with 1% ammonia solution to afford the title compound (150 mg, 99%).

¹H NMR (200 MHz, CD₃OD) δ(ppm): 6.59 (s, 1H), 6.41 (s, 1H), 4.05 (dd, 2H), 3.45–3.15 (m, 6H), 2.91 (s, 3H), 2.69 (t, 2H), 2.37 (td, 2H), 2.05 (dd, 2H), 2.00–1.79 (m, 4H).

Description 108
1-Ethyl-1,2,3,6-tetrahydropyridine-4-methanol

The title compound was prepared from 4-pyridylcarbinol and iodoethane following a similar procedure to that described for the 1-methyl analogue in *J. Med. Chem.*, 1988, 31, 545(92%).

¹H NMR (200 MHz, CDCl₃) δ(ppm): 5.63 (m, 1H), 4.00 (s, 2H), 3.14 (br s, 1H), 2.97 (m, 2H), 2.58 (t, 2H), 2.50 (q, 2H), 2.18 (m, 2H), 1.13 (t, 3H).

Description 109
1'-Ethyl-2,3,6,7-tetrahydrospiro[furo[2,3-f]indole-3,4'-piperidine]

This was prepared from 1-acetyl-6-bromo-2,3-dihydro-1H-indol-5-ol (*Tetrahedron*, 1973, 29 (8), 1115) and 1-ethyl-1,2,3,6-tetrahydropyridine-4-methanol (D108), following the procedure of Description 8 (alternative preparation), steps a), b), and c). This gave the title compound (overall yield: 45%) as a fine grey powder.

¹H NMR (200 MHz, CDCl₃) δ(ppm): 6.61 (s, 1H), 6.48 (s, 1H), 4.32 (s, 2H), 3.53 (t, 2H), 2.96 (m, 4H), 2.45 (q, 2H), 1.98 (m, 4H), 1.73 (m, 2H), 1.12 (t, 3H).

Description 110
2-(4-Bromophenyl)-5-methyl-1,3,4-oxadiazole

The title compound was prepared from 4-bromobenzoic hydrazide and triethyl orthoacetate following a similar procedure to that of Description 35, to afford fine white crystals (77%).

¹H NMR (250 MHz, CDCl₃) δ(ppm): 7.92 (d, 2H), 7.67 (d, 2H), 2.63 (s, 3H).

Description 111
4'-(5-Methyl-1,3,4-oxadiazol-2-yl)biphenyl-4-carboxylic acid

The title compound was prepared from a stirred solution of 2-(4-bromophenyl)-5-methyl-1,3,4-oxadiazole (D110) and 4-boronobenzoic acid using a similar procedure to Description 11, as a white crystalline solid (68%).

¹H NMR (250 MHz, d⁶DMSO) δ(ppm): 8.10 (d, 2H), 8.06 (d, 2H), 7.98 (d, 2H), 7.89 (d, 2H), 2.62 (s, 3H).

Description 112
4'-(5-Methoxymethyl-1,2,4-oxadiazol-3-yl)-2'-methylbiphenyl-4-carboxylic acid The title compound was prepared from 3-(4-bromo-3-methylphenyl)-5-methoxymethyl-1,2,4-oxadiazole (EP 0533268 A1) using a similar procedure to Description 11, as an off white solid (49%).

¹H NMR (250 MHz, d⁶DMSO) δ(ppm): 13.06 (br s, 1H). 8.10–7.98 (m, 3H), 7.94 (dd, 1H), 7.55 (d, 2H), 7.45 ) d, 1H), 4.87 (s, 2H), 3.45 (s, 3H), 2.34 (s, 3H).

Description 113
4'-(4,5-Dihydrooxazol-2-yl)-2'-methylbiphenyl-4-carboxylic acid This was prepared from 2-(4-bromo-3-methylphenyl)-4,5-dihydrooxazole (WO94/15920-A1) using the procedure of Description 11. This gave the title compound (85%) as a white powder.

$^1$H NMR (250 MHz, d$^6$DMSO) δ(ppm): 8.02 (d, 2H), 7.7–7.9 (m, 2H), 7.52 (d, 2H), 7.36 (d, 1H), 4.49 (t, 2H), 4.01 (t, 2H), 2.29 (s, 3H).

Description 114
Methyl 4'-(4,5-dihydrooxazol-2-yl)-2'-methylbiphenyl-4-carboxylate 4'-(4,5-Dihydrooxazol-2-yl)-2'-methylbiphenyl-4-carboxylic acid (D113) (0.92 g, 3.3 mmol) was stirred under Ar in dry DMF (20 ml), and sodium hydride (80% in mineral oil, 0.15 g, 5.0 mmol) was added. This mixture was stirred for 30 min, and then treated with iodomethane (0.22 ml, 3.5 mmol). After a further 15 min, the mixture was diluted with ethyl acetate (200 ml), washed with water and brine, dried (Na$_2$SO$_4$) and evaporated. The crude product was purified by chromatography on silica gel, eluting with 0–2% methanol/dichloromethane. This gave the title compound (0.15 g, 15%) as a white solid.

$^1$H NMR (250 MHz, CDCl$_3$) δ(ppm): 8.10 (d, 2H), 7.89 (s, 1H), 7.82 (d, 1H), 7.41 (d, 2H), 7.27 (d, 1H), 4.47 (t, 2H), 4.08 (t, 2H), 3.94 (s, 3H), 2.30 (s, 3H).

Description 115
4'-Amino-2'-methylbiphenyl-4-carboxylic acid

This compound was prepared from 4-bromo-3-methylaniline, following the procedure of Description 11. This gave the title compound (91%) as a mauve powder.

$^1$H NMR (250 MHz, d$^6$DMSO) δ(ppm): 7.93 (d, 2H), 7.39 (d, 2H), 6.93 (d, 1H), 6.50 (m, 2H), 2.16 (s, 3H).

Description 116
4'-(2-Chloroacetamido)-2'-methylbiphenyl-4-carboxylic acid

4'-Amino-2'-methylbiphenyl-4-carboxylic acid (D115, 2.45 g, 10.8 mmol) and triethylamine (3.8 ml, 27.3 mmol) were stirred in dichloromethane (50 ml) as chloroacetyl chloride (1.05 ml, 13.2 mmol) was added dropwise. This mixture was stirred for 3 h, when water (20 ml) was added. After vigorous stirring for 15 min and basification with potassium carbonate solution, the mixture was separated. The aqueous portion was washed with dichloromethane, and acidified with conc. hydrochloric acid. The precipitated solid was filtered off and dried, giving the title compound (1.33 g, 40%) as a grey powder.

$^1$H NMR (250 MHz, d$^6$DMSO) δ(ppm): 13.0 (vb), 10.38 (s, 1H), 8.00 (d, 2H), 7.55 (m, 2H), 7.46 (d, 2H), 7.21 (d, 1H), 4.27 (s, 2H), 2.23 (s, 3H).

Description 117
5-(4-Bromo-3-methylphenyl)-2-furaldehyde

Using a method similar to that of Davis and Lougheed (*J. Het. Chem.* 1976, 4(1), 153–4), 4-bromo-3-methylaniline (20 g, 0.107 mol) was converted to the title compound as an orange powder (2.93 g, 10%).

$^1$H NMR (200 MHz, CDCl$_3$) δ(ppm): 9.64 (s, 1H), 7.7 (s, 1H), 7.6 (d, 1H), 7.48 (d, 1H), 7.3 (d, 1H), 6.82 (d, 1H), 2.45 (s, 3H).

Description 118
5-(4-Bromo-3-methylphenyl)-2-methylfuran

Using a method similar to that of Oleinik et al (*Khim-Farm. Zh.*, 1971 5(7) 19–22), 5-(4-bromo-3-methylphenyl)-2-furaldehyde (D117) (1.5 g, 5.66 mmol) was converted to the title compound as a yellow powder (1.12 g, 79%).

$^1$H NMR (200 MHz, CDCl$_3$) δ(ppm): 7.55–7.41 (m, 2H), 7.29 (d, 1H), 6.5 (d, 1H), 6.06 (m, 1H), 2.4 (s, 3H), 2.35 (s, 3H).

Description 119
2'-Methyl-4'-(5-methylfuran-2-yl)biphenyl-4-carboxylic acid 5-(4-Bromo-3-methylphenyl)-2-methylfuran (D118) (600 mg, 2.39 mmol) and 4-boronobenzoic acid (397 mg, 2.39 mmol) were converted to the title compound using a method similar to that of Description 11, as a pale yellow solid (207 mg, 30%).

$^1$H NMR (200 MHz, d$^6$DMSO) δ(ppm): 13.0 (br s, 1H), 8.0 (d, 2H), 7.65–7.44 (m, 4H), 7.25 (d, 1H), 6.86 (d, 1H), 6.2 (d, 1H), 2.35 (s, 3H), 2.28 (s, 3H).

EXAMPLE 1
1'-Methyl-5-(2'-methyl-4'-(5-methyl-1,2,4-oxadiazol-3-yl) biphenyl-4-carbonyl)-2,3,6,7-tetrahydrospiro[furo[2,3-f] indole-3,4'-piperidine]

A stirred solution of 2'-methyl-4'-(5-methyl-1,2,4-oxadiazol-3-yl)biphenyl-4-carboxylic acid (EP 0533268 A1) (36 mg, 0.12 mmol) in thionyl chloride (3ml) was heated at reflux under argon for 20 minutes, then concentrated in vacuo to leave the acid chloride as a yellow solid. This was dissolved in dichloromethane (2 ml) and added to a stirred solution of 1'-methyl-2,3,6,7-tetrahydrospiro[furo[2,3-f] indole-3,4'-piperidine] (D8, 30 mg, 0.12 mmol) and triethylamine (0.06 ml, 0.43 mmol) in dichloromethane (2 ml) and kept at room temperature for 3 days. The mixture was washed with aq K$_2$CO$_3$ solution and brine, then dried (Na$_2$SO$_4$) and concentrated in vacuo. The residue was chromatographed on silica gel eluting with 0 to 11% methanol/dichloromethane to afford the title compound as a colourless gum (19 mg, 30%). This was converted to its oxalate (mp 232° C.) and hydrochloride (mp>250° C.) salts.

$^1$H NMR (oxalate salt) (400 MHz, d$^6$DMSO) δ(ppm): 7.95–7.85 (m, 3H), 7.62 (d, 2H), 7.47 (d, 2H), 7.39 (d, 1H), 6.72 (s, 1H), 4.44 (s, 2H), 4.01 (t, 2H), 2.99 (t, 2H), 2.90 (m), 2.66 (m), 2.64 (s, 3H), 2.31 (s, 3H), 2.02 (m, 2H), 1.84 (m, 2H)

EXAMPLE 2
2,3,5,6,7,8-Hexahydro-1'-methyl-5-(2'-methyl-4'-(5-methyl-1,2,4-oxadiazol-3-yl)biphenyl-4-carbonyl)spiro [furo[2,3-g]quinoline-3,4'-piperidine]

The title compound was prepared from 2,3,5,6,7,8-hexahydro-1'-methylspiro[furo[2,3-g]quinoline-3,4'-piperidine] (D10), using a procedure similar to that of Example 1, in 87% yield. The oxalate salt was precipitated from acetone by addition of ether, as a white powder.

$^1$H NMR (oxalate salt) (250 MHz, d$^6$DMSO) δ(ppm): 7.9 (m, 2H), 7.3 (m, 5H), 6.68 (s, 1H), 6.5 (b, 1H), 4.34 (s, 2H), 3.80 (m, 2H), 3.12 (m, 2H), 2.9–2.6 (m, 12H), 2.29 (s, 3H), 1.97 (t, 2H), 1.60 (m, 4H).

EXAMPLE 3
5-(2'-Methyl-4'-(5-methyl-1,2,4-oxadiazol-3-yl)biphenyl-4-carbonyl)-2,3,6,7-tetrahydrospiro[furo[2,3-f]indole-3,4'-piperidine]

A stirred solution of 1'-methyl-5-(2'-methyl-4'-(5-methyl-1,2,4-oxadiazol-3-yl)biphenyl-4-carbonyl)-2,3,6,7-tetrahydrospiro[furo[2,3-f]indole-3,4'-piperidine] (E1, 350 mg, 0.67 mmole) in 1,2-dichloroethane (15 ml) under argon was treated with diisopropylethylamine (0.14 ml, 0.80 mmole) and 1-chloroethyl chloroformate (0.09 ml, 0.80 mmole). The mixture was stirred at room temperature for 2 h followed by 1 h at reflux temperature. Additional diisopropylethylamine (0.10 ml, 0.57 mmole) and 1-chloroethyl chloroformate (0.06 ml, 0.53 mmole) was added and reaction maintained at reflux for a further 1 h. The solution was concentrated in vacuo and the residue treated with methanol (20 ml) and heated under reflux for 1 h. The solution was concentrated in vacuo and the residue treated with conc. $K_2CO_3$ solution (25 ml) and chloroform (25 ml), shaken well and the chloroform solution separated, dried ($Na_2SO_4$) and concentrated in vacuo to afford the title compound as a beige solid (340 mg, 100%). The hydrochloride salt was prepared from acetone/ether as a white solid mp 203–210° C.

$^1$H NMR (free base) (250 MHz, $CDCl_3$) δ(ppm): 8.12 (br s, 1H—low integration, 8.00 (s, 1H), 7.95 (d, 1H), 7.62 (d, 2H), 7.43 (d, 2H), 7.35 (d, 1H), 6.68 (s, 1H), 4.45 (br s, 2H), 4.30–3.95 (br m, 4H), 3.40–3.15 (br, 2H), 3.08 (t 2H), 2.90–2.72 (br, 2H), 2.68 (s, 3H), 2.35 (s, 3H), 2.15–1.95 (br, 2H), 1.90–1.70 (br, 3H).

EXAMPLE 4

1'-Ethyl-5-(2'-methyl-4'-(5-methyl-1,2,4-oxadiazol-3-yl) biphenyl-4-carbonyl)-2,3,6,7-tetrahydrospiro[furo[2,3-f] indole-3,4'-piperidine]

A stirred solution of 5-(2'-methyl-4'-(5-methyl-1,2,4-oxadiazol-3-yl)biphenyl-4-carbonyl)-2,3,6,7-tetrahydrospiro[furo[2,3-f]indole-3,4'-piperidine] (E3, 100 mg, 0.20 mmole) in glacial acetic acid (2 ml) at room temperature under argon was carefully treated with sodium borohydride pellets (50 mg, 1.3 mmole) and stirred for 24 H. Additional sodium borohydride pellets were added (50 mg, 1.3 mmole) and reaction mixture stirred at room temperature for a further 72 h. The reaction mixture was then treated with water (20 ml), basified with 10% NaOH solution (20 ml) and extracted with dichloromethane. The extract was dried ($Na_2SO_4$), concentrated in vacuo and the residue chromatographed on silica gel eluting with 3% $MeOH/CHCl_3$. Crystallisation of the product form ethyl acetate/60–80 petrol afforded the title compound as a white solid (55 mg, 52%) mp 202–204° C.

$^1$H NMR (250 MHz, $CDCl_3$) δ(ppm): 8.17 (br s, 1H—low integration), 8.00 (s, 1H), 7.95 (d, 1H), 7.62 (d, 2H), 7.42 (d, 2H), 7.36 (d, 1H), 6.67 (s, 1H), 4.40 (br s, 2H), 4.10 (br s, 2H), 3.07 (t, 2H), 3.10–2.80 (br m, 2H), 2.68 (s, 3H), 2.55–2.30 (br m, 2H), 2.35 ls, 3H), 2.25–1.50 (br, m, 6H), 1.10 (br t, 3H)

EXAMPLE 5

1'-Methyl-5-(2'-methyl-4'-(5-methyl-1,3,4-oxadiazol-2-yl) biphenyl-4-carbonyl)-2,3,6,7-tetrahydrospiro[furo[2,3-f] indole-3,4'-piperidine]

The title compound was prepared from 1'-methyl-2,3,6, 7-tetrahydrospiro[furo[2,3-f]indole-3,4'-piperidine] (D8) and 2'-methyl-4'-(5-methyl-1,3,4-oxadiazol-2-yl)biphenyl-4-carboxylic acid (D11) using a procedure similar to that of Example 1 (23%). This was converted to the oxalate salt which precipitated from acetone/ether as a white solid (mp 232–235° C.), and hydrochloride salt (mp>250° C.).

$^1$H NMR (oxalate salt) (250 MHz, d$^6$DMSO) δ(ppm): 7.98–7.80 (m, 3H), 7.72–7.65 (m, 2H), 7.58–7.49 (m, 3H), 6.80 (s, 1H), 4.51 (s, 2H), 4.11–4.04 (m, 4H), 3.09–3.01 (m, 2H), 2.85–2.78 (m, 4H), 2.61 (s, 2H), 2.61–2.55 (m, 2H), 2.50 (s, 3H), 2.38 (s, 3H)

EXAMPLE 6

5-(4'-(5-Dimethylamino-1,2,4-oxadiazol-3-yl)-2'-methylbiphenyl-4-carbonyl)-1'-methyl-2,3,6,7-tetrahydrospiro[furo[2,3-f]indole-3,4'-piperidine]

The title compound was prepared from 1'-methyl-2,3,6, 7-tetrahydrospiro [furo[2,3-f]indole-3,4'-piperidine] (D8) and 4'-(5-dimethylamino-1,2,4-oxadiazol-3-yl)-2'-methylbiphenyl-4-carboxylic acid (D14) using a procedure similar to that of Example 1 (18%). This was converted to the oxalate salt, which precipitated from acetone/ether as a white solid.

$^1$H NMR (free base) (200 MHz, $CDCl_3$) δ(ppm): 8.15 (br s, 1H), 7.96–7.84 (m, 2H), 7.62 (d, 2H), 7.42 (d, 2H), 7.32 (d, 1H), 6.69 (s, 1H), 4.40 (br s, 2H), 4.20–4.00 (br m, 2H), 3.24 (s, 6H), 3.08 (t, 2H), 2.97–2.77 (br m, 2H), 2.34 (s, 6H), 2.18–1.59 (br m, 6H)

EXAMPLE 7

1'-Methyl-5-[4'-(5-methyl-1,2,4-oxadiazol-3-yl)biphenyl-4-carbonyl]-2,3,6,7-tetrahydrospiro[furo[2,3-f]indole-3,4'-piperidine]

The title compound was prepared from 1'-methyl-2,3,6, 7-tetrahydrospiro [furo[2,3-f]indole-3,4'-piperidine] (D8) and 4'-(5-methyl-1,2,4-oxadiazol-3-yl)biphenyl-4-carboxylic acid (D15), using a procedure similar to that of Example 1 (57%).

$^1$H NMR (250 MHz, $CDCl_3$) δ(ppm): 8.17 (d, 3H), 7.79–7.62 (m, 6H), 6.67 (s, 1H), 4.40 (br s, 2H), 4.15–4.00 (br m, 2H), 3.08 (t, 2H), 3.00–2.80 (br m, 2H), 2.70 (s, 3H), 2.48–1.45 (br m, 9H)

EXAMPLE 8

2,3-Dihydro-1'-methyl-5-(2'-methyl-4'-(5-methyl-1,2,4-oxadiazol-3-yl)biphenyl-4-carbonyl)spiro[furo[2,3-f] indole-3,4'-piperidine)

A stirred suspension of 2'-methyl-4'-(5-methyl-1,2,4-oxadiazol-3-yl)biphenyl-4-carboxylic acid (EP 0533268A1) (315 mg, 1.1 mmole) in thionyl chloride (10 ml) was heated under reflux for 0.5 h, then concentrated in vacuo to leave the acid chloride as a yellow solid. A stirred solution of 2,3-dihydro-1'-methylspiro[furo[2,3-f]indole-3,4'-piperidine] (D7, 260 mg, 1.1 mmole) in dry THF (10 ml) at room temperature under argon was treated with potassium t-butoxide (125 mg, 1.1 mmole) and stirred for 0.25 h, then treated with a solution of the above acid chloride (1.1 mmole) in dry THF (5 ml). The mixture was stirred at room temperature for 2 h, then concentrated in vacuo and the residue treated with 10% $Na_2CO_3$ solution and extracted with ethyl acetate. The extract was dried ($Na_2SO_4$), concentrated in vacuo and the residue chromatographed on silica gel eluting with 3% $MeOH/CHCl_3$. The pale yellow oil obtained was further purified by preparative TLC on a silica gel plate eluting with 10% $MeOH/CHCl_3$ to afford the title compound (80 mg, 14%), which crystallised from ether mp 196–198° C.

$^1$H NMR (250 MHz, $CDCl_3$) δ(ppm): 8.33 (s, 1H), 8.03 (s, 1H), 7.98 (d, 1H), 7.80 (d, 2H), 7.50 (d, 2H), 7.38 (d, 1H), 7.29 (d, 1H), 6.96 (s, 1H), 6.54 (d, 1H), 4.46 (s, 2H), 3.00–2.87 (m, 2H), 2.70 (s, 3H), 2.38 (s, 3H), 2.36 (s, 3H), 2.25–1.97 (m, 4H), 1.90–1.78 (m, 2H)

EXAMPLE 9

5-[4'-Cyano-2'-methylbiphenyl-4-carbonyl]-1'-methyl-2,3, 6,7-tetrahydrospiro[furo[2,3-f]indole-3,4'-piperidine]

A stirred suspension of 4'-cyano-2'-methylbiphenyl-4-carboxylic acid (D16) (0.3 g, 1.3 mmole) in dichloromethane (10 ml) at room temperature under argon was treated with oxalyl chloride (0.12 ml, 1.43 mmole), followed by DMF (1 drop). The mixture was stirred for 2 h, then concentrated in vacuo to leave the acid chloride as a pale yellow solid. This was dissolved in dry THF (8 ml) and added to a stirred solution of 1'-methyl-2,3,6,7-tetrahydrospiro[furo[2,3-f]indole-3,4'-piperidine] (D8) (0.3 g, 1.3 mmole) and triethylamine (0.35 ml, 2.6 mmole) in dry THF (10 ml) at 5° C. under argon. The reaction mixture was allowed to warm to room temperature and then concentrated in vacuo. The residue was taken up in 10% $Na_2CO_3$ solution (20 ml) and extracted with EtOAc (2×30 ml). The combined extract was dried ($Na_2SO_4$) concentrated in vacuo and the residue chromatographed on silica gel eluting with 1% methanol/dichloromethane to give the title compound (0.2 g, 34%) as a white solid.

$^1$H NMR (250 MHz, $CDCl_3$) δ(ppm): 8.14 (br s, 1H-low integration), 7.68–7.52 (m, 4H), 7.39–7.32 (m, 3H), 6.68 (s, 1H), 4.40 (br s, 2H), 4.18–3.99 (br m, 2H), 3.08 (t, 2H), 2.94–2.79 (br m, 2H), 2.31 (s, 6H), 2.12–1.71 (br m, 6H)

EXAMPLE 10

5-(4'-Acetyl-2'-methylbiphenyl-4-carbonyl)-1'-methyl-2,3,6,7-tetrahydrospiro[furo[2,3-f]indole-3,4'-piperidine]

The title compound was prepared from 1'-methyl-2,3,6,7-tetrahydrospiro[furo[2,3-f]indole-3,4'-piperidine] (D8) and 4'-acetyl-2'-methylbiphenyl-4-carboxylic acid (D19) using a procedure similar to that of Example 1 (35%).

$^1$H NMR (250 MHz, $CDCl_3$) δ(ppm): 8.13 (br s, 1H-low integration). 7.92–7.80 (m, 2H), 7.62 (d, 2H), 7.42–7.28 (m, 3H). 6.68 (s, 1H), 4.40 (s, 2H), 4.20–4.00 (m, 2H), 3.08 (t, 2H), 2.97–2.80 (m, 2H), 2.60 (s, 3H), 2.45–1.54 (m, 12H)

EXAMPLE 11

5-(4'-(1-(Methoxyamino)ethyl)-2'-methylbiphenyl-4-carbonyl)-1'-methyl-2,3,6,7-tetrahydrospiro[furo[2,3-f]indole-3,4'-piperidine]

Methoxylamine hydrochloride (0.06 g, 0.7 mmol) was added to a stirred solution of potassium t-butoxide (0.06 g, 0.5 mmol) in methanol (10 ml) under argon. After 20 minutes at room temperature, the solution was treated with a solution of 5-(4'-acetyl-2'-methylbiphenyl-4-carbonyl)-1'-methyl-2,3,6,7-tetrahydrospiro[furo[2,3-f]indole-3,4'-piperidine] (E10, 0.16 g, 0.3 mmole) in methanol (10 ml) and stirred at room temperature for 18 hours, followed by 1 hour heating under reflux. The solution was allowed to cool, treated with 10% $Na_2CO_3$ solution (40 ml) and extracted with ethyl acetate. The extract was dried ($Na_2SO_4$) and concentrated in vacuo to afford the title compound as a yellow solid (0.16 g, 94%).

$^1$H NMR (250 MHz, $CDCl_3$) δ(ppm); 8.12 (br s, 1H-low integration), 7.62–7.48 (m, 4H), 7.40 (d, 2H), 7.25 (d, 1H), 6.69 (s, 1H), 4.40 (s, 2H), 4.18–4.04 (m, 2H), 4.03 (s, 3H), 3.07 (t, 2H), 2.94–2.89 (m, 2H), 2.31 (s, 6H), 2.26 (s, 3H), 2.13–1.52 (m, 6H)

EXAMPLE 12

5-(4'-Acetamidomethyl-2'-methylbiphenyl-4-carbonyl)-1'-methyl-2,3,6,7-tetrahydrospiro[furo[2,3-f]indole-3,4'-piperidine]

A stirred solution of 1'-methyl-2,3,6,7-tetrahydrospiro[furo[2,3-f]indole-3,4'-piperidine] (D8, 85 mg, 0.35 mmole) in toluene (10 ml) at room temperature under argon was treated with 2M trimethylaluminium in hexane (0.74 ml, 1.5 mmole). The mixture was stirred for 0.75 h, then treated with a solution of methyl 4'-acetamidomethyl-2'-methylbiphenyl-4-carboxylate (D21, 120 mg, 0.40 mmole) in toluene (5 ml) and heated at 90° C. for 2 h. The solution was allowed to cool, then poured carefully into a stirred slurry of silica gel (10 g) in dichloromethane (30 ml) and stirring continued until the effervescence had ceased. The silica gel slurry was then packed into a chromatography column and eluted with 0–10% MeOH/$CH_2Cl_2$ to afford the title compound (85 mg, 48%). This was converted to the oxalate salt, which crystallised form acetone.

$^1$H NMR (free base) (250 MHz, $CDCl_3$) δ(ppm): 8.13 (br s, 1H-low integration), 7.58 (d, 2H), 7.35 (d, 2H), 7.25–7.13 (m, 3H), 6.67 (s, 1H), 5.95 (br t, 1H), 4.46 (d, 2H), 4.38 (br s, 2H), 4.20–4.00 (br, 2H), 3.05 (t, 2H), 2.95–2.75 (br, 2H), 2.31 (s, 3H), 2.27 (s, 3H), 2.20–1.50 (br m, 6H), 2.05 (s, 3H).

EXAMPLE 13

3,5,6,7,8,9-Hexahydro-1'-methyl-5-(2'-methyl-4'-(5-methyl-1,2,4-oxadiazol-3-yl)biphenyl-4-carbonyl)spiro[2H-furo[2,3-h]benzazepine-3,4'-piperidine]

The title compound was prepared from 3,5,6,7,8,9-hexahydro-1'-methylspiro[2H-furo[2,3-h]benzazepine-3,4'-piperidine] (D28), using a procedure similar to that of Example 1. The oxalate salt was precipitated from acetone by addition of ether, as a white solid.

$^1$H NMR (oxalate salt) (250 MHz, $d^6$DMSO) δ(ppm): 7.9 (m, 2H), 7.4–7.2 (m, 5H), 6.72 (s, 1H), 6.61 (b, 1H), 4.73 (d, 1H), 4.42 and 4.28 (ABq, 2H), 3.31 (m, 1H), 3.1–2.7 (m, 6H), 2.69 (s, 3H), 2.67 (s, 3H), 2.20 (s, 3H), 2.3–1.7 (m, 5H), 1.5–1.2 (m, 3H)

EXAMPLE 14

1'-Methyl-5-(2'-methyl-4'-(3-methyl-1,2,4-oxadiazol-5-yl)biphenyl-4-carbonyl)-2,3,6,7-tetrahydrospiro[furo[2,3-f]indole-3,4'-piperidine]

The title compound was prepared from 1'-methyl-2,3,6,7-tetrahydrospiro [furo[2,3-f]indole-3,4'-piperidine] (D8) and 2'-methyl-4'-(3-methyl-1,2,4-oxadiazol-5-yl)biphenyl-4-carboxylic acid (D29) using a similar procedure to Example 1. This was converted to its oxalate salt, which was obtained as a yellow solid (3%).

$^1$H NMR (free base) (200 MHz, $CDCl_3$) δ(ppm): 8.15 (br s, 1H-low integration), 8.06 (s, 1H), 8.00 (d, 1H), 7.62 (d, 2H), 7.48–7.33 (m, 3H), 6.66 (s, 1H), 4.40 (br s, 2H), 4.10 (br, 2H), 3.06 (t, 2H), 2.85 (br, 2H), 2.50 (s, 3H), 2.36 (s, 3H), 2.30 (br s, 3H), 2.15–1.70 (m, 6H).

EXAMPLE 15

1'-Methyl-5-(2'-methyl-4'-(1,3,4-oxadiazol-2-yl)biphenyl-4-carbonyl)-2,3,6,7-tetrahydrospiro[furo[2,3-f]indole-3,4'-piperidine A stirred suspension of 5-(4'-hydroazinocarbonyl-2'-methylbiphenyl-4-carbonyl)-1'-methyl-2,3,6,7-tetrahydrospiro[furo[2,3-f]indole-3,4'-piperidine] (E25) (150 mg, 0.3 mmol) in triethyl orthoformate (10 ml) was heated at reflux for 2 h. The mixture cooled, concentrated in vacuo and chromatographed on silica gel, eluting with methanol and chloroform to give the title compound as a white foam (24 mg, 16%). This was converted to its oxalate salt which was obtained as a white solid (mp 242–244° C.) and hydrochloride salt (mp 298–302° C.).

$^1$H NMR (free base) 200 MHz, $CDCl_3$) δ(ppm): 8.5 (s, 1H), 8.25–7.92 (m, 3H), 7.70–7.57 (m, 2H), 7.50–7.35 (m, 3H), 6.68 (s, 1H), 4.38 (br s, 2H), 4.20–4.00 (br m, 2H), 3.08 (t, 2H), 2.97–2.70 (m, 2H), 2.38 (s, 3H), 2.31 (s, 3H), 2.20–1.50 (m, 6H)

EXAMPLE 16

5-[4'-(5-Ethyl-1,3,4-oxadiazol-2-yl)-2'-methylbiphenyl-4-carbonyl]-1'-methyl-2,3,6,7-tetrahydrospiro[furo[2,3-f]indole-3,4'-piperidine]

The title compound was afforded as a white solid (54%) from 4'-(5-ethyl-1,3,4-oxadiazol-2-yl)-2'-methylbiphenyl-4- carboxylic acid (D32) and 1'-methyl-2,3,6,7-tetrahydrospiro[furo[2,3-f]indole-3,4'-piperidine] (D8) as per method of Example 1. This was converted to its oxalate salt.

$^1$H NMR (oxalate salt) (400 MHz, d$^6$DMSO) δ(ppm): 7.95 (m, 2H), 7.90 (d, 1H), 7.66 (m, 2H), 7.51 (m, 3H), 6.78 (s, 1H), 4.50 (s, 2H), 4.05 (t, 2H), 3.40 (b, 2H), 3.00 (m, 6H), 2.77 (s, 3H), 2.38 (s, 3H), 2.10 (b, 2H), 1.87 (b, 2H), 1.34 (t, 3H).

EXAMPLE 17
5-[2'-Methyl-4'-(5-methyl-1,3,4-oxadiazol-2-yl)biphenyl-4-carbonyl]-2,3,6,7-tetrahydrospiro[furo[2,3-f]indole-3,4'-piperidine]

The title compound was prepared from 1'-methyl-5-[2'-methyl-4'-(5-methyl-1,3,4-oxadiazol-2-yl)biphenyl-4-carbonyl]-2,3,6,7-tetrahydrospiro [furo[2,3-f]indole-3,4'-piperidine] (E5) following a similar procedure to Example 3 (100%). This was converted to the oxalate salt, which precipitated from acetone/ether as a pale yellow solid.

$^1$H NMR (oxalate salt) (200 MHz, CDCl$_3$) δ (ppm): 8.00–7.85 (m, 3H), 7.65 (d, 2H), 7.55–7.42 (m, 3H), 6.78 (s,1H), 4.50 (s, 2H), 4.05 (t, 2H), 3.03 (t, 2H), 2.61 (s, 3H), 2.37 (s, 3H), remaining signals not discernable from spectrum.

EXAMPLE 18
2,3-Dihydro-1'-methyl-5-(2'-methyl-4'-(5-methyl-1,3,4-oxadiazol-2-yl)biphenyl-4-carbonyl)spiro[furo[2,3-f]indole-3,4'-piperidine]

The title compound was prepared from 2,3-dihydro-1'-methylspiro[furo[2,3-f]indole-3,4'-piperidine] (D7) and 2'-methyl-4'-(5-methyl-1,3,4-oxadiazol-2-yl)biphenyl-4-carboxylic acid (D11) using a similar procedure to Example 8 (22%). This was converted to its oxalate salt, which crystallised from acetone/methanol as a white solid mp 234–237° C.

$^1$H NMR (free base) (200 MHz, CDCl$_3$) δ (ppm): 8.33 (s, 1H), 8.02 (s, 1H), 7.94 (d, 1H), 7.81 (d, 2H), 7.50 (d, 2H), 7.40 (d, 1H), 7.28 (d, 1H), 6.97 (s, 1H), 6.55 (d, 1H), 4.46 (s, 2H), 2.98–2.85 (m, 2H), 2.65 (s, 3H), 2.39 (s, 3H), 2.36 (s, 3H), 2.25–1.95 (m, 4H), 1.90–1.75 (m, 2H).

EXAMPLE 19
5-(2,2'-Dimethyl-4'-(5-methyl-1,3,4-oxadiazol-2-yl)biphenyl-4-carbonyl)-4'-methyl-2,3,6,7-tetrahydrospiro[furo[2,3-f]indole-3,4'-piperidine]

The title compound was prepared from 1'-methyl-2,3,6,7-tetrahydrospiro [furo[2,3-f]indole-3,4'-piperidine] (D8) and 2,2'-dimethyl-4'-(5-methyl-1,3,4-oxadiazol-2-yl)biphenyl-4-carboxylic acid (D34) using a similar procedure to Example 1 (53%). This was converted to its oxalate salt and crystallised from acetone/methanol as a white solid mp 222–224° C.

$^1$H NMR (free base) (200 MHz, CDCl$_3$) δ (ppm): 8.13(br s, 1H), 7.98 (s, 1H), 7.90 (dd, 1H), 7.48 (s, 1H), 7.41 (d, 1H), 7.35–7.20 (m, 1H), 7.16 (d, 1H), 6.66 (s, 1H), 4.38 (br s, 2H), 4.10 (br, 2H), 3.07 (t, 2H), 2.85 (br, 2H), 2.64 (s, 3H), 2.32 (s, 3H), 2.20–1.70 (m, 6H), 2.15 (s, 3H), 2.08 (s, 3H).

EXAMPLE 20
5-(2,3'-Dimethyl-4'-(5-methyl-1,3,4-oxadiazol-2-yl)biphenyl-4-carbonyl)-1'-methyl-2,3,6,7-tetrahydrospiro[furo[2,3-f]indole-3,4'-piperidine]

The title compound was prepared from 1'-methyl-2,3,6,7-tetrahydrospiro [furo[2,3-f]indole-3,4'-piperidine] (D8) and 2,3'-dimethyl-4'-(5-methyl-1,3,4-oxadiazol-2-yl)biphenyl-4-carboxylic acid (D36) using a similar procedure to Example 1 (31%). This was converted to its oxalate salt and crystallised from acetone/methanol as a pale yelloe solid mp. 193–195° C.

$^1$H NMR (free base) (250 MHz, CDCl$_3$) δ (ppm): 8.14 (br s, 1H), 7.97 (d, 1H), 7.48 (s, 1H), 7.42 (d, 1H), 7.37–7.25 (m, 3H), 6.67 (s, 1H), 4.40 (br, s, 2H), 4.08 (br s, 2H), 3.06 (t, 2H), 2.87 (br, 2H), 2.77 (s, 3H), 2.65 (s, 3H), 2.32 (s, 6H), 2.20–1.90 (m, 4H), 1.85–1.60 (m, 2H).

EXAMPLE 21
1'-Methyl-5-(2'-methyl-4'-(4-methylthiazol-2-yl)biphenyl-4-carbonyl)-2,3,6,7-tetrahydrospiro[furo[2,3-f]indole-3,4'-piperidine]

The title compound was prepared from 2'-methyl-4'-(4-methylthiazol-2-yl)biphenyl-4-carboxylic acid (D40) and 1'-methyl-2,3,6,7-tetrahydrospiro [furo[2,3-f]indole-3,4'-piperidine] (D8), following the procedure of Example 1. The oxalate salt crystallised from acetone as a buff powder.

$^1$H NMR (oxalate salt) (250 MHz, d$^6$DMSO) δ (ppm): 7.8–8.0 (m, 3H), 7.67 (d, 2H), 7.52 (d, 2H), 7.40 (m, 1H), 7.38 (s, 1H), 6.78 (s, 1H), 4.51 (s, 2H), 4.06 (t, 2H), 3.40 (m, 2H), 3.04 (t, 2H), 3.0 (m, 2H), 2.77 (s, 3H), 2.44 (s, 3H), 2.37 (s, 3H), 2.1 (m, 2H), 1.9 (m, 2H).

EXAMPLE 22
5-(4'-Methoxycarbonyl-2'-methylbiphenyl-4-carbonyl)-1'-methyl-2,3,6,7-tetrahydrospiro[furo[2,3-f]indole-3,4'-piperidine]

The title compound was prepared from 1'-methyl-2,3,6,7-tetrahydrospiro [furo[2,3-f]indole-3,4'-piperidine] (D8) and 4'-methoxycarbonyl-2'-methyl biphenyl-4-carboxylic acid (D41) using a procedure similar to that of Example 1 (76%).

$^1$H NMR (200 MHz, CDCl$_3$) δ (ppm): 8.12 (br s, 1H—low integration), 7.99 (s, 1H), 7.91 (d, 1H), 7.61 (d, 2H), 7.39 (d, 2H), 7.31 (d, 1H), 6.68 (s, 1H), 4.40 (s, 2H), 4.10 (br, 2H), 3.95 (s, 3H), 3.08 (t, 2H), 2.90 (br s, 2H), 2.34 (s, 6H), 2.20–1.65 (m, 6H)

EXAMPLE 23
5-(5'-Methoxycarbonyl-2'-methylbiphenyl-4-carbonyl)-1'-methyl-2,3,6,7-tetrahydrospiro[furo[2,3-f]indole-3,4'-piperidine]

The title compound was prepared from 1'-methyl-2,3,6, 7-tetrahydrospiro [furo[2,3-f]indole-3,4'-piperidine] (D8) and 5'-methoxycarbonyl-2'-methylbiphenyl-4-carboxylic acid (D42) using a similar procedure to Example 1 (51%).

$^1$H NMR(250 MHz, CDCl$_3$) δ (ppm): 8.12 (br s, 1H—low integration), 7.98–7.89 (m, 2H), 7.62 (d, 2H), 7.41–7.28 (m, 3H), 6.63 (s, 1H), 4.38 (br s, 2H), 4.09 (br s, 2H), 3.90 (s, 3H), 3.09 (t, 2H), 2.90 (br s, 2H), 2.32 (s, 6H), 2.20–1.62 (m, 6H).

EXAMPLE 24
5'-[4'-(Methanesulphonamino)-2'-methylbiphenyl-4-carbonyl]-1'-methyl-2,3,6,7-tetrahydrospiro[furo[2,3-f]indole-3,4'-piperidine]

The title compound was afforded as a white solid (38%) from 4'-(methane sulphonamino)-2'-methylbiphenyl-4-carboxylic acid (D44) as per method of Example 1 and converted to its oxalate salt.

$^1$H NMR (oxalate salt) (250 MHz, d$^6$DMSO) δ (ppm): 9.82 (b, 1H), 7.96 (b, 1H), 7.65 (d, 2H), 7.45 (d, 2H), 7.20 (m, 3H), 6.78 (s, 1H), 4.50 (s, 2H), 4.15 (t, 2H), 3.39 (m, 2H), 3.05 (m, 4H), 2.78 (s, 3H), 2.40–2.00 (b, 2H), 2.27 (s, 3H), 2.10 (s, 3H), 1.89 (m, 2H).

EXAMPLE 25

5'-(4'-Hydrazinocarbonyl-2'-methylbiphenyl-4-carbonyl)-1'-methyl-2,3,6,7-tetrahydrospiro[furo[2,3-f]indole-3,4'-piperidine]

A solution of 5'(4'-methoxycarbonyl-2'-methylbiphenyl-4-carbonyl)-1'-methyl-2,3,6,7-tetrahydrospiro[furo[2,3-f]indole-3,4'-piperidine] (E22, 0.75 g, 1.5 mmole) in methanol (25 ml) was treated with hydrazine monohydrate (1.05 ml) and heated under reflux for 18 h. The reaction mixture was allowed to cool, then poured into water (50 ml) and the solid which precipitated out was filtered off and dried (0.61 g, 81%). A 50 mg portion was purified by preparative TLC on silica gel eluting with 20% methanol/chloroform to afford the title compound as a white solid mp. 130–135° C.

$^1$H NMR (250 MHz, CDCl$_3$+CD$_3$OD) δ (ppm): 8.11 (br s, 1H), 7.75 (s, 1H), 7.67 (dd, 1H), 7.62 (d, 2H), 7.42 (d, 2H), 7.31 (d, 1H), 6.70 (s, 1H), 4.40 (br s, 2H), 4.12 (br t, 2H), 3.10 (t, 2H), 2.94 (br, 2H), 2.38 (br s, 3H), 2.33 (s, 3H), 2.30–2.00 (m, 4H), 1.90–1.70 (m, 2H).

EXAMPLE 26

1'-Ethyl-5-[2'-methyl-4'-(5-methyl-1,3,4-oxadiazol-2-yl)biphenyl-4-carbonyl]-2,3,6,7-tetrahydrospiro[furo[2,3-f]indole-3,4'-piperidine]

A stirred suspension of 2'-methyl-4'-(5-methyl-1,3,4-oxadiazol-2-yl)biphenyl-4-carboxylic acid (D11, 0.53 g, 1.8 mmole) in thionyl chloride (8 ml) was heated at about 45° C. for 30 minutes, then concentrated in vacuo. The yellow solid was dissolved in THF (10 ml)/dichloromethane (5 ml) and added to a stirred solution of 1'-ethyl-2,3,6,7-tetrahydrospiro[furo[2,3-f]indole-3,4'-piperidine] (D109, 0.46 g, 1.8 mmole) and triethylamine (0.50 ml, 3.6 mmole) in THF (15 ml) at 5° C. under argon. The solution was stirred at room temp. for 2 h, then concentrated in vacuo. The residue was treated with 10% Na$_2$CO$_3$ solution and extracted with ethyl acetate. The extract was dried (Na$_2$SO$_4$), concentrated in vacuo and the residue chromatographed on silica gel eluting with 3% methanol/chloroform and the yellow oil obtained passed through a short basic alumina column eluting with ethyl acetate to afford the title compound as a beige foam (0.62 g, 68%). This was converted to its hydrochloride (mp 269–273° C.) and mesylate (mp 275–279° C.) salts.

$^1$H NMR (free base) (250 MHz, CDCl$_3$) δ (ppm): 8.18 (br s, 1H—low integration), 7.98 (d, 1H), 7.91 (dd, 1H), 7.63 (d, 2H), 7.42 (d, 2H), 7.37 (d, 1H), 6.66 (s, 1H), 4.40 (br s, 2H), 4.10 (br m, 2H), 3.08 (t, 2H), 3.05–2.90 (br m, 2H), 2.65 (s, 3H), 2.55–2.35 (br m, 2H), 2.36 (s, 3H), 2.20–1.50 (m, 6H), 1.13 (br t, 3H).

EXAMPLE 27

1'-Methyl-5-(2'-methyl-5=-(5-methyl-1,3,4-oxadiazol-2-yl)biphenyl-4-carbonyl)-2,3,6,7-tetrahydrospiro[furo[2,3-f]indole-3,4'-piperidine]

The title compound was prepared from 2'-methyl-5'-(5-methyl-1,3,4-oxadiazol-2-yl)biphenyl-4-carboxylic acid (D45) and 1'-methyl-2,3,6,7-tetrahydrospiro[furo[2,3-f]indole-3,4'-piperidine] (D8) using a similar procedure to Example 1 as a brown oil (10%). This was converted to its oxalate salt which was obtained as a white solid.

$^1$H NMR (oxalate salt) (400 MHz, d$^6$DMSO)δ (ppm): 7.98 (br s, 1H), 7.91 (d, 1H), 7.80 (s, 1H), 7.68 (m, 2H), 7.58 (d, 1H), 7.54 (d, 2H), 6.77 (s, 1H), 4.50 (s, 2H), 4.07 (br t, 2H), 3.50–3.35 (br, 2H), 3.10–2.95 (m, 4H), 2.78 (s, 3H), 2.58 (s, 3H), 2.35 (s, 3H), 2.20–2.00 (m, 2H), 1.97–1.84 (m, 2H).

EXAMPLE 28

5-(4'-Carboxamido-2'-methylbiphenyl-4-carbonyl)-1'-methyl-2,3,6,7-tetrahydrospiro[furo[2,3-f]indole-3,4'-piperidine]

A suspension of 5-(4'-cyano-2'-methylbiphenyl-4-carbonyl)-1'-methyl-2,3,6,7-tetrahydrospiro[furo[2,3-f]indole-3,4'-piperidine] (E9) (130 mg, 0.28 mmol) in methanol (5 ml) was treated with 30% hydrogen peroxide (0.1 ml) and 20% sodium hydroxide solution (0.08 ml) and stirred at room temperature for 1.5 h. Sodium metabisulphite (60 mg) was added, the mixture was concentrated in vacuo and the residue was partitioned between water and ethyl acetate. The organic phase was dried (Na$_2$SO$_4$) and concentrated in vacuo and the resultant solid chromatographed on silica gel eluting with methanol and chloroform, to give the title compound as a white solid (50 mg, 37%).

$^1$H NMR (400 MHz, CDCl$_3$) δ (ppm): 7.75 (s, 1H), 7.65 (d, 1H), 7.60 (d, 2H), 7.4–7.35 (m, 2H), 7.3 (d, 1H), 6.64 (s, 1H), 5.8 (br s, 2H), 4.35 (s, 2H), 4.1 (t, 2H), 3.05 (t, 2H), 2.88–2.74 (m, 2H), 2.36–2.26 (m, 6H), 2.11–2.0 (m, 2H), 1.78–1.65 (m, 4H). (one aromatic proton not observed)

EXAMPLE 29

5-(4'-Acetamido-2'-methylbiphenyl-4-carbonyl)-1'-methyl-2,3,6,7-tetrahydrospiro[furo[2,3-f]indole-3,4'-piperidine]

The title compound was prepared from 4'-acetamido-2'-methylbiphenyl-4-carboxylic acid (D47) and 1'-methyl-2,3,6,7-tetrahydrospiro[furo[2,3-f]indole-3,4'-piperidine] (D8) following a similar procedure to Example 1 using oxalyl chloride in place of thionyl chloride, as a yellow oil (43%). This was converted to its oxalate salt which crystallised as a white solid from acetone.

$^1$H NMR (oxalate salt) (400 MHz, d$^6$DMSO) δ (ppm): 10.00 (s, 1H), 7.95 (br s, 1H), 7.62 (d, 2H), 7.55–7.50 (m, 2H), 7.43 (d, 2H), 7.19 (d, 1H), 6.77 (s, 1H), 4.50 (s, 2H), 4.05 (t, 2H), 3.40 (br, 2H), 3.08–2.93 (m, 4H), 2.75 (br s, 3H), 2.25 (s, 3H), 2.17–2.00 (m, 2H), 2.06 (s, 3H), 1.94–1.80 (m, 2H)

EXAMPLE 30

2,3,5,6,7,8-Hexahydro-1'-methyl-5-(2'-methyl-4'-(5-methyl-1,3,4-oxadiazol-2-yl)biphenyl-4-carbonyl)spiro[furo[2,3-g]quinoline-3,4'-piperidine]

The title compound was prepared from 2'-methyl-4'-(5-methyl-1,3,4-oxadiazol-2-yl)biphenyl-4-carboxylic acid (D11) and 2,3,5,6,7,8-hexahydro-1'-methylspiro[furo[2,3-g]quinoline-3,4'-piperidine] (D10) using a similar procedure to Example 1 as a white solid (62%). This was converted to its oxalate salt which was obtained as a white solid (mp 187–188° C.) and hydrochloride salt (mp 176–180° C.).

$^1$H NMR (free base) (200 MHz, CDCl$_3$) δ (ppm): 7.94 (s, 1H), 7.85 (d, 1H), 7.4–7.3 (m, 2H), 7.28–7.14 (m, 3H), 6.6 (s, 1H), 6.35 (br s, 1H), 4.26 (s, 2H), 3.94 (t, 2H), 2.78 (t, 2H), 2.71–2.55 (m, 5H), 2.3 (s, 3H), 2.25 (s, 3H), 2.14–1.75 (m, 4H), 1.61–1.41 (m, 4H)

EXAMPLE 31

2,3,5,6,7,8-Hexahydro-5-(4'-methanesulphonamino-2'-methylbiphenyl-4-carbonyl)-1'-methylspiro[furo[2,3-g]quinoline-3,4'-piperidine]

The title compound was prepared from 4'-(methanesulphonamino)2'-methylbiphenyl-4-carboxylic acid (D44) and 2,3,5,6,7,8-hexahydro-1'-methylspiro[furo[2,3-g]quinoline-3,4'-piperidine] (D10) using a similar procedure to Example 1 as a white solid (46%). This was converted to its oxalate salt which was obtained as a white powder. mp 165–170° C.

$^1$H NMR (free base) (200 MHz, CDCl$_3$) δ (ppm): 7.36–7.29 (m, 2H), 7.2–7.0 (m, 5H), 6.6 (s, 1H), 6.37 (br s, 1H), 4.25 (s, 2H), 3.92 (t, 2H), 3.03 (s, 3H), 2.77 (t, 2H), 2.7–2.55 (m, 2H), 2.25 (s, 3H), 2.2 (s, 3H), 2.12–1.78 (m, 4H), 1.57–1.41 (m, 4H) (one aromatic proton not observed)

EXAMPLE 32

1'-Methyl-5-[2'-methyl-4'-(5-methyl-1,2,4-oxadiazol-3-yl) biphenyl-4-carbonyl]-2,3,6,7-tetrahydrospiro[thiopheno[2, 3-f]indole-3,4'-piperidine]

1'-Methyl-2,3,6,7-tetrahydrospiro[thiopheno[2,3-f] indole-3,4'-piperidine] (D53) (0.029 g, 0.112 mmol) was transformed to give the title compound as a pale yellow oil (0.055 g, 93%) according to the method of Example 1.

$^1$H NMR (200 MHz, CDCl$_3$) δ (ppm): 8.00 (m, 3H), 7.62 (m, 2H), 7.40 (m, 3H), 7.05 (s, 1H), 4.12 (m, 2H), 3.30 (s, 2H), 3.08 (t, 2H), 2.85 (br s, 2H), 2.30 (s, 3H), 2.35 (s, 6H), 2.20 (br s, 4H), 1.85 (br s, 2H).

EXAMPLE 33

1,2,3,5,6,7-Hexahydro-1'-methyl-1-(2°-methyl-4'-(5'-methyl-1,3,4-oxadiazol-2-yl)biphenyl-4-carbonyl)spiro [indeno[5,6-b]pyrrole-7,4'-piperidine]

1,2,3,5,6,7-Hexahydro-1'-methylspiro[indeno[5,6-b] pyrrole-7,4'-piperidine] is prepared from 1-acetyl-2,3-dihydro-1H-indole-5-carboxaldehyde using a similar procedure to that described for compound 11 in Arch. Pharm. (Weinheim) 1991, 323, 35 and then converted to the title compound using a similar procedure to Example 1.

EXAMPLE 34

5-[4'-((N-Methanesulphonyl-N-methyl)amino)-2'-methylbiphenyl-4-carbonyl]-1'-methyl-2,3,6,7-tetrahydrospiro[furo[2,3-f]indole-3,4'-piperidine]

This was prepared from methyl 4'-[(N-methanesulphonyl-N-methyl)amino]-2'-methylbiphenyl-4-carboxylate (D54) following the procedure of Example 12. This gave the title compound as a white foam, which was converted into its oxalate salt, a light grey powder.

$^1$H NMR (oxalate salt) (250 MHz, d$^6$DMSO) δ (ppm): 7.97 (bs, 1H), 7.67 (d, 2H), 7.48 (d, 2H), 7.40 (s, 1H), 7.32 (m, 2H), 6.79 (s, 1H), 4.52 (s, 2H), 4.07 (t, 2H), 3.39 (m, 2H), 3.28 (s, 3H), 3.0 (m, 7H), 2.77 (s, 3H), 2.30 (s, 3H), 2.1 (m, 2H), 1.9 (m, 2H).

EXAMPLE 35

5-[4'-(Dimethylaminosulphonyl)biphenyl-4-carbonyl]-1'-methyl-2,3,6,7-tetrahydrospiro[furo[2,3-f]indole-3,4'-piperidine]

This was prepared from 4'-(dimethylaminosulphonyl) biphenyl-4-carboxylic acid (D56) following the procedure of Example 1. This gave the title compound (88%) as a yellowish foam, which was triturated in acetone to give a white powder.

$^1$H NMR (250 MHz, d$^6$DMSO) δ (ppm): 8.0 (m, 3H), 7.86 (m, 4H), 7.7 (m, 2H), 6.72 (s, 1H), 4.86 (s, 2H), 4.02 (t, 2H), 3.00 (t, 2H), 2.74 (b, 2H), 2.64 (s, 6H), 2.19 (s, 3H), 1.9 (m, 4H), 1.65 (m, 2H).

EXAMPLE 36

5-[4'-(Methanesulphonyl)biphenyl-4-carbonyl]-1'-methyl-2, 3,6,7-tetrahydrospiro[furo[2,3-f]indole-3,4'-piperidine]

This was prepared from 4'-(methanesulphonyl)biphenyl-4-carboxylic acid (D57), following the procedure of Example 1. This gave the title compound (73%) as a pale yellow foam, which was triturated with acetone/ether to give a white powder.

$^1$H NMR (250 MHz, d$^6$DMSO) δ (ppm): 8.02 (m, 5H), 7.87 (d, 2H), 7.72 (d, 2H), 6.71 (s, 1H), 4.37 (s, 2H), 4.03 (t, 2H), 3.28 (s, 3H), 3.01 (t, 2H), 2.75 (m, 2H), 2.20 (s, 3H), 1.9 (m, 4H), 1.65 (m, 2H).

EXAMPLE 37

5-[4'-(N,N-Dimethylcarbamoylamino)-2'-methylbiphenyl-4-carbonyl]-1'-methyl-2,3,6,7-tetrahydrospiro[furo[2,3-f] indole-3,4'-piperidine]

This was prepared from 4'-(N,N-dimethylcarbamoylamino)-2'-methylbiphenyl-4-carboxylic acid (D59), following the procedure of Example 9, but using dichloromethane as solvent throughout. This gave the title compound (35%) as a glass, which was converted to its oxalate salt, a cream solid.

$^1$H NMR (oxalate salt) (250 MHz, d$^6$DMSO) δ (ppm): 8.32 (s, 1H), 7.95 (b s, 1H), 7.61 (d, 2H), 7.45 (m, 4H), 7.12 (d, 1H), 6.77 (s, 1H), 4.46 (s, 2H), 4.05 (t, 2H), 3.3 (b, 2H), 3.1–2.9 (m, 4H), 2.93 (s, 6H), 2.69 (s, 3H), 2.23 (s, 3H), 2.05 (m, 2H), 1.85 (m, 2H).

EXAMPLE 38

5-[4'-(Ethoxycarbonylamino)-2'-methylbiphenyl-4-carbonyl]-1'-methyl-2,3,6,7-tetrahydrospiro[furo[2,3-f] indole-3,4'-piperidine]

This was prepared from 4'-(ethoxycarbonylamino)-2'-methylbiphenyl-4-carboxylic acid (D61), following the procedure of Example 9. This gave the title compound (75%) as a light yellow foam, which was converted to its hydrochloride salt, a white powder.

$^1$H NMR (HCl salt) (200 MHz, d$^6$DMSO) δ (ppm): 10.5 (b, 1H), 9.70 (s, 1H), 8.94 (b s, 1H), 7.62 (d, 2H), 7.43 (m, 4H), 7.18 (d, 1H), 6.78 (s, 1H), 4.51 (s, 2H), 4.14 (q, 2H), 4.-7 (t, 2H), 3.4 (m, 2H), 3.1 (m, 4H), 2.78 (s, 3H), 2.24 (s, 3H), 2.2 (m, 2H), 1.9 (m, 2H), 1.26 (t, 3H)

EXAMPLE 39

5-[4'-(4,5-Dimethyl-1,2,4-triazol-3-yl)-2'-methylbiphenyl-4-carbonyl]-1'-methyl-2,3,6,7-tetrahydrospiro[furo[2,3-f] indole-3,4'-piperidine]

This was prepared from 4'-(4,5-dimethyl-1,2,4-triazol-3-yl)-2'-methylbiphenyl-4-carboxylic acid (D64), following the procedure of Example 9. This gave the title compound (27%) as a white solid.

$^1$H NMR (200 MHz, CDCl$_3$) δ (ppm): 8.13 (b, 1H), 8.00 (s, 1H), 7.93 (d, 1H), 7.61 (d, 2H), 7.42 (d, 2H), 7.29 (d, 1H), 6.66 (s, 1H), 4.38 (s, 2H), 4.11 (b, 2H), 3.87 (s, 3H), 3.07 (t, 2H), 2.85 (m, 2H), 2.52 (s, 3H), 2.36 (s, 3H), 2.32 (s, 3H), 2.05 (m, 4H), 1.85 (m, 2H).

EXAMPLE 40

1'-Methyl-6-[2°-methyl-4'-(5-methyl-1,3,4-oxadiazol-2-yl) biphenyl-4-carbonyl]-2,3,7,8-tetrahydrospiro[4H-pyrano[2, 3-f]indole-4,4'-piperidine]

This was prepared from 1'-methyl-2,3,7,8-tetrahydrospiro [4H-pyrano[2,3-f]indole-4,4'-piperidine] (D70), following the procedure of Example 5. This gave the title compound (27%), which was converted to the oxalate salt, a white solid.

hu 1H NMR (oxalate salt) (400 MHz, d$^6$DMSO) δ (ppm): 7.96 (m, 2H), 7.89 (d, 1H), 7.69 (d, 2H), 7.54 (d, 2H), 7.48 (d, 1H), 6.94 (s, 1H), 4.32 (m, 1H), 4.07 (t, 2H), 3.65 (m, 2H), 3.38 (m, 2H), 3.06 (t, 2H), 3.0–3.2 (m, 2H), 2.85 (s, 3H), 2.61 (s, 3H), 2.38 (s, 3H), 1.92 (m, 2H), 1.5–1.75 (m, 3H)

EXAMPLE 41

1'-Methyl-5-(2'-methyl-4'-(5-methyl-1,3,4-thiadiazol-2-yl) biphenyl-4-carbonyl)-2,3,6,7-tetrahydrospiro[furo[2,3-f] indole-3,4'-piperidine]

Crude 2'-methyl-4'-(5-methyl-1,3,4-thiadiazol-2-yl) biphenyl-4-carboxylic acid (D73, 500 mg) and 1'-methyl-2, 3,6,7-tetrahydrospiro[furo[2,3-f]indole-3,4'-piperidine]

(D8) afforded the title compound according to the general method of Example 1. Preparative HPLC afforded 10 mg of pure compound.

$^1$H NMR (400 MHz, CD$_3$OD) δ (ppm): 8.02 (br s, 1H), 7.91 (s, 1H), 7.85 (d, 1H), 7.69 (d, 2H), 7.52 (d, 2H), 7.41 (d, 1H), 6.76 (s, 1H), 4.56 (s, 2H), 4.18 (t, 2H), 3.62–3.51 (m, 2H), 3.21–3.05 (m, 4H), 2.94 (s, 3H), 2.83 (s, 3H), 2.38 (s, 3H), 2.29–2.00 (m, 4H).

EXAMPLE 42
5-(2'-Methyl-4'-(5-methyl-1,3,4-oxadiazol-2-yl)biphenyl-4-carbonyl)-1'-n-propyl-2,3,6,7-tetrahydrospiro[furo[b2,3-f]indole-3,4'-piperidine]

1-Bromopropane (0.07 ml, 0.80 mmole) and sodium carbonate (226 mg, 2.13 mmole) weere added to a stirred solution of 5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine] (E3, 270 mg, 0.53 mmole) in ethanol (10 ml). This mixture was heated under reflux for 31 hours. The reaction mixture was concentrated in vacuo and the residue treated with water (15 ml) and extracted with chloroform. The organic extract was dried (Na$_2$SO$_4$), concentrated in vacuo and the residue chromatographed on silica gel eluting with 0–6% methanol/chloroform to afford the title compound as a yellow gum (194 mg, 67%). This was converted to its hydrochloride salt and crystallised from ether m.p. 263–266° C.

H$^1$ NMR (free base); (250 MHz, CDCl$_3$) δ (ppm): 8.15 (br s, 1H—low integration), 7.99 (s, 1H), 7.91 (dd, 1H), 7.64 (d, 2H), 7.42 (d, 2H), 7.37 (d, 1H), 6.67 (s, 1H), 4.40 (br s, 2H), 4.10 (br s, 2H), 3.07 (t, 2H), 2.94 (br s, 2H), 2.66 (s, 3H), 2.37 (s, 3H), 2.33 (br t, 2H), 2.22–1.38 (br m, 8H), 0.92 (t, 3H).

EXAMPLE 43
1'-Methyl-5-(2'-methyl-4'-(5-methyloxazol-2-yl)biphenyl-4-carbonyl)-2,3,6,7-tetrahydrospiro[furo[2,3-f]indole-3,4'-piperidine]

The title compound was prepared from 2'-methyl-4'-(5-methyloxazol-2-yl)biphenyl-4-carboxylic acid (D76) and 2,3,6,7-tetrahydrospiro[furo[2,3-f]indole-3,4'-piperidine] (D8) following the procedure of Example 1 (58%). This was converted to its oxalate salt and crystallised from acetone/methanol as a white solid m.p. 230–233° C.

$^1$H NMR (free base) (250 MHz, CDCl$_3$) δ (ppm): 8.14 (br s, 1H—low integration), 7.95 (s, 1H), 7.87 (d, 1H), 7.61 (d, 2H), 7.41 (d, 2H), 7.32 (d, 1H), 6.85 (s, 1H), 6.66 (s, 1H), 4.37 (br s, 2H), 4.10 (br m, 2H), 3.06 (t, 2H), 2.85 (br s, 2H), 2.42 (s, 3H), 2.35 (s, 3H), 2.31 (br s, 3H), 2.20–1.50 (m, 6H).

EXAMPLE 44
1'-Methyl-5-(2'-methyl-4'-(3-methylisoxazol-5-yl)biphenyl-4-carbonyl)-2,3,6,7-tetrahydrospiro[furo[2,3-f]indole-3,4'-piperidine]

The title compound was prepared from 1'-methyl-2,3,6,7-tetrahydrospiro [furo[2,3-f]indole-3,4'-piperidine] (D8) and 2'-methyl-4'-(3-methylisoxazol-5-yl)biphenyl-4-carboxylic acid (D79) using a procedure similar to that of Example 1 (58%) m.p. 224–5° C.

$^1$H NMR (250 MHz, CDCl$_3$) δ (ppm): 8.15 (br s, 1H), 7.72–7.55 (m, 4H), 7.45–7.24 (m, 3H), 6.67 (s, 1H), 6.4 (s, 1H), 4.38 (s, 2H), 4.20–4.0 (m, 2H), 3.07 (t, 2H), 2.95–2.71 (m, 2H), 2.37 (s, 3H), 2,32 (s, 6H), 2.2–1.5 (m, 6H).

EXAMPLE 45
1'-Methyl-5-(2'-methyl-4'-(5-methylisoxazol-3-yl)biphenyl-4-carbonyl)-2,3,6,7-tetrahydrospiro[furo[2,3-f]indole-3,4'-piperidine]

The title compound was prepared from 1'-methyl-2,3,6,7-tetrahydrospiro[furo[2,3-f]indole-3,4'-piperidine] (D8) and 2'-methyl-4'-(5-methylisoxazol-3-yl)biphenyl-4-carboxylic acid (D83) using a procedure similar to that of Example 1 (75%) m.p. 197–9° C.

$^1$H NMR (200 MHz, CDCl$_3$) δ (ppm): 8.15 (br s, 1H), 7.78–7.55 (m, 4H), 7.45–7.2 (m, 3H), 6.65 (s, 1H), 6.32 (s, 1H), 4.39 (s, 2H), 4.2–4.0 (m, 2H), 3.07 (t, 2H), 2.95–2.7 (m, 2H), 2.49 (s, 3H), 2.3 (s, 6H), 2.2–1.55 (m, 6H).

EXAMPLE 46
2,3,5,6,7,8-Hexahydro-1'-methyl-5-(4'-(5-dimethylamino-1,2,4-oxadiazol-3-yl)-2'-methylbiphenyl-4-carbonyl)spiro [furo[2,3-g]quinoline-3,4'-piperidine]

The title compound was prepared from 4'-(5-dimethylamino-1,2,4-oxadiazol-3-yl)-2'-methylbiphenyl-4-carboxylic acid D(14) and 2,3,5,6,7,8-hexahydro-1'-methylspiro[furo[2,3-g]quinoline-3,4'-piperidine] (D10) using a procedure similar to that of Example 1 (26%). This was converted to hydrochloride salt. M.p. 118–120° C.

$^1$H NMR (free base) (200 MHz, CDCl$_3$) δ (ppm): 7.9 (s, 1H), 7.82 (d, 1H), 7.4–7.11 (m, 5H), 6.6 (s, 1H), 6.35 (br s, 1H), 4.25 (s, 2H), 3.94 (t, 2H) 3.2 (s, 6H), 2.77 (t, 2H), 2.7–2.56 (m, 2H), 2.27 (s, 3H), 2.22 (s, 3H), 2.12–1.69 (m, 4H), 1.55–1.41 (m, 4H).

EXAMPLE 47
2,3,5,6,7,8-Hexahydro-1'-methyl-5-(4'-(5-ethyl-1,3,4-oxadiazol-2-yl)-2'-methylbiphenyl-4-carbonyl)spiro[furo[2,3-g]quinoline-3,4'-piperidine]

The title compound was prepared from 4'-(5-ethyl-1,3,4-oxadiazol-2-yl)-2'-methylbiphenyl-4-carboxylic acid (D32) and 2,3,5,6,7,8-hexahydro-1'-methylspiro[furo[2,3-g]quinoline-3,4'-piperidine] (D10) using a procedure similar to that of Example 1 (19%). This was converted to its hydrochloride salt, as a white solid. M.p. 241–3° C.

$^1$H NMR (free base) (200 MHz, CDCl$_3$) δ (ppm): 7.94 (s, 1H), 7.85 (d, 1H), 7.4–7.11 (m, 5H), 6.59 (s, 1H), 6.36 (br s, 1H), 4.26 (s, 2H), 3.95 (t, 2H), 2.98 (q, 2H), 2.78 (t, 2H), 2.71–2.58 (m, 2H), 2.3 (s, 3H), 2.25 (s, 3H), 2.14–1.61 (m, 4H), 1.58–1.35 (m, 7H).

EXAMPLE 48
2,3,5,6,7,8-Hexahydro-1'-methyl-5-(4'-methoxycarbonyl-2'-methylbiphenyl-4-carbonyl)spiro [furo[2,3-g]quinoline-3,4'-piperidine]

The title compound was prepared from 2,3,5,6,7,8-hexahydro-1'-methylspiro[furo[2,3-g]quinoline-3,4'-piperidine] (D10) and 4'-methoxycarbonyl-2'-methylbiphenyl-4-carboxylic acid (D41) using a procedure similar to that of Example 1 (46%).

$^1$H NMR (200 MHz, CDCl$_3$) δ (ppm): 7.93 (s, 1H), 7.87 (d, 1H), 7.35 (d, 2H), 7.24–7.1 (m, 3H), 6.6 (b s, 1H), 4.26 (s, 2H), 4.0–3.85 (m, 5H), 2.79 (t, 2H), 2.7–2.55 (m, 2H), 2.3–2.2 (m, 6H), 2.15–1.99 (m, 2H), 1.97–1.65 (m, 2H), 1.58–1.4 (m, 4H).

EXAMPLE 49
2,3,5,6,7,8-Hexahydro-1'-methyl-5-(4'-hydrazinocarbonyl-2'-methylbiphenyl-4-carbonyl)spiro[furo[2,3-g]quinoline-3,4'-piperidine]

The title compound was prepared from 2,3,5,6,7,8-hexahydro-1'-methyl-5-(4'-methoxycarbonyl-2'-methylbiphenyl-4-carbonyl)spiro[furo[2,3-g]quinoline-3,4'- piperidine] (E48) and hydrazine monohydrate, using a procedure similar to that of Example 25 (90%).

$^1$H NMR (200 MHz, CDCl$_3$) δ (ppm): 7.7–7.5 (m, 3H), 7.35 (d, 2H), 7.25–7.1 (m, 3H), 6.6 (s, 1H), 6.35 (br s, 1H), 4.25 (s, 2H), 4.1 (br s, 2H), 3.95 (t, 2H), 2.78 (t, 2H), 2.7–2.52 (m, 2H), 2.3–2.19 (m, 6H), 2.14–1.7 (m, 4H), 1.57–1.4 (m, 4H).

EXAMPLE 50

2,3,5,6,7,8-Hexahydro-1'-methyl-5-(2'-methyl-4'-(1,3,4-oxadiazol-2-yl)biphenyl-4-carbonyl)spiro[furo[2,3-g]quinoline-3,4'-piperidine]

A suspension of 2,3,5,6,7,8-hexahydro-1'-methyl-5-(4'-hydrazinocarbonyl-2'-methylbiphenyl-4-carbonyl)spiro[furo[2,3-g]quinoline-3,4'-piperidine] (E49) (794 mg) in triethylorthoformate (25 ml) was heated at reflux overnight. The mixture was concentrated in vacuo and the residue refluxed overnight in xylene (40 ml) to complete cyclisation. The xylene was evaporated under reduced pressure and the residue purified by chromatography on silica gel, eluting with chloroform and methanol, to afford the title compound (470 mg, 58%). The hydrochloride salt precipitated from acetone as a white solid.

$^1$H NMR (free base) (200 MHz, CDCl$_3$) δ (ppm): 8.49 (s, 1H), 7.92 (d, 1H), 7.38 (d, 2H), 7.3–7.15 (m, 3H), 6.6 (s, 1H), 6.38 (br s, 1H), 4.26 (s, 2H), 3.95 (t, 2H), 2.79 (t, 2H), 2.72–2.58 (m, 2H), 2.3 (s, 3H), 2.26 (s, 3H), 2.15–1.41 (m, 8H).

EXAMPLE 51

1'-Methyl-5-(2'-methyl-4'-pyrazinylbiphenyl-4-carbonyl)-2,3,6,7-tetrahydrospiro[furo[2,3-f]indole-3,4'-piperidine]

1'-Methyl-2,3,6,7-tetrahydrospiro[furo[2,3-f]indole-3,4'-piperidine] (0.098 g, 0.403 mmol) (D8) was dissolved in toluene (5 ml) and was treated with trimethylaluminium (2.0 M in hexane) (0.810 ml, 1.612 mmol) with stirring under argon. After 0.25 h, a solution of methyl 2'-methyl-4'-pyrazinylbiphenyl-4-carboxylate (D86, 0.136 g, 0.447 mmol) in toluene (5 ml) was added. The reaction mixture was then heated to 80° C. After 2 h, the reaction mixture was allowed to cool and was stirred at room temperature. The reaction mixture was then poured onto a slurry of silica gel (9385~20 ml) in dichloromethane (30 ml). After effervescence had ceased, the slurry was filtered and the filter pad was washed with 20% MeOH/CH$_2$Cl$_2$ (~200 ml). The filtrate was then evaporated under reduced pressure to give a brown oil, which was purified by silica-gel chromatography (9385, 10% MeOH/CH$_2$Cl$_2$ as eluant) to give the title compound as a cream solid (0.091 g, 44%).

$^1$H NMR (250 MHz, CDCl$_3$) δ (ppm): 9.08 (s, 1H), 8.68 (t, 1H), 8.52 (d, 1H), 8.14 (br s, 1H), 8.00 (s, 1H), 7.90 (dd, 1H), 7.62 (d, 2H), 7.42 (d, 2H), 7.38 (d, 1H), 6.70 (s, 1H), 4.40 (br s, 2H), 4.10 (br s, 2H), 3.10 (t, 2H), 2.90 (br s, 2H), 2.40 (s, 3H), 2.38 (s, 3H), 2.20 (br s, 2H), 1.85 (br s, 4H).

EXAMPLE 52

1'-Methyl-5-[2'-methyl-4'-(5-methyl-1,2,4-oxadiazolyl-3-yl)biphenyl-4-carbonyl]-1-oxo-2,3,6,7-tetrahydrospiro[thiophenol[2,3-f]indole-3,4'-piperidine]

A solution of 1'-methyl-5-[2'-methyl-4'-(5-methyl-1,2,4-oxadiazol-3-yl)biphenyl-4-carbonyl]-2,3,6,7-tetrahydrospiro[thiopheno[2,3-f]indole-3,4'-piperidine] (E32, 0.100 g, 0.187 mmol) in methanol (10 ml) was treated with a solution of sodium periodate (0.200 g, 0.935 mmol) in water (1 ml) with stirring. After 20 h, water (10 ml) was added and the methanol present was removed by evaporation under reduced pressure to give a white suspension. The suspension was then extracted with dichloromethane (3×25 ml). The combined organic layers were then dried (Na$_2$SO$_4$) and evaporated under reduced pressure to give a colourless oil, which was purified by preparative t.l.c. to give the title compound as a white foam (0.055 g, 53%) which was subsequently converted to its hydrochloride salt.

hu 1H NMR (200 MHz, CDCl$_3$) (free base): 8.03 (s, 1H), 7.95 (d, 1H), 7.65 (s, 1H), 7.60 (d, 2H), 7.40 (m, 4H), 4.21 (t, 2H), 3.25 (Abq, 2H), 3.18 (m, 2H), 2.95 (m, 2H), 2.70 (s, 3H), 2.40 (s, 3H), 2.35 (s, 3H), 2.15 (br m, 6H).

EXAMPLE 53

1'-Methyl-5-[2'-methyl-4'-(1-methylimidazol-2-yl)biphenyl-4-carbonyl]-2,3,6,7-tetrahydrospiro[furo[2,3-f]indole-3,4'-piperidine]

2'-Methyl-4'-(1-methylimidazol-2-yl)biphenyl-4-carboxylic acid (D90, 310 mg, 1.06 mmol) was heated at reflux in thionyl chloride (10 ml) for 30 minutes, cooled, evaporated in vacuo and the orange residue redissolved in dry THF (10 ml). 1'-Methyl-2,3,6,7-tetrahydrospiro[furo[2,3-f]indole-3,4'-piperidine] (D8, 260 mg, 1.06 mmol) and triethylamine (0.15 ml, 1.06 mmol) were added and the mixture stirred for 72 hours. The mixture was evaporated in vacuo, the residue partitioned between H$_2$O and CHCl$_3$ (4 times) and the organics combined, dried over Na$_2$SO$_4$, filtered and evaporated in vacuo. The residue was purified by flash silica-gel chromatography with 2% MeOH/CHCl$_3$ as eluant to yield the title compound as a pale yellow gum (224 mg, 41%) which was converted to the hydrochloride salt.

$^1$H NMR (free base) (200 MHz, CDCl$_3$) δ: 7.60–7.30 (m, 9H), 7.15 (s, 1H), 6.65 (s, 1H), 4.35 (d, 2H), 4.10 (s, 2H), 3.80 (s,3H), 3.10 (t, 3H), 2.90 (s, 2H), 2.35 (s, 6H), 2.15–2.00 (m, 4H), 1.90–1.70 (m, 2H).

EXAMPLE 54

1'-Methyl-5-[2'-methyl-4'-(1-methylimidazol-5-yl)biphenyl-4-carbonyl]-2,3,6,7-tetrahydrospiro[furo[2,3-f]indole-3,4'-piperidine]

2'-Methyl-4'-(1-methylimidazol-5-yl)biphenyl-4-carboxylic acid (D93, 300 mg, 1.0 mmol) was heated at reflux in thionyl (15 ml) for 1 hour, cooled and evaporated in vacuo. The residue was redissolved in dry THF (10 ml) and treated with 1'-methyl-2,3,6,7-tetrahydrospiro[furo[2,3-f]indole-3,4'-piperidine] (D8, 250 mg, 1.0 mmol) and triethylamine (143 ul, 1.0 mmol) then stirred for 18 hours. The reaction mixture was evaporated in vacuo, partitioned between water and CHCl$_3$ (3 times) and the organic extracts combined. The organics were dried over Na$_2$SO$_4$ and evaporated in vacuo to an orange gum. The gum was purified by flash silica gel chromatography (eluting with 3% MeOH/CHCl$_3$) to yield the title compound as a pale yellow gum (200 mg, 38%) which was converted to the hydrochloride salt.

$^1$H NMR (free base) (200 MHz, CDCl$_3$) δ (ppm): 7.65–7.50 (m, 3H), 7.40 (d, 2H), 7.35–7.20 (m, 4H), 7.15 (s, 1H), 6.65 (s, 1H), 4.35 (s, 2H), 4.10 (s, 2H), 3.75 (s, 3H), 3.05 (t, 2H), 2.85 (s, 2H), 2.40–2.25 (m, 6H), 2.15–1.95 (m, 4H), 1.75 (s, 2H)

EXAMPLE 55

5-[4'-(5-Hydroxymethyl-1,2,4-oxadiazol-3-yl)-2'-methylbiphenyl-4-carbonyl]-1'-methyl-2,3,6,7-tetrahydrospiro[furo[2,3-f]indole-3,4'-piperidine]

A stirred solution of 1'-methyl-2,3,6,7-tetrahydrospiro[furo[2,3-f]indole-3,4'-piperidine] (D8, 0.34 g, 1.4 mmole) in toluene (10 ml) under argon was treated with 2M trimethylaluminuim in toluene (0.7 ml, 1.4 mmole) and kept at room temp. for 20 minutes. A solution of methyl 4'-[5-(t-butyldimethylsilyloxy)-1,2,4-oxadiazol-3-yl]-2'- methylbiphenyl-4-carboxylate (D95, 0.61 g, 1.4 mmole) in toluene (10 ml) was added and the stirred mixture heated under reflux for 3 hours. The solution was allowed to cool and then poured into a stirred slurry of silica gel (10 g) in dichloromethane (30 ml). This was packed into a column and eluted with 10% methanol/chloroform. The concentrated eluant (0.8 g) was dissolved in THF (50 ml) and treated with tetraethylammonium fluoride (100 mg), then the mixture was stirred at room temp. for 1 hour, before concentrating under vacuum. The residue was treated with 10% $Na_2CO_3$ solution and extracted with dichloromethane. The extract was dried ($Na_2SO_4$), concentrated in vacuo, and the residue chromatographed on silica gel eluting with 0–5% methanol/chloroform to afford the title compound as a pale yellow oil (0.28 g, 30%). This was converted to its hydrochloride salt m.p. 273–278° C.

$^1$H NMR (250 MHz, $CDCl_3$) δ (ppm): 8.13 (s, 1H—low integration), 8.02 (s, 1H), 7.96 (d, 1H), 7.60 (d, 1H), 7.40 (d, 2H), 7.32 (d, 1H), 6.67 (s, 1H), 4.96 (s, 2H), 4.40 (br s, 2H), 4.10 (br m, 2H), 3.07 (t, 2H), 3.0–2.7 (br m, 2H), 2.31 (s, 6H), 2.4–1.6 (m, 7H).

EXAMPLE 56
1'-Methyl-5-(2'-methyl-4'-(5-methyl-1,2,4-oxadiazol-3-yl) biphenyl-4-carbonyl)-1'-oxo-2,3,6,7-tetrahydrospiro[furo[2,3-f]indole-3,4'-piperidine]

A stirred solution of 1'-methyl-5-(2'-methyl-4'-(5-methyl-1,2,4-oxadiazol-3-yl)biphenyl-4-carbonyl)-2,3,6,7-tetrahydrospiro[furo[2,3-f]indole-3,4'-piperidine] (E1, 300 mg, 0.57 mmole) in chloroform (20 ml) at −20° C. under argon was treated with a dried ($Na_2SO_4$) solution of 3-chloroperoxybenzoic acid (207 mg of 50–60% commercial purity) in chloroform (5 ml). The mixture was allowed to warm to room temp. over 20 minutes, then washed with 10% $Na_2CO_3$ solution, dried ($Na_2SO_4$) and concentrated in vacuo to leave a beige solid. This was chromatographed on silica gel eluting with 0–20% methanol/chloroform and the product crystallised from acetone to afford the title compound as a white solid (120 mg, 39%) m.p. 223–229° C.

$^1$H NMR (250 MHz, $CDCl_3$) δ (ppm): 8.25 (br s, 1H—low integration), 8.00 (d, 1H), 7.96 (dd, 1H), 7.62 (d, 2H), 7.42 (d, 2H), 7.37 (d, 1H), 6.70 (s, 1H), 4.45 (s, 2H), 4.12 (t, 2H), 3.48–3.18 (m, 4H), 3.31 (s, 3H), 3.14–2.90 (m, 2H), 3.07 (t, 2H), 2.69 (s, 3H), 2.35 (s, 3H), 1.80–1.63 (m, 2H).

EXAMPLE 57
1'-Methyl-5-[2'-methyl-4'-(1,2,4-triazin-3-yl)biphenyl-4-carbonyl]-2,3,6,7-tetrahydrospiro[furo[2,3-f]indole-3,4'-piperidine]

The title compound (100 mg, 22%) was prepared from 2'-methyl-4'-(1,2,4-triazin-3-yl)biphenyl-4-carboxylic acid (D98, 0.25 g, 0.80 mmol) according to the method of Example 1. This was converted to its hydrochloride salt.

$^1$H NMR (HCl salt) (250 MHz, $CD_3OD$) δ (ppm): 9.30 (d, 1H), 8.90 (d, 1H), 8.50 (s, 1H), 8.45 (d, 1H), 8.10 (br s, 1H), 7.75 (d, 2H), 7.60 (d, 2H), 7.50 (d, 1H), 6.80 (s, 1H), 4.60 (s, 2H), 4.20 (m, 2H), 3.65–3.55 (m, 2H), 3.28–3.10 (m, 4H), 2.95 (s, 3H), 2.45 (s, 3H), 2.40–2.20 (m, 2H), 2.15–2.00 (m, 2H).

EXAMPLE 58
2,3,6,7,8,9-Hexahydro-1'-methyl-6-(2'-methyl-4'-(5-methyl-1,3,4-oxadiazol-2-yl)biphenyl-4-carbonyl)spiro[4H-pyrano[2,3-g]quinoline-4,4' piperidine]

A solution of 2'-methyl-4'-(5-methyl-1,3,4-oxadiazol-2-yl)biphenyl-4-carboxylic acid (D11, 184 mg, 0.0006 mmole) in thionyl chloride (5 ml) under an argon atmosphere was heated to reflux for 20 minutes. The reaction mixture was allowed to cool and then concentrated in vacuo to leave an orange residue, which was dissolved in dichloromethane (5 ml) and treated with 2,3,6,7,8,9-hexahydro-1'-methylspiro[4H-pyrano[2,3-g]quinoline-4,4'-piperidine] (D107, 150 mg, 0.0006 mole) in dichloromethane (5 ml) and triethylamine (100 ul, 0.0007 mole). The solution was stirred at room temp. for 15 hrs, then concentrated in vacuo. The residue was purified by chromatography on silica gel eluting with 8% methanol/dichlormethane to afford the title compound (105 mg, 31%).

$^1$H NMR (200 MHz, $CDCl_3$) δ (ppm): 7.93 (s, 1H), 7.87 (d, 1H), 7.40 (d, 2H), 7.27–7.20 (m, 3H), 6.62 (br s, 2H), 4.02 (dd, 2H), 3.95 (t, 2H), 2.77 (t, 2H), 2.63 (s, 3H), 2.56 (br d, 2H), 2.31 (s, 3H), 2.26 (s, 3H), 2.18–2.00 (m, 4H), 1.85 (dd, 2H), 1.48 (br d, 2H), 1.28 (br d, 2H).

EXAMPLE 59
1'-Ethyl-5-(2'-methyl-4'-(5-methyl-1,3,4-oxadiazol-2-yl) biphenyl-4-carbonyl)-1'-oxo-2,3,6,7-tetrahydrospiro[furo[2,3-f]indole-3,4'-piperidine]

The title compound was prepared from 1'-ethyl-5-[2'-methyl-4'-(5-methyl-1,3,4-oxadiazol-2-yl)biphenyl-4-carbonyl]-2,3,6,7-tetrahydrospiro[furo[2,3-f]indole-3,4'-piperidine] (E26) using a similar procedure as in Example 56 to yield an off white solid (16%).

$^1$H NMR (250 MHz, $CDCl_3$) δ (ppm): 8.22 (br s, 1H—low integration), 7.98 (s, 1H), 7.91 (d, 1H), 7.64 (d, 2H), 7.48–7.30 (m, 3H), 6.69 (s, 1H), 4.48 (br s, 2H), 4.11 (br m, 2H), 3.57–2.76 (m, 10H), 2.66 (s, 3H), 2.36 (s, 3H), 1.72 (br d, 2H), 1.49 (br t, 3H).

EXAMPLE 60
1'-Ethyl-5-[4'-(5-methyl-1,3,4-oxadiazol-2-yl)biphenyl-4-carbonyl]-2,3,6,7-tetrahydrospiro[furo[2,3-f]indole-3,4'-piperidine]

The title compound was prepared from 4'-(5-methyl-1,3,4-oxadiazol-2-yl)biphenyl-4-carboxylic acid (D11) and 1'-ethyl-2,3,6,7-tetrahydrospiro[furo[2,3-f]indole-3,4'-piperidine] (D109) using a similar procedure as that outlined in Example 1, to afford the title compound as a yellow gum (31%). This was converted to its hydrochloride salt to yield an off white solid m.p. 245–249° C.

$^1$H NMR (HCl salt) (400 MHz, $d^6DMSO$) δ (ppm): 8.09 (d, 2H), 7.98 (d, 2H), 7.95 (br s, 1H), 7.88 (d, 2H), 7.72 (d, 2H), 6.77 (s, 1H), 4.52 (s, 2H), 4.06 (t, 2H), 3.50 (br d, 2H), 3.12 (m, 2H), 3.10–2.93 (m, 4H), 2.61 (s, 3H), 2.25 (br m, 2H), 1.90 (br d, 2H), 1.29 (t, 3H).

EXAMPLE 61
1'-Ethyl-5-(4'-hydrazinocarbonyl-2'-methylbiphenyl-4-carbonyl)-2,3,6,7-tetrahydrospiro[furo[2,3-f]indole-3,4'-piperidine]

A stirred solution of 1'-ethyl-5-[2'-methyl-4'-(5-methyl-1,3,4-oxadiazol-2-yl)biphenyl-4-carbonyl]-2,3,6,7-tetrahydrospiro[furo[2,3-f]indole-3,4'-piperidine] (E26, 2.5 g, 4.7 mmole) in methanol (600 ml) was treated with 1M hydrogen chloride in ether (30 ml, 30 mmole) and kept at room temp. for 20 hours, then concentrated in vacuo. The residue was treated with 10% $Na_2CO_3$ solution (200 ml) and chloroform (500 ml), stirred well for 20 minutes, then the chloroform layer separated, dried and concentrated in vacuo. The residue was crystallised from ethyl acetate to afford the title compound as a beige solid (0.94 g, 39%) m.p. 222–225° C.

$^1$H NMR (250 MHz, $CDCl_3$) δ (ppm): 8.17 (br s, 1H—low integration), 7.71 (s, 1H), 7.67–7.55 (m, 3H), 7.50 (br s, 1H), 7.38 (d, 2H), 7.28 (d, 1H), 6.67 (s, 1H), 4.50 (br s, 2H), 4.3–3.9 (br s, 4H), 3.09 (t, 2H), 2.98 (br s, 2H), 2.50–2.38 (m, 2H), 2.34 (s, 3H), 2.22–1.41 (m, 6H), 1.13 (br t, 3H).

EXAMPLE 62
5-[4'-(Acetylhydrazinocarbonyl)-2'-methylbiphenyl-4-carbonyl]-1'-ethyl-2,3,6,7-tetrahydrospiro[furo[2,3-f] indole-3,4'-piperidine]

To a stirred solution of 1'-ethyl-5-(4'-hydrazinocarbonyl-2'-methylbiphenyl-4-carbonyl)-2,3,6,7-tetrahydrospiro[furo [2,3-f]indole-3,4'-piperidine] (E61, 1.00 g, 1.96 mmole) in chloroform (30 ml), acetic anhydride (5.76 ml, 0.06 mmole) was slowly added. The solution was stirred at room temperature for approximately 1 hour, then concentrated in vacuo. Toluene was used to azeotrope out the excess acetic anhydride. The residue was dissolved in chloroform, washed with 10% $Na_2CO_3$ solution and the organic phase dried ($Na_2SO_4$), then concentrated in vacuo. The residue beige solid was chromatographed on silica gel, eluting with 0–12% methanol in chloroform to afford the title compound as a yellow solid (0.87 g, 80%) m.p. 154–157° C.

$^1$H NMR (250 MHz, $CDCl_3$) δ (ppm): 9.02 (br s, 1H), 8.17 (br s, 1H—low integration), 7.76 (s, 1H), 7.71 (dd, 1H), 7.61 (d, 2H), 7.37 (d, 2H), 7.29 (d, 1H) 6.67 (s, 1H), 4.40 (br s, 2H), 4.09 (br m, 2H), 3.06 (t, 2H), 2.98 (br m, 2H), 2.44 (br m, 2H), 2.31 (s, 3H), 2.15 (s, 3H), 2.10–1.50 (m, 6H), 1.13 (br t, 3H).

EXAMPLE 63
5-[4'-(5-Methoxymethyl-1,2,4-oxadiazol-3-yl)-2'-methylbiphenyl-4-carbonyl]-1'-methyl-2,3,6,7-tetrahydrospiro[furo[2,3-f]indole-3,4'-piperidine]

The title compound was prepared from 4'-(5-methoxymethyl-1,2,4-oxadiazol-3-yl)-2'-methylbiphenyl-4-carboxylic acid (D112) and 1'-methyl-2,3,6,7-tetrahydrospiro[furo[2,3-f]indole-3,4'-piperidine] (D8) using a similar procedure as described in Example 1. This afforded the title compound as a pale yellow solid (62%), which was converted to its hydrochloride salt to give an off white solid m.p. 247–251° C.

$^1$H NMR (free base) (250 MHz, $CDCl_3$) δ (ppm): 8.15 (s, 1H—low integration), 8.06 (s, 1H), 8.00 (dd, 1H), 7.63 (d, 2H), 7.42 (d, 2H), 7.36 (d, 1H), 6.68 (s, 1H), 4.79 (s, 2H), 4.41 (br s, 2H), 4.10 (br m, 2H), 3.59 (s, 3H), 3.08 (t, 2H), 2.88 (br s, 2H), 2.38 (s, 3H), 2.32 (br s, 3H), 2.10–1.54 (m, 6H).

EXAMPLE 64
5-[4'-(4,5-Dihydrooxazol-2-yl)-2'-methylbiphenyl-4-carbonyl]-1'-methyl-2,3,6,7-tetrahydrospiro[furo[2,3-f] indole-3,4'-piperidine]

This was prepared from methyl 4'-(4,5-dihydrooxazol-2-yl)-2'-methylbiphenyl-4-carboxylate (D114) and 1'-methyl-2,3,6,7-tetrahydrospiro[furo[2,3-f]indole-3,4'-piperidine] (D8) following the procedure of Example 12. This gave the title compound (35%) as a light yellow solid.

$^1$H NMR (200 MHz, $CDCl_3$) δ (ppm): 8.15 (b, 1H), 7.89 (s, 1H), 7.82 (d, 1H), 7.60 (d, 2H), 7.39 (d, 2H), 7.28 (d, 1H), 6.66 (s, 1H), 4.46 (t, 2H), 4.38 (s, 2H), 4.09 (t, 2H), 4.0–4.2 (b, 2H), 3.06 (t, 2H), 2.87 (m, 2H), 2.32 (s, 6H), 1.9–2.3 (m, 4H), 1.6–1.9 (m, 2H).

EXAMPLE 65
5-[4'-(2-(N,N-Dimethylamino)acetamido)-2'-methylbiphenyl-4-carbonyl]-1'-methyl-2,3,6,7-tetrahydrospiro[furo[2,3-f]indole-3,4'-piperidine]

4'-(2-Chloroacetamido)-2'-methylbiphenyl-4-carboxylic acid (D116, 0.34 g), following the procedure of Example 29, gave 5-[4'-(2-chloroacetamido)-2'-methylbiphenyl-4-carbonyl]-1'-methyl-2,3,6,7-tetrahydrospiro[furo[2,3-f] indole-3,4'-piperidine] (0.20 g, 33%) as a light yellow powder, but of low purity (HPLC). This was dissolved in ethanol (25 ml) and dichloromethane (10 ml), and dimethylamine (5.6 M in ethanol, 2 ml) was added. The suspension was stirred until homogenous, and then left to stand for 6 days. Solvents were then evaporated off, and the residue was purified by chromatography on silica gel, eluting with 0–20% methanol/dichloromethane. The crude product was dissolved in 10% methanol/dichloromethane, washed with dil. potassium carbonate solution, dried ($Na_2SO_4$) and evaporated to giver the title compound (0.06 g, 30%) as a colourless oil. This was converted into its dihydrochloride salt, a light cream powder.

$^1$H NMR (free base) (250 MHz, $CDCl_3$) δ (ppm): 9.07 (s, 1H), 8.08 (b s, 1H), 7.51 (d, 2H), 7.45 (m, 2H), 7.30 (d, 2H), 7.15 (d, 1H), 6.59 (s, 1H), 4.30 (s, 2H), 4.02 (b, 2H), 3.03 (s, 2H), 2.99 (t, 2H), 2.79 (m, 2H), 2.32 (s, 6H), 2.26 (s, 3H), 2.22 (s, 3H), 1.9–2.1 (m,4H), 1.1–1.3 (m, 2H).

EXAMPLE 66
5-[4'-(Ethoxycarbonylamino)-2'-methylbiphenyl-4-carbonyl]-1'-ethyl-2,3,6,7-tetrahydrospiro[furo[2,3-f] indole-3,4'-piperidine]

This compound was prepared from 4'-(ethoxycarbonylamino)-2'-methylbiphenyl-4-carboxylic acid (D61) and 1'-ethyl-2,3,6,7-tetrahydrosprio[furo[2,3-f] indole-3,4'-piperidine] (D109), following the procedure of Example 29. This gave the title compound (61%) as a straw coloured foam, which was converted to its hydrochloride salt.

$^1$H NMR (HCl salt) (200 MHz, $d^6DMSO$) δ (ppm): 10.16 (b, 1H), 9.67 (s, 1H), 7.93 (s, 1H), 7.61 (d, 2H), 7.41 (m, 4H), 7.16 (d, 1H), 6.76 (s, 1H), 4.51 (s, 2H), 4.13 (q, 2H), 4.04 (t, 2H), 3.5 (m, 2H), 2.9–3.2 (m, 6H), 2.23 (s, 3H), 2.1–2.3(m, 2H), 1.88 (d, 2H), 1.27 (t, 3H), 1.25 (t, 3H).

EXAMPLE 67
5-[4'-(Acetylhydrazinocarbonyl)-2'-methylbiphenyl-4-carbonyl]-1'-methyl-2,3,6,7-tetrahydrospiro[furo[2,3-f] indole-3,4'-piperidine]

The title compound was prepared from 5-(4'-hydrazinocarbonyl-2'-methylbiphenyl-4-carbonyl)-1'-methyl-2,3,6,7-tetrahydrospiro[furo[2,3-f]indole-3,4'-piperidine] (E25) using a similar procedure to Example 62 as a colourless oil (27%). HCl salt mp 235–238° C.

$^1$H NMR (250 MHz, $CDCl_3$) δ (ppm): 9.5 (br s), 8.13 (br s, 1H), 7.77 (s, 1H), 7.70 (d, 1H), 7.60 (d, 2H), 7.34 (d, 2H), 7.23 (d, 1H), 6.66 (s, 1H), 4.40 (br s, 2H), 4.08 (br m, 2H), 3.06 (t, 2H), 3.0–2.8 (br, 2H), 2.35 (s, 3H), 2.28 (s, 3H), 2.12 (s, 3H), 2.2–1.5 (m, 6H).

EXAMPLE 68
5-(4'-(5-methylfuran-2-yl)-2'-methylbiphenyl-4-carbonyl)-1'-methyl-2,3,6,7-tetrahydrospiro[furo[2,3-f]indole-3,4'-piperidine]

2'-Methyl-4'-(5-methylfuran-2-yl)biphenyl-4-carboxylic acid (D119) (160 mg, 0.55 mmol) and 1'-methyl-2,3,6,7-tetrahydrospiro[furo[2,3-f]indole-3,4'-piperidine] (D8, 134 mg, 0.55 mmol) were converted to the title compound using the method outlined in Example 29, as an off-white foam (176 mg, 62%).

$^1$H NMR (200 MHz, $CDCl_3$) δ (ppm): 8.12 (br s, 1H), 7.65–7.45 (m, 4H), 7.4 (d, 2H), 7.29–7.19 (m, 1H), 6.65 (s, 1H), 6.58 (d, 1H), 6.08 (d, 1H), 4.39 (br s, 2H), 4.21–4.0 (m, 2H), 3.05 (t, 2H), 2.93–2.75 (m, 2H), 2.38 (s, 3H), 2.3 (s, 6H), 2.11–1.9 (m, 4H), 1.84–1.6 (m, 2H).

Pharmacological Data
5-HT 1D ALPHA AND 5-HT 1D BETA BINDING.

CHO cells expressing 5-HT 1D alpha receptors (0.563×10$^8$ cells/ml) are homogenised in Tris buffer and stored in 1 ml aliquots. CHO cells expressing 5-HT 1D beta receptors (4×10$^7$ cells/ml) are homogenised in Tris buffer and stored in 1.5 ml aliquots.

0.4 ml of a cell suspension was incubated with [$^3$H]-5-HT (4 nM) in Tris Mg HCl buffer (pH 7.7) and test drug, at 37° C. for 45 minutes. Each test drug was tested at 10 concentrations (0.01 mM to 0.3 nM final concentration), with non-specific binding defined using 0.01 mM 5-HT. The total assay volume was 0.5 ml. Incubation was stopped by rapid filtration using a Packard Filtermate (filters pre-soaked in 0.3% polyethylenimine) and radioactivity measured by Topcount scintillation counting. The pKi values were calculated from the IC$_{50}$ generally by an iterative leas squares curve fitting programme.

Examples 1, 4, 5, 6, 8, 18, 23, 26, 40, 45, 51, 54, 55, 57 and 66 had pKi values >8.0 at 5-HT 1D beta receptors.

We claim:

1. A compound of formula (I) or a salt or N-oxide thereof:

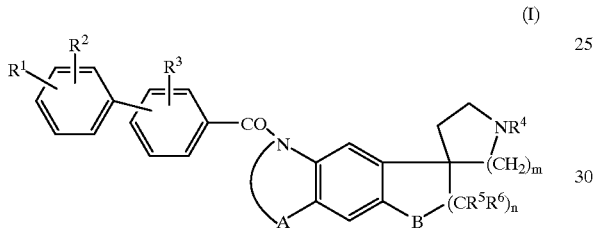

in which

R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_p$CO$_2$R$^{11}$, (CH$_2$)$_p$NR$^{10}$R$^{11}$, (CH$_2$)$_p$CONR$^{10}$R$^{11}$, (CH$_2$)$_p$NR$^{10}$COR$^{11}$, (CH$_2$)$_p$CO$_2$C$_{1-6}$alkyl, CO$_2$(CH$_2$)$_p$OR$^{10}$, CONHNR$^{10}$R$^{11}$, NR$^{10}$R$^{11}$, NR$^{10}$CO$_2$R$^{11}$, NR$^{10}$CO(CH$_2$)$_p$NR$^{10}$R$^{11}$, NR$^{10}$CONR$^{10}$R$^{11}$, CR$^{10}$=NOR$^{11}$, CNR$^{10}$=NOR$^{11}$, where R$^9$, R$^{10}$ and R$^{11}$ are independently hydrogen or C$_{1-6}$alkyl and p is 1 to 4; or R$^1$ is an optionally substituted 5 to 7-membered heterocyclic ring containing 1 to 4 heteroatoms selected from oxygen, nitrogen or sulphur;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl;

R$^4$ is hydrogen or C$_{1-6}$alkyl;

R$^5$ and R$^6$ are independently hydrogen or C$_{1-6}$alkyl;

A is (CR$^{13}$R$^{14}$)$_q$ where q is 2, 3 or 4 and R$^{13}$ and R$^{14}$ are independently hydrogen or C$_{1-6}$alkyl or A is (CR$^{13}$R$^{14}$)$_r$—D where r is 0, 1, 2 or 3 and D is oxygen, sulphur or CR$^{13}$=CR$^{14}$ B is oxygen, CR$^{15}$R$^{16}$ or NR$^{17}$ where R$^{15}$, R$^{16}$ and R$^{17}$ are independently hydrogen or C$_{1-6}$alkyl or B is S(O)$_b$ where b is 0, 1 or 2;

m is 1, 2 or 3; and n is 1, 2 or 3.

2. A compound according to claim 1 in which R$^1$ is COC$_{1-6}$alkyl, CR$^{10}$=NOR$^{11}$, (CH$_2$)$_p$NR$^{10}$COR$^{11}$, CO$_2$R$^{10}$, NR$^{10}$SO$_2$R$^{11}$, SO$_2$NR$^{10}$R$^{11}$, CONR$^{10}$R$^{11}$, CONHNR$^{10}$R$^{11}$, NR$^{10}$CO$_2$R$^{11}$, NR$^{10}$CONR$^{10}$R$^{11}$, CONHNR$^{10}$R$^{11}$ or SO$_2$R$^9$ or R$^1$ is optionally substituted oxadiazole.

3. A compound according to claim 1 in which R$^2$ is C$_{1-6}$alkyl.

4. A compound according to claim 1 in which m is 2.

5. A compound according to claim 1 in which R$^4$ is hydrogen, methyl or ethyl.

6. A compound according to claim 1 in which n is 1.

7. A compound according to claim 1 which is:

1'-Methyl-5-(2'-methyl-4'-(5-methyl-1,2,4-oxadiazol-3-yl)biphenyl-4-carbonyl)-2,3,6,7-tetrahydrospiro[furo[2,3-f]indole-3,4'-piperidine];

2,3,5,6,7,8-Hexahydro-1'-methyl-5-(2'-methyl-4'-(5-methyl-1,2,4-oxadiazol-3-yl)biphenyl-4-carbonyl)spiro[furo[2,3-g]quinoline-3,4'-piperidine];

5-(2'-Methyl-4'-(5-methyl-1,2,4-oxadiazol-3-yl)biphenyl-4-carbonyl)-2,3,6,7-tetrahydrospiro[furo[2,3-f]indole-3,4'-piperidine];

1'-Ethyl-5-(2'-methyl-4'-(5-methyl-1,2,4-oxadiazol-3-yl)biphenyl-4-carbonyl)-2,3,6,7-tetrahydrospiro[furo[2,3-f]indole-3,4'-piperidine];

1'-Methyl-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine];

5-(4'-(5-Dimethylamino-1,2,4-oxadiazol-3-yl)-2'-methylbiphenyl-4-carbonyl)-1'-methyl-2,3,6,7-tetrahydrospiro[furo[2,3-f]indole-3,4'-piperidine];

1'-Methyl-5-[4'-(5-methyl-1,2,4-oxadiazol-3-yl)biphenyl-4-carbonyl]-2,3,6,7-tetrahydrospiro[furo[2,3-f]indole-3,4'-piperidine];

2,3-Dihydro-1'-methyl-5-(2'-methyl-4'-(5-methyl-1,2,4-oxadiazol-3-yl)biphenyl-4-carbonyl)spiro[furo[2,3-f]indole-3,4'-piperidine];

5-[4'-Cyano-2'-methylbiphenyl-4-carbonyl]-1'-methyl-2,3,6,7-tetrahydrospiro[furo[2,3-f]indole-3,4'-piperidine];

5-(4'-Acetyl-2'-methylbiphenyl-4-carbonyl)-1'-methyl-2,3,6,7-tetrahydrospiro[furo[2,3-f]indole-3,4'-piperidine];

5-(4'-(1-Methoxyamino)ethyl)-2'-methylbiphenyl-4-carbonyl)-1'-methyl-2,3,6,7-tetrahydrospiro[furo[2,3-f]indole-3,4'-piperidine];

5-(4'-Acetamidomethyl-2'-methylbiphenyl-4-carbonyl)-1'-methyl-2,3,6,7-tetrahydrospiro[furo[2,3-f]indole-3,4'-piperidine];

3,5,6,7,8,9-Hexahydro-1'-methyl-5-(2'-methyl-4'-(5-methyl-1,2,4-oxadiazol-3-yl)biphenyl-4-carbonyl)spiro[2H-furo[2,3-h]benzazepine-3,4'-piperidine];

1'-Methyl-5-(2'-methyl-4'-(3-methyl-1,2,4-oxadiazol-5-yl)biphenyl-4-carbonyl)-2,3,6,7-tetrahydrospiro[furo[2,3-f]indole-3,4'-piperidine];

1'-Methyl-5-(2'-methyl-4'-(1,3,4-oxadiazol-2-yl)biphenyl-4-carbonyl)-2,3,6,7-tetrahydrospiro[furo[2,3-f]indole-3.4'-piperidine;

5-[4'-(5-Ethyl-1,3,4-oxadiazol-2-yl)-2'-methylbiphenyl-4-carbonyl]-1'-methyl-2,3,6,7-tetrahydrospiro[furo[2,3-f]indole-3,4'-piperidine];

5-[2'-Methyl-4'-(5-methyl-1,3,4-oxadiazol-2-yl)biphenyl-4-carbonyl]-2,3,6,7-tetrahydrospiro[furo[2,3-f]indole-3,4'-piperidine];

2,3-Dihydro-1'-methyl-5-(2'-methyl-4'-(5-methyl-1,3,4-oxadiazol-2-yl)biphenyl-4-carbonyl)spiro[furo[2,3-f]indole-3,4'-piperidine];

5-(2,2'-Dimethyl-4'-(5-methyl-1,3,4-oxadiazol-2-yl)biphenyl-4-carbonyl)-1'-methyl-2,3,6,7-tetrahydrospiro[furo[2,3-f]indole-3,4'-piperidine];

5-(2,3'-Dimethyl-4'-(5-methyl-1,3,4-oxadiazol-2-yl)biphenyl-4-carbonyl)-1'-methyl-2,3,6,7-tetrahydrospiro[furo[2,3-f]indole-3,4'-piperidine];

1'-Methyl-5-(2'-methyl-4'-(4-methylthiazol-2-yl)biphenyl-4-carbonyl)-2,3,6,7-tetrahydrospiro[furo[2,3-f]indole-3,4'-piperidine];

5-(4'-Methoxycarbonyl-2'-methylbiphenyl-4-carbonyl)-1'-methyl-2,3,6,7-tetrahydrospiro[furo[2,3-f]indole-3,4'-piperidine];

5-(5'-Methoxycarbonyl-2'-methylbiphenyl-4-carbonyl)-1'-methyl-2,3,6,7-tetrahydrospiro[furo[2,3-f]indole-3,4'-piperidine];

5-[4'-(Methanesulphonamino)-2'-methylbiphenyl-4-carbonyl]-1'-methyl-2,3,6,7-tetrahydrospiro[furo[2,3-f]indole-3,4'-piperidine];

5-(4'-Hydrazinocarbonyl-2'-methylbiphenyl-4-carbonyl)-1'-methyl-2,3,6,7-tetrahydrospiro[furo[2,3-f]indole-3,4'-piperidine];

1'-Ethyl-5-(2'-methyl-4'-(5-methyl-1,3,4-oxadiazol-2-yl)biphenyl-4-carbonyl)-2,3,6,7-tetrahydrospiro[furo[2,3-f]indole-3,4'-piperidine];

1'-Methyl-5-(2'-methyl-5'-(5-methyl-1,3,4-oxadiazol-2-yl)biphenyl-4-carbonyl)-2,3,6,7-tetrahydrospiro[furo[2,3-f]indole-3,4'-piperidine];

5-(4'-Carboxamido-2'-methylbiphenyl-4-carbonyl)-1'-methyl-2,3,6,7-tetrahydrospiro[furo[2,3-f]indole-3,4'-piperidine];

5-(4'-Acetamido-2'-methylbiphenyl-4-carbonyl)-1'-methyl-2,3,6,7-tetrahydrospiro[furo[2,3-f]indole-3,4'-piperidine];

2,3,5,6,7,8-Hexahydro-1'-methyl-5-(2'-methyl-4'-(5-methyl-1,3,4-oxadiazol-2-yl)biphenyl-4-carbonyl)spiro[furo[2,3-g]quinoline-3,4'-piperidine];

2,3,5,6,7,8-Hexahydro-5-(4'-methanesulphonamino-2'-methylbiphenyl-4-carbonyl)-1'-methylspiro[furo[2,3-g]quinoline-3,4'-piperidine];

1'-Methyl-5-[2'-methyl-4'-(5-methyl-1,2,4-oxadiazol-3-yl)biphenyl-4-carbonyl]-2,3,6,7-tetrahydrospiro[thiopheno[2,3-f]indole-3,4'-piperidine];

1,2,3,5,6,7-Hexahydro-1'-methyl-1-(2'-methyl-4'-(5-methyl-1,3,4-oxadiazol-2-yl)biphenyl-4-carbonyl)spiro[indeno[5,6-b]pyrrole-7,4'-piperidine];

5-[4'-(N-methanesulphonyl-N-methylamino)-2'-methylbiphenyl-4-carbonyl]-1'-methyl-2,3,6,7-tetrahydrospiro[furo[2,3-f]indole-3,4'-piperidine];

5-[4'-(Dimethylaminosulphonyl)biphenyl-4-carbonyl]-1'-methyl-2,3,6,7-tetrahydrospiro[furo[2,3-f]indole-3,4'-piperidine];

5-[4'-(Methanesulphonyl)biphenyl-4-carbonyl]-1'-methyl-2,3,6,7-tetrahydrospiro[furo[2,3-f]indole-3,4'-piperidine];

5-[4'-(N,N-Dimethylcarbamoylamino)-2'-methylbiphenyl-4-carbonyl]-1'-methyl-2,3,6,7-tetrahydrospiro[furo[2,3-f]indole-3,4'-piperidine];

5-[4'-(Ethoxycarbonylamino)-2'-methylbiphenyl-4-carbonyl]-1'-methyl-2,3,6,7-tetrahydrospiro[furo[2,3-f]indole-3,4'-piperidine];

5-[4'-(4,5-Dimethyl-1,2,4-triazol-3-yl)-2'-methylbiphenyl-4-carbonyl]-1'-methyl-2,3,6,7-tetrahydrospiro[furo[2,3-f]indole-3,4'-piperidine];

1'-Methyl-6-[2'-methyl-4'-(5-methyl-1,3,4-oxadiazol-2-yl)biphenyl-4-carbonyl]-2,3,7,8-tetrahydrospiro[4H-pyrano[2,3-f]indole-4,4'-piperidine];

1'-Methyl-5-(2'-methyl-4'-(5-methyl-1,3,4-thiadiazol-2-yl)biphenyl-4-carbonyl)-2,3,6,7-tetrahydrospiro[furo[2,3-f]indole-3,4'-piperidine];

5-(2'-Methyl-4'-(5-methyl-1,3,4-oxadiazol-2-yl)biphenyl-4-carbonyl)-1'-n-propyl-2,3,6,7-tetrahydrospiro[furo[2,3-f]indole-3,4'-piperidine];

1'-Methyl-5-(2'-methyl-4'-(5-methyloxazol-2-yl)biphenyl-4-carbonyl)-2,3,6,7-tetrahydrospiro[furo[2,3-f]indole-3,4'-piperidine];

1'-Methyl-5-(2'-methyl-4'-(3-methylisoxazol-5-yl)biphenyl-4-carbonyl)-2,3,6,7-tetrahydrospiro[furo[2,3-f]indole-3,4'-piperidine];

1'-Methyl-5-(2'-methyl-4'-(5-methylisoxazol-3-yl)biphenyl-4-carbonyl)-2,3,6,7-tetrahydrospiro[furo[2,3-f]indole-3,4'-piperidine];

2,3,5,6,7,8-Hexahydro-1'-methyl-5-(4'-(5-dimethylamino-1,2,4-oxadiazol-3-yl)-2'-methylbiphenyl-4-carbonyl)spiro[furo[2,3-g]quinoline-3,4'-piperidine];

2,3,5,6,7,8-Hexahydro-1'-methyl-5-(4'-(5-ethyl-1,3,4-oxadiazol-2-yl)-2'-methylbiphenyl-4-carbonyl)spiro[furo[2,3-g]quinoline-3,4'-piperidine];

2,3,5,6,7,8-Hexahydro-1'-methyl-5-(4'-methoxycarbonyl-2'-methylbiphenyl-4-carbonyl)spiro[furo[2,3-g]quinoline-3,4'-piperidine];

2,3,5,6,7,8-Hexahydro-1'-methyl-5-(4'-hydrazinocarbonyl-2'-methylbiphenyl-4-carbonyl)spiro[furo[2,3-g]quinoline-3,4'-piperidine];

2,3,5,6,7,8-Hexahydro-1'-methyl-5-(2'-methyl-4'-(1,3,4-oxadiazol-2-yl)biphenyl-4-carbonyl)spiro[furo[2,3-g]quinoline-3,4'-piperidine];

1'-Methyl-5-(2'-methyl-4'-pyrazinylbiphenyl-4-carbonyl)-2,3,6,7-tetrahydrospiro[furo[2,3-f]indole-3,4'-piperidine];

1'-Methyl-5-[2'-methyl-4'-(5-methyl-1,2,4-oxadiazolyl-3-yl)biphenyl-4-carbonyl]-1-oxo-2,3,6,7-tetrahydrospiro[thiopheno[2,3-f]indole-3,4'-piperidine];

1'-Ethyl-5-[2'-methyl-4'-(5-methyl-1,3,4-oxadiazol-2-yl)biphenyl-4-carbonyl]-2,3,6,7-tetrahydrospiro[furo[2,3-f]indole-3,4'-piperidine];

1'-Methyl-5-[2'-methyl-4'-(1-methylimidazol-2-yl)biphenyl-4-carbonyl]-2,3,6,7-tetrahydrospiro[furo[2,3-f]indole-3,4'-piperidine];

1'-Methyl-5-[2'-methyl-4'-(1-methylimidazol-5-yl)biphenyl-4-carbonyl]-2,3,6,7-tetrahydrospiro[furo[2,3-f]indole-3,4'-piperidine];

5-[4'-(5-Hydroxymethyl-1,2,4-oxadiazol-3-yl)-2'-methylbiphenyl-4-carbonyl]-4'-methyl-2,3,6,7-tetrahydrospiro[furo[2,3-f]indole-3,4'-piperidine];

1'-Methyl-5-(2'-methyl-4'-(5-methyl-1,2,4-oxadiazol-3-yl)biphenyl-4-carbonyl)-1'-oxo-2,3,6,7-tetrahydro[furo[2,3-f]indole-3,4'-piperidine];

1'-Methyl-5-[2'-methyl-4'-(1,2,4-triazin-3-yl)biphenyl-4-carbonyl]-2,3,6,7-tetrahydrospiro[furo[2,3-f]indole-3,4'-piperidine];

2,3,6,7,8,9-Hexahydro-1'-methyl-6-(2'-methyl-4'-(5-methyl-1,3,4-oxadiazol-2-yl)biphenyl-4-carbonyl)spiro[4H-pyrano[2,3-g]quinoline-4,4'-piperidine];

1'-Ethyl-5-(2'-methyl-4'-(5-methyl-1,3,4-oxadiazol-2-yl)biphenyl-4-carbonyl)-1'-oxo-2,3,6,7-tetrahydrospiro[furo[2,3-f]indole-3,4'-piperidine];

1'-Ethyl-5-[4'-(5-methyl-1,3,4-oxadiazol-2-yl)biphenyl-4-carbonyl]-2,3,6,7-tetrahydrospiro[furo[2,3-f]indole-3,4'-piperidine];

1'-Ethyl-5-(4'-hydrazinocarbonyl-2'-methylbiphenyl-4-carbonyl)-2,3,6,7-tetrahydrospiro[furo[2,3-f]indole-3,4'-piperidine];

5-[4'-(Acetylhydrazinocarbonyl)-2'-methylbiphenyl-4-carbonyl]-1'-ethyl-2,3,6,7-tetrahydrospiro[furo[2,3-f]indole-3,4'-piperidine];

5-[4'-(5-Methoxymethyl-1,2,4-oxadiazol-3-yl)-2'-methylbiphenyl-4-carbonyl]-1'-methyl-2,3,6,7-tetrahydrospiro[furo[2,3-f]indole-3,4'-piperidine];

5-[4'-(4,5-Dihydrooxazol-2-yl)-2'-methylbiphenyl-4-carbonyl]-1'-methyl-2,3,6,7-tetrahydrospiro[furo[2,3-f]indole-3,4'-piperidine];

5-[4'-(2-N,N-Dimethylamino)acetamido)-2'-methylbiphenyl-4-carbonyl]-1'-methyl-2,3,6,7-tetrahydrospiro[furo[2,3-f]indole-3,4'-piperidine];

5-[4'-(Ethoxycarbonylamino)-2'-methylbiphenyl-4-carbonyl]-1'-ethyl-2,3,6,7-tetrahydrospiro[furo[2,3-f]indole-3,4'-piperidine];

5-[4'-(Acetylhydrazinocarbonyl)-2'-methylbiphenyl-4-carbonyl]-1'-methyl-2,3,6,7-tetrahydrospiro[furo[2,3-f]indole-3,4'-piperidine]; or 5-(4'-(5-methylfuran-2-yl)-2'-methylbiphenyl-4-carbonyl)-1'-methyl-2,3,6,7-tetrahydrospiro[furo[2,3-f]indole-3,4'-piperidine];

or pharmaceutically acceptable salts or N-oxides thereof.

8. A process for the preparation of a compound of formula (I) as defined in claim 1 which comprises:

(a) reaction of a compound of formula (II):

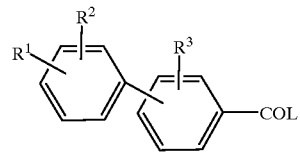

(II)

in which $R^1$, $R^2$ and $R^3$ are as defined in formula (I) and L is a leaving group with a compound of formula (III):

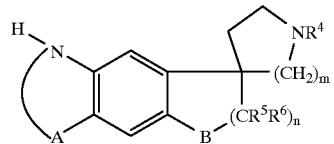

(III)

wherein $R^4$, $R^5$, $R^6$ A, B, m and n are as defined in formula (I) and optionally thereafter in any order:
    converting a compound of formula (I) into another compound of formula (I)
    forming a pharmaceutically acceptable salt or N-oxide.

9. A method of treating a disease state associated with activity of the $5HT_{1D}$ receptor which method involves treating a patient in need thereof with a therapeutically effective amount of a $5HT_{1D}$ antagonist of formula (I) as defined in claim 1.

10. A method as claimed in claim 9 in which the disease state is associated with CNS disorders.

11. A method as claimed in claim 9 in which the disease state is associated with endocrine disorders.

12. A pharmaceutical composition which comprises a compound according to claim 1 in association with a pharmaceutically acceptable carrier or excipient.

* * * * *